US012566180B2

(12) United States Patent
Comunale et al.

(10) Patent No.: US 12,566,180 B2
(45) Date of Patent: Mar. 3, 2026

(54) METHODS OF DIAGNOSING OR TREATING LYME DISEASE

(71) Applicant: Drexel University, Philadelphia, PA (US)

(72) Inventors: Mary Comunale, Bangor, PA (US); Benjamin Haslund-Gourley, Santa Barbara, CA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 18/640,086

(22) Filed: Apr. 19, 2024

(65) Prior Publication Data

US 2024/0288443 A1 Aug. 29, 2024

Related U.S. Application Data

(63) Continuation of application No. PCT/US2022/047442, filed on Oct. 21, 2022.

(60) Provisional application No. 63/270,439, filed on Oct. 21, 2021.

(51) Int. Cl.
| | |
|---|---|
| *G01N 33/53* | (2006.01) |
| *A61K 31/431* | (2006.01) |
| *A61K 31/65* | (2006.01) |
| *A61K 31/7036* | (2006.01) |
| *G01N 33/68* | (2006.01) |

(52) U.S. Cl.
CPC ....... *G01N 33/6854* (2013.01); *A61K 31/431* (2013.01); *A61K 31/65* (2013.01); *A61K 31/7036* (2013.01); *G01N 2440/38* (2013.01); *G01N 2800/26* (2013.01); *G01N 2800/56* (2013.01)

(58) Field of Classification Search
None
See application file for complete search history.

(56) References Cited

U.S. PATENT DOCUMENTS

| | | | | |
|---|---|---|---|---|
| 10,802,022 | B1 * | 10/2020 | Bradshaw | ............ C07K 14/245 |
| 2013/0296184 | A1 * | 11/2013 | Joosten | .............. G01N 33/6869 |
| | | | | 435/6.12 |
| 2017/0313767 | A1 * | 11/2017 | Alter | ...................... C07K 14/35 |
| 2022/0034880 | A1 | 2/2022 | Weissman et al. | |

FOREIGN PATENT DOCUMENTS

| | | |
|---|---|---|
| KR | 20210084485 A | 7/2021 |
| WO | 2020072534 A1 | 4/2020 |
| WO | 2023069725 A1 | 4/2023 |

OTHER PUBLICATIONS

Vigerust, David, Protein glycosylation in infectious disease pathobiology and treatment, Cent. Eur. J. Biol. 6(5), 2011, pp. 802-816. (Year: 2011).*
Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*
Zhang et al., Sensitive and robust MALDI-TOF-MS glycomics analysis enabled by Girard's reagent T on-target derivatization (GOTD) of reducing glycans, Anal Chim Acta, Feb. 7, 2019, 1048: pp. 1-21. (Year: 2019).*
"International Search Report and Written Opinion dated Jan. 8, 2024 for Application No. PCT/US2023/034148".
Callewaert , et al., "Increased fucosylation and reduced branching of serum glycoprotein N-glycans in all known subtypes of congenital disorder of glycosylation I", Glycobiology, vol. 13(5), 2003, 367-75.
Haslund-Gourley , et al., "Acute lyme disease IgG N-linked glycans contrast the canonical inflammatory signature.", Front Immunol., vol. 13:949118, Aug. 5, 2022, 1-12.
Supplementary European Search Report for European Appln. No. EP 22 88 4533 dated Jul. 8, 2025.

* cited by examiner

*Primary Examiner* — Gary Counts
(74) *Attorney, Agent, or Firm* — Saul Ewing LLP; Domingos Silva; Chihao Wang

(57) ABSTRACT

Described herein is a method of diagnosing Lyme disease in a subject. The method includes determining a glycosylation profile of a protein whose glycosylation profile is associated with Lyme disease in a subject, and comparing the glycosylation profile of the protein with a predetermined glycosylation profile of the protein indicating free of Lyme disease or a predetermined glycosylation profile of the protein indicating Lyme disease. Further described herein is a method of treating and/or ameliorating Lyme disease in a subject. The method includes diagnosing Lyme disease in a subject and, if the subject is diagnosed to have Lyme disease, administering to the subject an effective amount of compound effective for treating Lyme disease. Further described herein is a method of evaluating a treatment for Lyme disease. The method includes comparing a glycosylation profile of the patient with glycosylation profiles associated with successful/unsuccessful treatments.

8 Claims, 55 Drawing Sheets

Identify Lyme disease Specific Biomarkers

*Borrelia* Distrupts Lymphatic Immune Cells

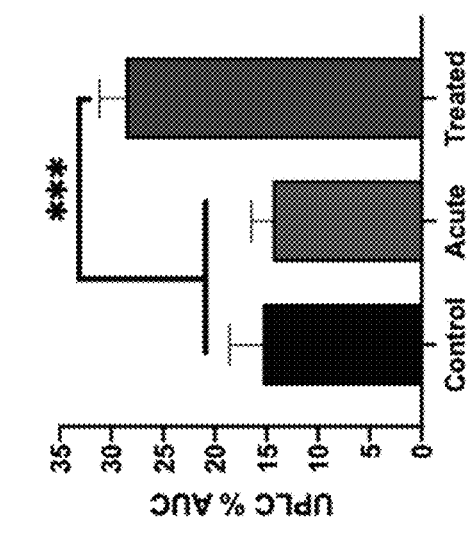
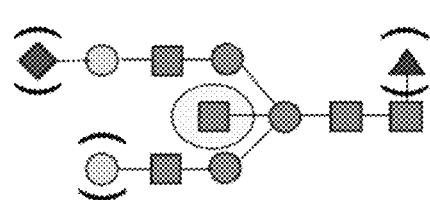
Fig. 3B
Treatment Response Biomarker
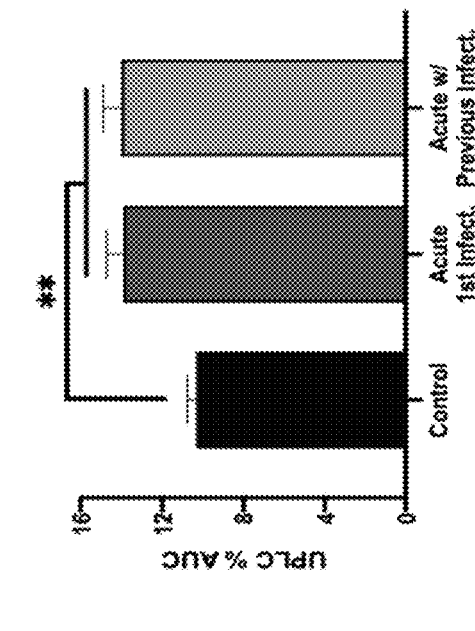
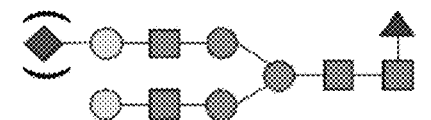
Fig. 3A
3A. 1st vs Previous Acute LD Infection

| Disease | IgG Fc N-Glycan Profile | Method of Detection |
|---|---|---|
| Rheumatoid Arthritis (RA) and Osteoarthritis (OA) | Decreased Galactose<br>Decreased Bisects<br>Elevated Agalactose | Mass Spectrometry - MALDI-TOF |
| Tuberculosis<br>Infective endocarditis<br>Visceral leishmaniasis | Decreased Galactose<br>Decreased Galactose<br>Decreased Galactose<br>Decreased Sialyation<br>Decreased Bisects | Radiolabels and sequential exoglycosidase digestion<br>Lectin Analysis<br>Mass Spectrometry - MALDI-TOF |
| Hepatitis B: chronic infection<br>Hepatitis C - anti-Gal IgG | Decreased Galactose<br>Decreased Galactose<br>Increased Fucose | Liquid Chromatography and Mass Spectrometry<br>Liquid Chromatography and Lectin Analysis |
| Liver Fibrosis | Increased Bisects<br>Decreased Galactose | Mass Spectrometry - MALDI-Imaging |
| Inflammatory bowel disease & Crohn's disease | Decreased Galactose<br>Decreased Sialyation | Liquid Chromatography and Fluorescent Detection |
| Endometriosis | Decreased Sialyation & Galactose<br>Increased Bisects | Liquid Chromatography and Fluorescent Detection |
| Systemic Lupus | Decreased Galactose<br>Decreased Sialyation<br>Decreased Fucose<br>Increased Bisects | Liquid Chromatography and Fluorescent Detection |
| Moderate COVID-19 | Decreased Galactose<br>Increased Agalactose | Liquid Chromatography and Mass Spectrometry |

Inflammatory diseases have serum IgG with N-glycan alterations that promote a pro-inflammatory signaling cascade due to a reduction in terminal galactose and sialic acid.

Fig. 5

| | Sample'n | | Avg Age | Female | Hispanic Latino | Wisconsin | Long Island | Serum Collected after treatment? |
|---|---|---|---|---|---|---|---|---|
| Pilot Set | Control | n=7 | 46.4 | 42.9 | 42.9 | 0 | 100 | Not Applicable |
| Pilot Set | Lyme disease | n=5 Acute n=3 Treated | 51.4 | 40.0 | 40.0 | 0 | 100 | Yes |
| Confirmatory Set | Control | n=18 | 51.3 | 40.9 | 22.7 | 18.2 | 81.8 | Not Applicable |
| Confirmatory Set | Lyme disease | n=18 Acute n=18 Treated | 53.1 | 40.0 | 20.0 | 20.0 | 80.0 | Yes |

Healthy Control and Lyme disease LD with matched Acute and Post-treatment Demographics of Bay Area Lyme Disease Biobank Serum Samples. Sample ID numbers are linked to demographic details including age, sex, ethnicity, and if the patient donated a post-treatment convalescent serum sample.

Fig. 6

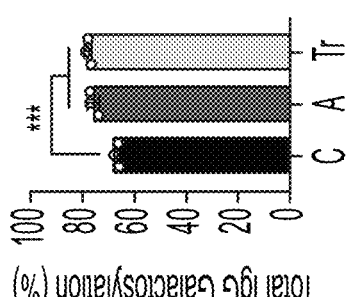
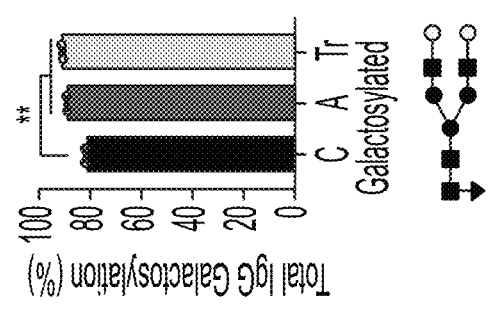
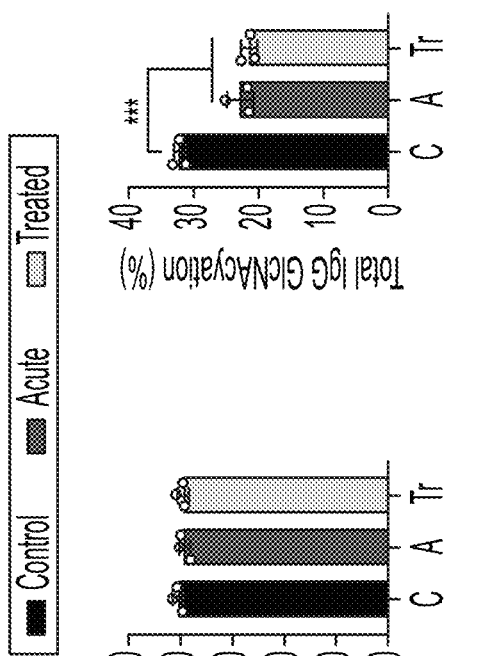
Fig. 8A
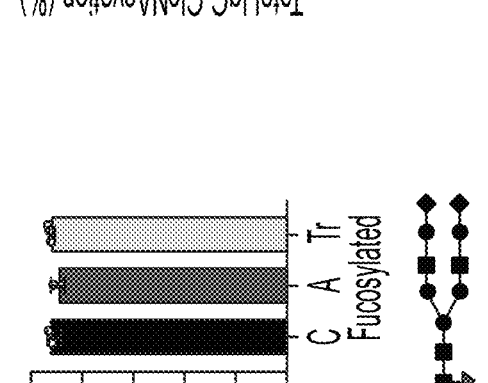
Fig. 8B
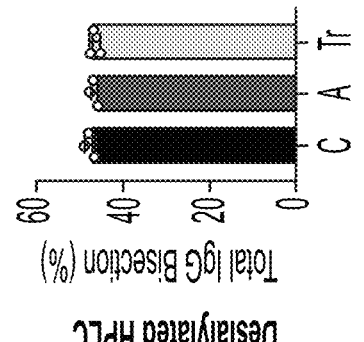
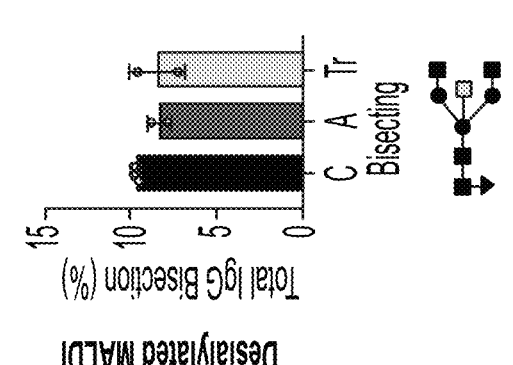

Discriminators:

Control vs Acute

F(6)A2G0
F(6)A2G2
% Total Galactose
% Digalactose

Acute met >3/4 ROC thresholds considered positive

| | |
|---|---|
| Sensitivity | 75.0 % |
| Specificity | 100.0 % |
| PPV | 100.0 % |
| NPV | 75.0 % |
| False Positive Rate | 0.0 % |
| Accuracy | 85.7 % |

Control vs Treated

F(6)A2G0
A2G1
F(6)A2G1
F(6)A2G2
F(6)A2BG1
F(6)A2BG2
% Fucose
% Total Galactose

Treated met >5/8 ROC thresholds considered positive

| | |
|---|---|
| Sensitivity | 100.0 % |
| Specificity | 94.7 % |
| PPV | 94.7 % |
| NPV | 100.0 % |
| False Positive Rate | 5.3 % |
| Accuracy | 97.3 % |

Acute vs Treated

A2G1
F(6)A2G1
F(6)A2G2
F(6)A2BG1
F(6)A2BG2
% Fucose
% Digalactose

Treated met >4/7 ROC thresholds considered positive

| | |
|---|---|
| Sensitivity | 100.0 % |
| Specificity | 100.0 % |
| PPV | 100.0 % |
| NPV | 100.0 % |
| False Positive Rate | 0.0 % |
| Accuracy | 100.0 % |

Fig. 10

Proof of
Concept

Traditional HPLC Analysis
Pooled Pilot Cohort:
Control, Acute, Post-Treatment

MALDI Analysis
Pooled Pilot Cohort:
Control, Acute, Post-Treatment

Compare IgG
N-glycan Results

Confirmatory
Set

High-Throughput MALDI Analysis
Confirmatory Cohorts of 18 Individuals per
Control, Acute, Post-Treatment Control vs Acute LD

| | Error | | Direction | 0 | 100 | 100 | 100 | |
|---|---|---|---|---|---|---|---|---|
| | | | Rule: | 12 | 29.85 | 87 | 75 | Criteria |
| | | | ID | 1485 | 1809 | % Galcatose | % Term DiGal>3/4 | |
| | | | Ctrl1 138 | 22.04 | 21.56 | 77.96 | 63.43 | N |
| | | | Ctrl1 159 | 17.67 | 26.29 | 82.33 | 70.61 | N |
| | | | Ctrl1 162 | 17.36 | 23.06 | 82.64 | 69.83 | N |
| | | | Ctrl1 163 | 12.69 | 28.67 | 87.31 | 72.82 | N |
| | | | Ctrl1 164 | 16.30 | 25.48 | 83.70 | 67.24 | N |
| | | | Ctrl1 166 | 18.89 | 24.95 | 81.11 | 69.71 | N |
| | | | Ctrl1 173 | 9.92 | 29.65 | 90.08 | 74.18 | N |
| | | | Ctrl1 174 | 14.52 | 26.57 | 85.48 | 65.92 | N |
| | | | Ctrl1 175 | 13.66 | 27.61 | 86.34 | 69.32 | N |
| | | | Ctrl1 176 | 26.93 | 20.83 | 73.07 | 60.31 | N |
| | | | Ctrl1 177 | 15.27 | 31.40 | 84.73 | 76.60 | N |
| | | | Ctrl1 184 | 15.33 | 28.77 | 84.67 | 73.09 | N |
| | | | Ctrl1 187 | 13.31 | 29.53 | 86.69 | 76.10 | N |
| | | | Ctrl1 190 | 15.88 | 28.07 | 84.12 | 71.81 | N |
| | | | Ctrl1 191 | 7.28 | 27.20 | 92.72 | 62.19 | N |
| | | | Ctrl1 515 | 13.99 | 27.58 | 86.01 | 73.35 | N |
| | | | Ctrl1 526 | 15.72 | 28.58 | 84.28 | 75.09 | N |
| | | | Ctrl1 538 | 16.45 | 26.07 | 83.55 | 70.97 | N |
| WM52 | R1 | | Acute1 160 | 19.65 | 27.11 | 80.35 | 69.12 | N |
| WM58 | R1 | | Acute1 161 | 18.31 | 26.67 | 81.69 | 66.24 | N |
| | | | Acute1 165 | 9.50 | 31.72 | 90.50 | 73.84 | Y |
| | | | Acute1 167 | 11.77 | 31.07 | 88.23 | 72.03 | Y |
| WM46 | R1 | | Acute1 168 | 11.96 | 27.87 | 88.04 | 73.03 | N |

Fig. 14

| | | | | | | | |
|---|---|---|---|---|---|---|---|
| | | Acute1 169 | 10.17 | 30.05 | 89.83 | 70.47 | Y |
| | | Acute1 170 | 10.01 | 31.53 | 89.99 | 71.59 | Y |
| | | Acute1 171 | 8.51 | 31.75 | 91.49 | 76.52 | Y |
| WF62 | FN | Acute1 172 | 13.71 | 25.76 | 86.29 | 71.34 | N |
| | | Acute1 183 | 10.80 | 32.86 | 89.20 | 77.39 | Y |
| WM32 | FN | Acute1 185 | 13.46 | 29.49 | 86.54 | 71.53 | N |
| | | Acute1 186 | 9.57 | 33.61 | 90.43 | 77.95 | Y |
| | | Acute1 188 | 9.02 | 42.22 | 90.98 | 82.16 | Y |
| | | Acute1 189 | 10.34 | 32.64 | 89.66 | 77.94 | Y |
| HM54 | FN | Acute1 192 | 26.42 | 27.23 | 73.58 | 65.12 | N |
| | | Acute1 640 | 8.76 | 34.79 | 91.24 | 77.56 | Y |
| | | Acute1 663 | 10.83 | 32.97 | 89.17 | 76.98 | Y |
| | | Acute1 673 | 5.01 | 41.90 | 94.99 | 81.95 | Y |

| | | Gold Standard | |
|---|---|---|---|
| | | + | - |
| Total IgG | | | |
| N-Glycans | + | 18 | 0 |
| | - | 6 | 18 |

| | |
|---|---|
| Sensitivity | 75.0 % |
| Specificity | 100.0 % |
| PPV | 100.0 % |
| NPV | 75.0 % |
| False Positive Rate | 0.0 % |
| Accuracy | 85.7 % |

Fig. 14
CONTINUED

|            | Threshold Selected: | Sensitivity% | 95% CI | Specificity% | 95% CI | Likelihood ratio |
|------------|---------------------|--------------|--------|--------------|--------|------------------|
| F(6)A2G0   | < 11.30 | 61.11 | 38.62% to 79.69% | 88.89 | 67.20% to 98.03% | 5.5 |
|            | < 11.87 | 66.67 | 43.75% to 83.72% | 88.89 | 67.20% to 98.03% | 6 |
|            | < 12.33 | 72.22 | 49.13% to 87.50% | 88.89 | 67.20% to 98.03% | 6.5 |

|            | Threshold Selected: | Sensitivity% | 95% CI | Specificity% | 95% CI | Likelihood ratio |
|------------|---------------------|--------------|--------|--------------|--------|------------------|
| F(6)A2G2   | > 29.59 | 66.67 | 43.75% to 83.72% | 88.89 | 67.20% to 98.03% | 6 |
|            | > 29.66 | 66.67 | 43.75% to 83.72% | 94.44 | 74.24% to 99.72% | 12 |
|            | > 30.56 | 61.11 | 38.62% to 79.69% | 94.44 | 74.24% to 99.72% | 11 |
|            | > 31.24 | 55.56 | 33.72% to 75.44% | 94.44 | 74.24% to 99.72% | 10 |

Fig. 14
CONTINUED

|  | Threshold Selected: | Sensitivity% | 95% CI | Specificity% | 95% CI | Likelihood ratio |
|---|---|---|---|---|---|---|
| % Total Gal | >86.62 | 72.22 | 49.13% to 87.50% | 77.78 | 54.79% to 91.00% | 3.25 |
|  | >87.06 | 72.22 | 49.13% to 87.50% | 83.33 | 60.78% to 94.16% | 4.333 |
|  | >87.68 | 72.22 | 49.13% to 87.50% | 88.89 | 67.20% to 98.03% | 6.5 |
|  | >88.14 | 66.67 | 43.75% to 83.72% | 88.89 | 67.20% to 98.03% | 6 |

| Threshold Selected: | Sensitivity% | 95% CI | Specificity% | 95% CI | Likelihood ratio |
|---|---|---|---|---|---|
| >74.01 | 44.44 | 24.56% to 66.28% | 77.78 | 54.79% to 91.00% | 2 |
| >74.63 | 44.44 | 24.56% to 66.28% | 83.33 | 60.78% to 94.16% | 2.667 |
| >75.60 | 44.44 | 24.56% to 66.28% | 88.89 | 67.20% to 98.03% | 4 |
| >76.31 | 44.44 | 24.56% to 66.28% | 94.44 | 74.24% to 99.72% | 8 |

Fig. 14
CONTINUED

| | | | Acute vs Treated LD | | | | | | |
|---|---|---|---|---|---|---|---|---|---|
| | Direction | 100 | 0 | 100 | 100 | 0 | 0 | 0 | |
| | Rule: | 5.5 | 21.48 | 35.22 | 14.15 | 12.79 | 94.5 | 71.33 | Criteria |
| Error | ID | 1501 | 1647 | 1809 | 1850 | 2021 | %Fucosylation | %Digal (G2) | >4/7 |
| | Acute1 160 | 2.44 | 28.42 | 27.11 | 8.79 | 13.59 | 97.56 | 69.12 | N |
| | Acute1 161 | 3.55 | 25.74 | 26.67 | 11.90 | 13.84 | 96.45 | 66.24 | N |
| | Acute1 165 | 5.46 | 28.03 | 31.72 | 11.21 | 14.08 | 94.54 | 73.84 | N |
| | Acute1 167 | 2.14 | 26.87 | 31.07 | 14.06 | 14.08 | 97.86 | 72.03 | N |
| | Acute1 168 | 3.15 | 29.03 | 27.87 | 11.86 | 16.13 | 96.85 | 73.03 | N |
| | Acute1 169 | 5.12 | 24.16 | 30.05 | 14.24 | 16.26 | 94.88 | 70.47 | N |
| | Acute1 170 | 5.25 | 26.17 | 31.53 | 13.15 | 13.89 | 94.75 | 71.59 | N |
| | Acute1 171 | 3.30 | 27.47 | 31.75 | 11.67 | 17.30 | 96.70 | 76.52 | N |
| | Acute1 172 | 4.66 | 29.44 | 25.76 | 10.29 | 16.14 | 95.34 | 71.34 | N |
| | Acute1 183 | 2.85 | 28.89 | 32.86 | 8.96 | 15.64 | 97.15 | 77.39 | N |
| | Acute1 185 | 6.06 | 29.21 | 29.49 | 8.95 | 12.82 | 93.94 | 71.53 | N |
| | Acute1 186 | 3.93 | 28.72 | 33.61 | 8.55 | 15.62 | 96.07 | 77.95 | N |
| | Acute1 188 | 0.29 | 22.71 | 42.22 | 8.53 | 17.23 | 99.71 | 82.16 | N |
| | Acute1 189 | 2.13 | 30.83 | 32.64 | 9.59 | 14.48 | 97.87 | 77.94 | N |
| | Acute1 192 | 0.42 | 26.31 | 27.23 | 8.88 | 11.58 | 100.42 | 65.12 | N |
| | Acute1 640 | 2.46 | 24.82 | 34.79 | 11.22 | 17.95 | 97.54 | 77.56 | N |
| | Acute1 663 | 2.85 | 24.35 | 32.97 | 9.34 | 19.66 | 97.15 | 76.98 | N |
| | Acute1 673 | 0.10 | 19.78 | 41.90 | 12.94 | 20.27 | 99.90 | 81.95 | N |
| | Treated1 181 | 6.47 | 19.60 | 33.79 | 12.01 | 9.07 | 93.53 | 62.47 | Y |
| | Treated1 182 | 7.02 | 17.56 | 36.64 | 15.33 | 11.77 | 92.98 | 65.96 | Y |
| | Treated1 195 | 9.81 | 17.77 | 33.87 | 13.65 | 11.08 | 90.19 | 62.72 | Y |
| | Treated1 252 | 6.67 | 19.89 | 36.32 | 14.48 | 12.11 | 93.33 | 68.32 | Y |
| | Treated1 440 | 6.52 | 18.23 | 38.76 | 15.56 | 10.34 | 93.48 | 67.33 | Y |
| | Treated1 452 | 4.59 | 16.16 | 41.63 | 14.57 | 12.76 | 95.41 | 70.55 | Y |
| | Treated1 465 | 9.37 | 18.31 | 39.18 | 12.02 | 10.54 | 90.63 | 68.03 | Y |
| | Treated1 518 | 6.78 | 19.69 | 41.34 | 12.77 | 10.28 | 93.22 | 71.31 | Y |
| | Treated1 681 | 5.54 | 17.17 | 41.16 | 16.22 | 12.10 | 94.46 | 70.43 | Y |
| | Treated1 682 | 5.41 | 13.59 | 39.94 | 18.71 | 15.78 | 94.59 | 69.31 | Y |
| | Treated1 688 | 6.80 | 18.72 | 36.50 | 14.45 | 13.51 | 93.20 | 68.72 | Y |
| | Treated1 742 | 6.41 | 17.70 | 37.64 | 16.60 | 11.30 | 93.59 | 66.64 | Y |
| | Treated1 745 | 9.38 | 17.87 | 31.64 | 12.72 | 11.17 | 90.62 | 60.68 | Y |
| | Treated1 885 | 4.88 | 19.86 | 43.35 | 14.00 | 9.49 | 95.12 | 72.69 | Y |
| | Treated1 944 | 6.58 | 20.02 | 35.65 | 14.91 | 11.42 | 93.42 | 67.09 | Y |
| | Treated1 946 | 8.24 | 20.25 | 36.32 | 14.23 | 10.91 | 91.76 | 67.48 | Y |
| | Treated1 962 | 4.63 | 19.97 | 43.60 | 12.69 | 10.75 | 95.37 | 74.32 | Y |
| | Treated1 993 | 6.70 | 17.74 | 38.27 | 14.91 | 12.43 | 93.30 | 68.44 | Y |

Fig. 15

| Total IgG N-Glycans | | Gold Standard | |
|---|---|---|---|
| | | + | - |
| | + | 18 | 0 |
| | - | 0 | 18 |

| | | |
|---|---|---|
| Sensitivity | 100.0 | % |
| Specificity | 100.0 | % |
| PPV | 100.0 | % |
| NPV | 100.0 | % |
| False Positive Rate | 0.0 | % |
| Accuracy | 100.0 | % |

Fig. 15
CONTINUED

| Cut-Off Threshold | Sensitivity% | 95% CI | Sensitivity% | 95% CI | Likelihood ratio |
|---|---|---|---|---|---|
| > 5.185 | 83.33 | 60.78% to 94.16% | 83.33 | 60.78% to 94.16% | 5 |
| > 5.330 | 83.33 | 60.78% to 94.16% | 88.89 | 67.20% to 98.03% | 7.5 |
| > 5.435 | 77.78 | 54.79% to 91.00% | 88.89 | 67.20% to 98.03% | 7 |
| > 5.500 | 77.78 | 54.79% to 91.00% | 94.44 | 74.24% to 99.72% | 14 |
| > 5.800 | 72.22 | 49.13% to 87.50% | 94.44 | 74.24% to 99.72% | 13 |

| Cut-Off Threshold | Sensitivity% | 95% CI | Sensitivity% | 95% CI | Likelihood ratio |
|---|---|---|---|---|---|
| < 20.14 | 94.44 | 74.24% to 99.72% | 94.44 | 74.24% to 99.72% | 17 |
| < 21.06 | 100 | 82.41% to 100.0% | 94.44 | 74.24% to 99.72% | 18 |
| < 23.44 | 100 | 82.41% to 100.0% | 88.89 | 67.20% to 98.03% | 9 |

| Cut-Off Threshold | Sensitivity% | 95% CI | Sensitivity% | 95% CI | Likelihood ratio |
|---|---|---|---|---|---|
| >33.83 | 88.89 | 67.20% to 98.03% | 83.33 | 60.78% to 94.16% | 5.333 |
| >34.33 | 83.33 | 60.78% to 94.16% | 83.33 | 60.78% to 94.16% | 5 |
| >35.22 | 83.33 | 60.78% to 94.16% | 88.89 | 67.20% to 98.03% | 7.5 |
| >35.99 | 77.78 | 54.79% to 91.00% | 88.89 | 67.20% to 98.03% | 7 |
| >36.41 | 66.67 | 43.75% to 83.72% | 88.89 | 67.20% to 98.03% | 6 |
| >36.57 | 61.11 | 38.62% to 79.69% | 88.89 | 67.20% to 98.03% | 5.5 |

Fig. 15
CONTINUED

| Cut-Off Threshold | Sensitivity% | 95% CI | Sensitivity% | 95% CI | Likelihood ratio |
|---|---|---|---|---|---|
| >12.86 | 72.22 | 49.13% to 87.50% | 77.78 | 54.79% to 91.00% | 3.25 |
| >13.05 | 72.22 | 49.13% to 87.50% | 83.33 | 60.78% to 94.16% | 4.333 |
| >13.40 | 72.22 | 49.13% to 87.50% | 88.89 | 67.20% to 98.03% | 6.5 |
| >13.83 | 66.67 | 43.75% to 83.72% | 88.89 | 67.20% to 98.03% | 6 |
| >14.03 | 61.11 | 38.62% to 79.69% | 88.89 | 67.20% to 98.03% | 5.5 |
| >14.15 | 61.11 | 38.62% to 79.69% | 94.44 | 74.24% to 99.72% | 11 |
| >14.24 | 55.56 | 33.72% to 75.44% | 94.44 | 74.24% to 99.72% | 10 |

| Cut-Off Threshold | Sensitivity% | 95% CI | Sensitivity% | 95% CI | Likelihood ratio |
|---|---|---|---|---|---|
| <12.27 | 77.78 | 54.79% to 91.00% | 94.44 | 74.24% to 99.72% | 14 |
| <12.60 | 83.33 | 60.78% to 94.16% | 94.44 | 74.24% to 99.72% | 15 |
| <12.79 | 88.89 | 67.20% to 98.03% | 94.44 | 74.24% to 99.72% | 16 |
| <13.17 | 88.89 | 67.20% to 98.03% | 88.89 | 67.20% to 98.03% | 8 |
| <13.55 | 94.44 | 74.24% to 99.72% | 88.89 | 67.20% to 98.03% | 8.5 |

| Cut-Off Threshold | Sensitivity% | 95% CI | Sensitivity% | 95% CI | Likelihood ratio |
|---|---|---|---|---|---|
| <94.20 | 72.22 | 49.13% to 87.50% | 94.44 | 74.24% to 99.72% | 13 |
| <94.50 | 77.78 | 54.79% to 91.00% | 94.44 | 74.24% to 99.72% | 14 |
| <94.57 | 77.78 | 54.79% to 91.00% | 88.89 | 67.20% to 98.03% | 7 |
| <94.67 | 83.33 | 60.78% to 94.16% | 88.89 | 67.20% to 98.03% | 7.5 |

Fig. 15
CONTINUED

| Cut-Off Threshold | Sensitivity% | 95% CI | Sensitivity% | 95% CI | Likelihood ratio |
|---|---|---|---|---|---|
| <70.93 | 83.33 | 60.78% to 94.16% | 77.78 | 54.79% to 91.00% | 3.75 |
| <71.33 | 88.89 | 67.20% to 98.03% | 77.78 | 54.79% to 91.00% | 4 |
| <71.44 | 88.89 | 67.20% to 98.03% | 72.22 | 49.13% to 87.50% | 3.2 |
| <71.56 | 88.89 | 67.20% to 98.03% | 66.67 | 43.75% to 83.72% | 2.667 |

Fig. 15
CONTINUED

| Error | Control vs Treated LD | | | |
|---|---|---|---|---|
| | Direction | | 0 | 100 |
| | Rule | | 20.4 | 31.52 |
| | ID | | 1647 | 1809 | >2/2 |
| | Ctrl1 138 | | 27.41 | 21.56 | N |
| | Ctrl1 159 | | 28.79 | 26.29 | N |
| | Ctrl1 162 | | 30.67 | 23.06 | N |
| | Ctrl1 163 | | 27.93 | 28.67 | N |
| | Ctrl1 164 | | 26.21 | 25.48 | N |
| | Ctrl1 166 | | 30.75 | 24.95 | N |
| | Ctrl1 173 | | 26.51 | 29.65 | N |
| | Ctrl1 174 | | 23.94 | 26.57 | N |
| | Ctrl1 175 | | 27.58 | 27.61 | N |
| | Ctrl1 176 | | 26.86 | 20.83 | N |
| | Ctrl1 177 | | 30.20 | 31.40 | N |
| | Ctrl1 184 | | 32.59 | 28.77 | N |
| | Ctrl1 187 | | 32.25 | 29.53 | N |
| | Ctrl1 190 | | 28.45 | 28.07 | N |
| | Ctrl1 191 | | 20.96 | 27.20 | N |
| | Ctrl1 515 | | 32.50 | 27.58 | N |
| | Ctrl1 526 | | 31.00 | 28.58 | N |
| | Ctrl1 538 | | 30.64 | 26.07 | N |
| | Treated1 181 | | 19.60 | 33.78 | Y |
| | Treated1 182 | | 17.56 | 36.64 | Y |
| | Treated1 195 | | 17.77 | 33.87 | Y |
| | Treated1 252 | | 19.89 | 36.32 | Y |
| | Treated1 440 | | 18.23 | 38.76 | Y |
| | Treated1 452 | | 16.16 | 41.63 | Y |
| | Treated1 465 | | 18.31 | 39.18 | Y |
| | Treated1 518 | | 19.69 | 41.34 | Y |
| | Treated1 681 | | 17.17 | 41.16 | Y |
| | Treated1 682 | | 13.59 | 39.94 | Y |
| | Treated1 688 | | 18.72 | 36.50 | Y |
| | Treated1 742 | | 17.70 | 37.64 | Y |
| | Treated1 745 | | 17.87 | 31.64 | Y |
| | Treated1 885 | | 19.86 | 43.35 | Y |
| | Treated1 944 | | 20.02 | 35.65 | Y |
| | Treated1 946 | | 20.25 | 36.32 | Y |
| | Treated1 962 | | 19.97 | 43.60 | Y |
| | Treated1 993 | | 17.74 | 38.27 | Y |

Fig. 16

| Total Ig G | | Gold Standard | |
|---|---|---|---|
| N-Glycans | | + | - |
| | + | 18 | 0 |
| | - | 0 | 18 |

| | | |
|---|---|---|
| Sensitivity | 100.0 | % |
| Specificity | 100.0 | % |
| PPV | 100.0 | % |
| NPV | 100.0 | % |
| False Positive Rate | 0.0 | % |
| Accuracy | 100.0 | % |

Fig. 16
CONTINUED

| Cut-Off Threshold | Sensitivity% | 95% CI | Specificity % | 95% CI | Likelihood ratio |
|---|---|---|---|---|---|
| <20.14 | 94.44 | 74.24% to 99.72% | 100 | 82.41% to 100.0% | |
| <20.61 | 100 | 82.41% to 100.0% | 100 | 82.41% to 100.0% | |
| <22.45 | 100 | 82.41% to 100.0% | 94.44 | 74.24% to 99.72% | 18 |
| <25.08 | 100 | 82.41% to 100.0% | 88.89 | 67.20% to 98.03% | 9 |

| Cut-Off Threshold | Sensitivity% | 95% CI | Specificity % | 95% CI | Likelihood ratio |
|---|---|---|---|---|---|
| >30.53 | 100 | 82.41% to 100.0% | 94.44 | 74.24% to 99.72% | 18 |
| >31.52 | 100 | 82.41% to 100.0% | 100 | 82.41% to 100.0% | |
| >32.72 | 94.44 | 74.24% to 99.72% | 100 | 82.41% to 100.0% | |
| >33.83 | 88.89 | 67.20% to 98.03% | 100 | 82.41% to 100.0% | |

Fig. 16
CONTINUED

| Sample ID | Classification | Age | Sex | Ethnicity | Site Location | Abx Prescribed | Post-Treatment Sample | Pilot Study | N=18 Study |
|---|---|---|---|---|---|---|---|---|---|
| Ctrl 184 | Control (- Serology) | 23 | Male | White | East Hampton | NA | NA | NA | YES |
| Ctrl 166 | Control (- Serology) | 26 | Male | White | Wisconsin | NA | NA | NA | YES |
| Ctrl 187 | Control (- Serology) | 30 | Female | White | Wisconsin | NA | NA | NA | YES |
| Ctrl 190 | Control (- Serology) | 46 | Male | Hispanic or Latino | East Hampton | NA | NA | NA | YES |
| Ctrl 159 | Control (- Serology) | 47 | Male | White | East Hampton | NA | NA | NA | YES |
| Ctrl 176 | Control (- Serology) | 53 | Male | White | Wisconsin | NA | NA | NA | YES |
| Ctrl 173 | Control (- Serology) | 53 | Female | White | East Hampton | NA | NA | NA | YES |
| Ctrl 163 | Control (- Serology) | 59 | Male | White | East Hampton | NA | NA | NA | YES |
| Ctrl 138 | Control (- Serology) | 59 | Male | White | Wisconsin | NA | NA | NA | YES |
| Ctrl 162 | Control (- Serology) | 62 | Male | White | East Hampton | NA | NA | NA | YES |
| Ctrl 177 | Control (- Serology) | 62 | Male | Hispanic or Latino | East Hampton | NA | NA | NA | YES |
| Ctrl1174 | Control (- Serology) | 64 | Female | White | East Hampton | NA | NA | NA | YES |
| Ctrl 164 | Control (- Serology) | 68 | Female | White | East Hampton | NA | NA | NA | YES |
| Ctrl 175 | Control (- Serology) | 72 | Female | White | East Hampton | NA | NA | NA | YES |
| Ctrl 191 | Control (- Serology) | 79 | Female | White | East Hampton | NA | NA | NA | YES |
| Ctrl 515 | Control (- Serology) | 27 | Male | Hispanic or Latino | Long Island | NA | NA | Pilot | YES |
| Ctrl 538 | Control (- Serology) | 49 | Female | Hispanic or Latino | Long Island | NA | NA | Pilot | YES |
| Ctrl 526 | Control (- Serology) | 59 | Male | White | Long Island | NA | NA | Pilot | YES |
| Ctrl 610 | Control (- Serology) | 65 | Male | White | Long Island | NA | NA | Pilot | NA |

Fig. 17

| Sample ID | Classification | Age | Sex | Ethnicity | Site Location | Abx Prescribed | Post-Treatment Sample | Pilot Study | N=18 Study |
|---|---|---|---|---|---|---|---|---|---|
| Ctrl 611 | Control (- Serology) | 53 | Female | White | Long Island | NA | NA | Pilot | NA |
| Ctrl 664 | Control (- Serology) | 36 | Female | Hispanic or Latino | Long Island | NA | NA | Pilot | NA |
| Ctrl 674 | Control (- Serology) | 36 | Male | White | Long Island | NA | NA | Pilot | NA |
| Acute 183 | Confirmed Lyme | 27 | Male | White | East Hampton | 14 days doxy | YES | NA | YES |
| Acute 185 | Confirmed Lyme | 33 | Male | White | Wisconsin | 14 days doxy | YES | NA | YES |
| Acute 186 | Confirmed Lyme | 34 | Female | White | Wisconsin | 14 days doxy | YES | NA | YES |
| Acute 168 | Confirmed Lyme | 46 | Male | White | East Hampton | 14 days doxy | YES | NA | YES |
| Acute 160 | Confirmed Lyme | 52 | Male | White | East Hampton | 21 days doxy | YES | NA | YES |
| Acute 171 | Confirmed Lyme | 53 | Female | White | East Hampton | 21 days doxy | YES | NA | YES |
| Acute 192 | Confirmed Lyme | 54 | Male | Hispanic or Latino | East Hampton | 14 days amoxill | YES | NA | YES |
| Acute 189 | Confirmed Lyme | 54 | Male | Hispanic or Latino | East Hampton | 20 days doxy | YES | NA | YES |
| Acute 161 | Confirmed Lyme | 58 | Male | White | East Hampton | 21 days doxy | YES | NA | YES |
| Acute 172 | Confirmed Lyme | 62 | Female | White | East Hampton | 14 days doxy | YES | NA | YES |
| Acute 188 | Confirmed Lyme | 62 | Male | White | Wisconsin | 14 days doxy | YES | NA | YES |
| Acute 169 | Confirmed Lyme | 73 | Female | White | East Hampton | 14 days doxy | YES | NA | YES |
| Acute 170 | Confirmed Lyme | 74 | Female | White | East Hampton | 14 days amoxill | YES | NA | YES |
| Acute 167 | Confirmed Lyme | 75 | Female | White | East Hampton | 10 days amoxill | YES | NA | YES |
| Acute 165 | Confirmed Lyme | 47 | Male | White | Wisconsin | 14 days doxy | YES | NA | YES |
| Acute 663 | Confirmed Lyme | 43 | Male | Hispanic or Latino | Long Island | 20 days doxy | YES | Pilot | YES |

Fig. 17
CONTINUED

| Sample ID | Classification | Age | Sex | Ethnicity | Site Location | Abx Prescribed | Post-Treatment Sample | Pilot Study | N=18 Study |
|---|---|---|---|---|---|---|---|---|---|
| Acute 640 | Confirmed Lyme | 49 | Female | White | Long Island | 21 days doxy | YES | Pilot | YES |
| Acute 673 | Confirmed Lyme | 65 | Male | White | Long Island | 14 days doxy | YES | Pilot | YES |
| Acute 585 | Confirmed Lyme | 64 | Male | White | Long Island | 14 days doxy | NA | Pilot | NA |
| Acute 677 | Confirmed Lyme | 36 | Female | Hispanic or Latino | Long Island | 14 days amoxill | NA | Pilot | NA |

Fig. 17
CONTINUED

| Bb Serology of Pilot Study | | | |
|---|---|---|---|
| ID | C6 | WB IgM | WB IgG |
| C - 515 | – | – | IT |
| C - 526 | – | IT | – |
| C - 538 | – | IT | IT |
| C - 610 | – | IT | – |
| C - 611 | – | IT | IT |
| C - 664 | – | – | IT |
| C - 674 | – | IT | IT |
| A - 585 | + | + | IT |
| A - 677 | + | IT | + |
| A - 640 | + | – | + |
| A - 663 | + | + | IT |
| A - 673 | + | + | + |
| Tr - 640 | + | IT | + |
| Tr - 663 | + | + | IT |
| Tr - 673 | + | + | IT |

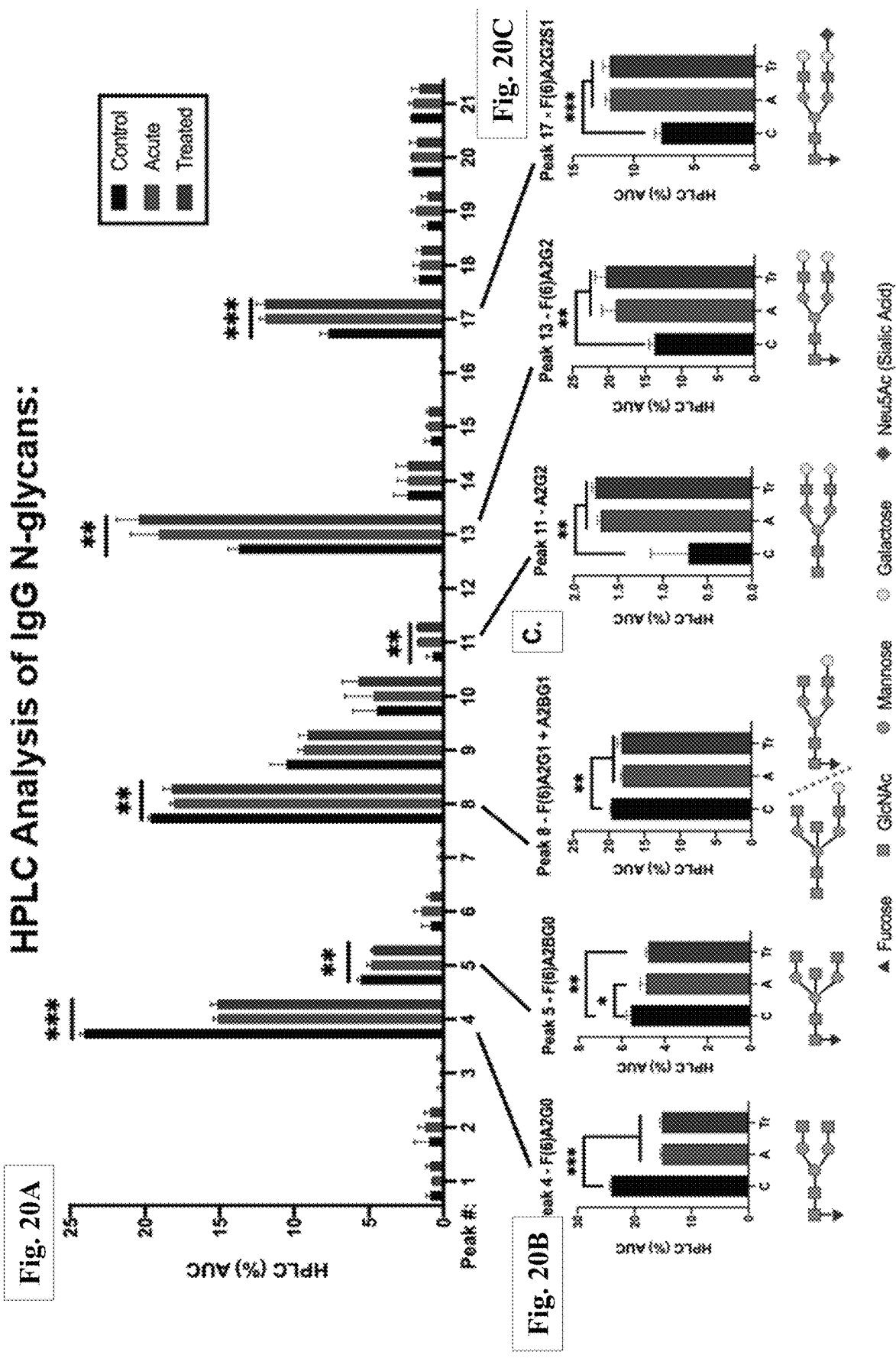

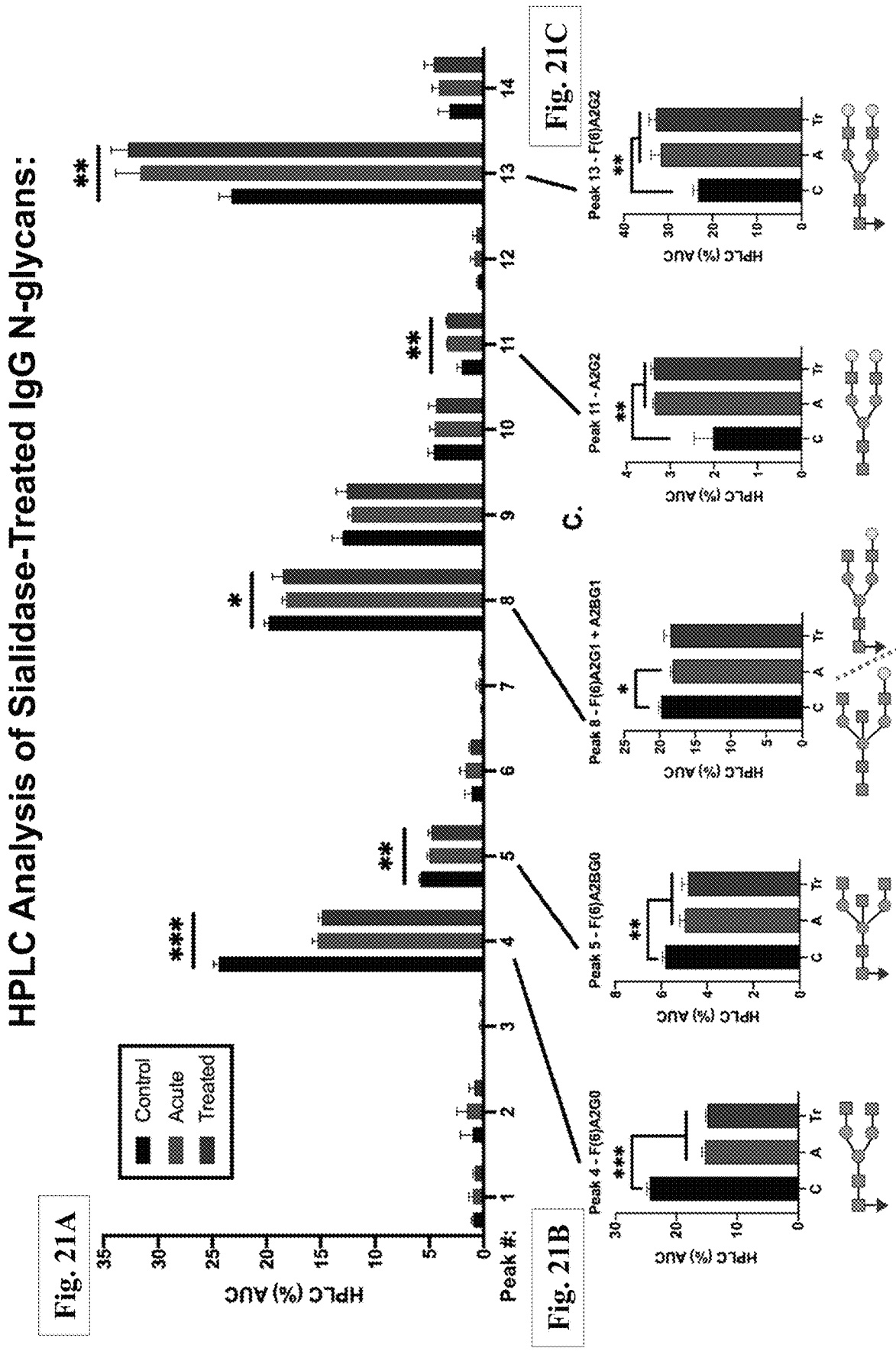

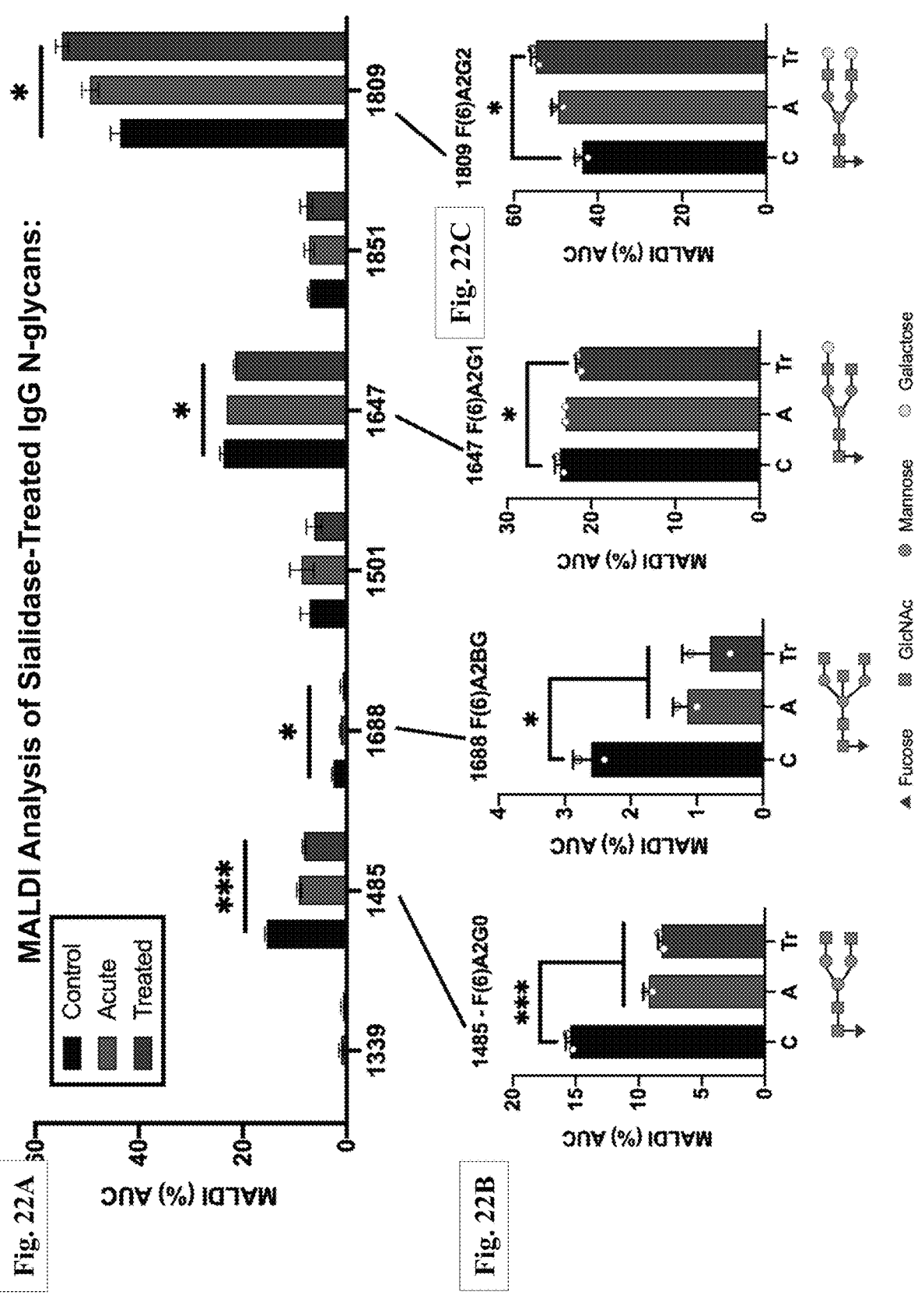

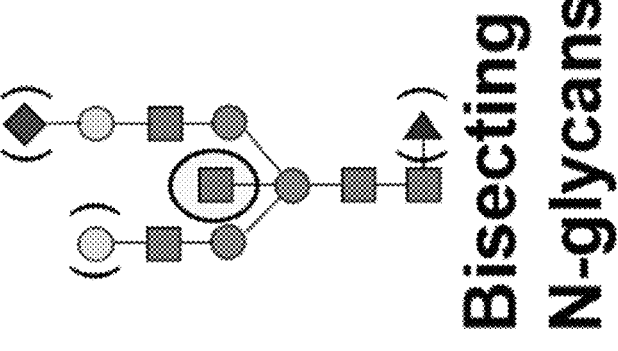
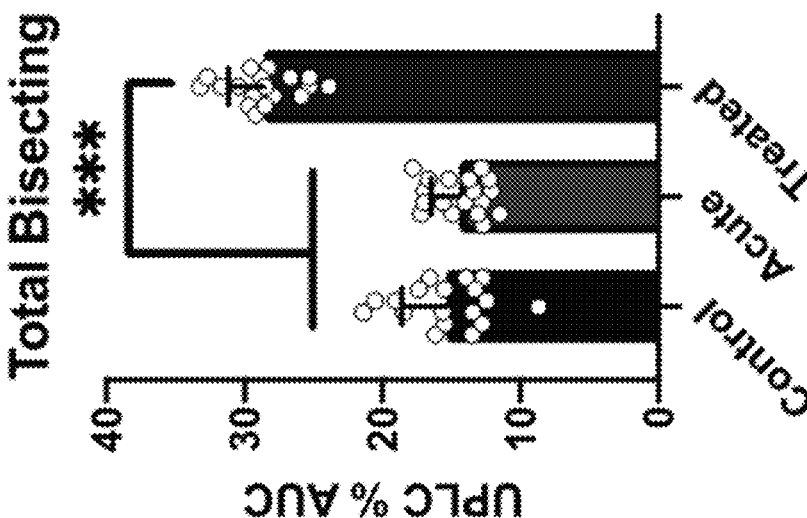
Statistical analysis: One-Way ANOVA using Tukey's multiple comparisons test, BALF n=18 per cohort
Fig. 29

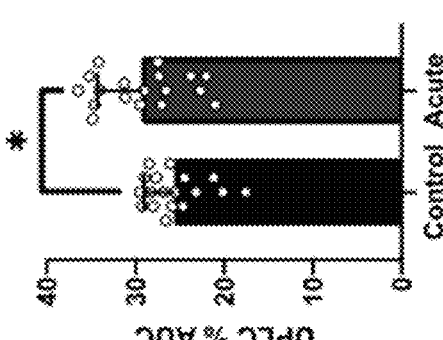
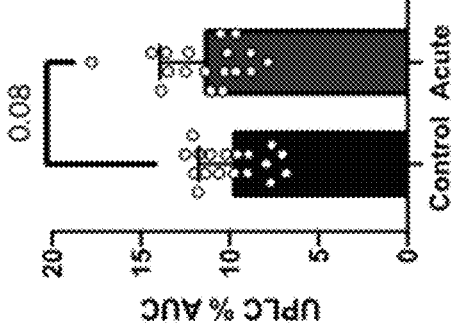
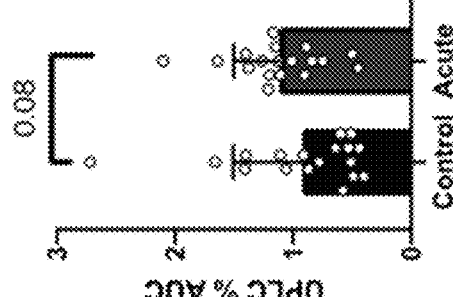
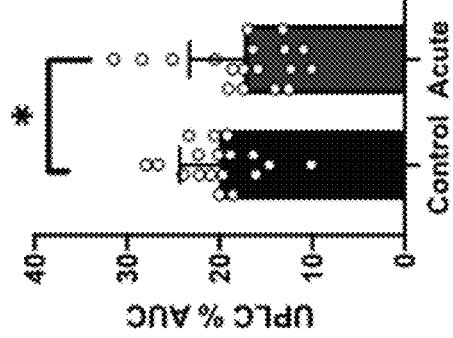
Fig. 30

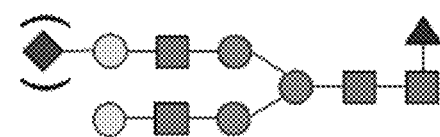
Total Di-galactose
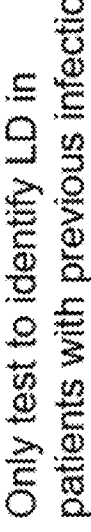
Only test to identify LD in patients with previous infection
Fig. 32

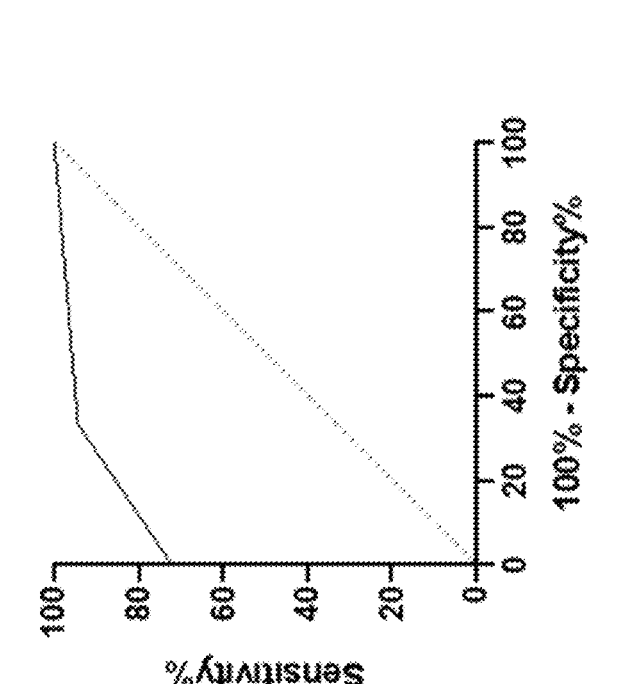
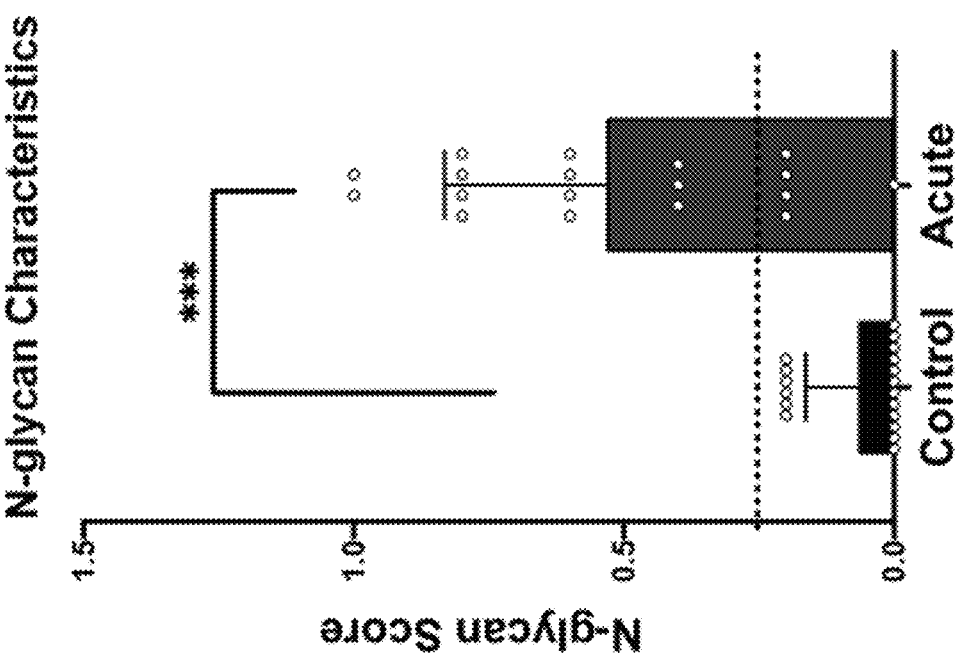
Fig. 37

METHODS OF DIAGNOSING OR TREATING LYME DISEASE

CROSS-REFERENCE TO RELATED APPLICATIONS

The present application is a continuation of PCT International Patent Application No. PCT/US2022/047442, filed Oct. 21, 2022, which claims priority under 35 U.S.C. § 119 (e) to U.S. Provisional Patent Application No. 63/270,439, filed Oct. 21, 2021, all of which is are incorporated herein by reference in their entireties.

BACKGROUND

There are 329,000 cases of Lyme disease (LD) each year in the US. LD is diagnosed through a two-tier assay of serological reactivity towards *Borrelia burgdorferi* (Bb) antigens. This testing system has a low sensitivity of 46% and a specificity of 99%. Testing is highly dependent on the presence of an erythema migrans skin lesion (EM) that is seen in only 70-80% of patients and is often difficult to detect on darker skin pigmentation. For those without EM presentation, diagnosis is almost impossible. When LD is not treated within the acute phase, the spirochete can disseminate into synovial, cardiac, and neuronal tissue—making eradication challenging. A subset of patients suffers from Post-Treatment Lyme Disease Syndrome (PTLDS), which is poorly elucidated due to a lack of diagnostic tools. Pregnant women who are acutely infected with *Borellia* and do not receive treatment have experienced multiple adverse pregnancy outcomes, including preterm delivery, stillbirth and congenital cardiac malformations. Finally, infection does not create immunity to future infections. The current method is unable to determine if an infection is a new infection, or the patient is positive due to a previous infection.

Lyme disease cases is continued to increase and are expected to worsen with the impact of climate change creating more favorable environmental conditions. The advantage of this method is not only improved sensitivity for diagnosis, but also the ability to track disease resolution and to differentiate between new and old infections.

Therefore, there is a need for effective Lyme disease diagnostic methods and treatment methods. The present disclosure addresses this need.

BRIEF SUMMARY

In some aspects, the present disclosure is directed to the following non-limiting embodiments.

In certain embodiments, the present disclosure provides a method of diagnosing Lyme disease in a subject. In certain embodiments, the method comprises determining a glycosylation profile of a protein in the subject. In certain embodiments, a change of the glycosylation profile of the protein relative to a normal glycosylation profile is associated with Lyme disease. In certain embodiments, the method comprises comparing the glycosylation profile of the protein in the subject with a predetermined first glycosylation profile indicating free of Lyme disease or a predetermined second glycosylation profile indicating Lyme disease.

In certain embodiments, the present disclosure provides a method of treating and/or ameliorating Lyme disease in a subject. In certain embodiments, the method comprises determining a glycosylation profile of a protein in the subject. In certain embodiments, a change of the glycosylation profile of the protein in relative to a normal glycosylation profile is associated with Lyme disease. In certain embodiments, the method comprises comparing the glycosylation profile of the protein in the subject with a predetermined first glycosylation profile indicating free of Lyme disease or a predetermined second glycosylation profile indicating Lyme disease. In certain embodiments, if the glycosylation profile of the protein in the subject does not correspond to the first glycosylation profile or the glycosylation profile of the protein in the subject correspond to the second predetermined level, the method comprises administering to the subject an effective amount of compound effective for treating and/or ameliorating Lyme disease.

In certain embodiments, the present disclosure provides a method of evaluating a treatment of Lyme disease. In certain embodiments, the method comprises determining a glycosylation profile of a protein in the subject after the subject has been diagnosed with and received treatment for Lyme disease. In certain embodiments, the method comprises comparing the glycosylation profile of the protein in the subject with a predetermined glycosylation profile indicating a state of recovering from Lyme disease. In certain embodiments, the method comprises comparing the glycosylation profile of the protein in the subject with a predetermined glycosylation profile indicating recovered from Lyme disease. In certain embodiments, the method comprises comparing the glycosylation profile of the protein in the subject with a predetermined glycosylation profile indicating neither recovering nor recovered.

BRIEF DESCRIPTION OF THE DRAWINGS

The following detailed description of exemplary embodiments will be better understood when read in conjunction with the appended drawings. For the purpose of illustrating, non-limiting embodiments are shown in the drawings. It should be understood, however, that the instant specification is not limited to the precise arrangements and instrumentalities of the embodiments shown in the drawings.

FIGS. 3A-3B describe certain aspects of the relationships between disease state and recovery N-glycan biomarkers, in accordance with some embodiments. FIG. 3A: IgG N-glycan profiles identify Primary Acute LD and Acute LD in patients with a previous history of LD. Fucosylated, digalactose (G2) content from IgG was summed from the UPLC-ESI-MS data and compared between healthy endemic controls, EM (+) STTT (+) Acute LD patients without a history of Lyme disease, and EM (+) STTT (+) patients with a history of previous Lyme disease infection. Control n=18, Acute $1^{st}$ Infection n=9, Acute with Previous Infection n=9, standard error of the mean presented. FIG.

3B: IgG N-glycan profiles identify biomarkers of successful LD Treatment. Total bisecting content from IgG N-glycans was summed from the UPLC-ESI-MS data and compared between healthy endemic controls, EM (+) STTT (+) Acute LD patients, and the same acute LD patients following 10-21 days of doxycycline antibiotics and 70-90 days of convalescence. The bisecting N-glycan structure is presented with a yellow highlighted circle highlighting the bisecting GlcNAc sugar. Control n=18, Acute n=18, Treated n=18, standard deviation error bars presented. Data presented are derived from the Bay Area Lyme Foundation serum set. Respective N-glycan structures are presented to the left with parenthesis around variable regions of the N-glycan. Statistical analysis was performed using One-way ANOVA with Tukey's multiple comparisons test, p<0.01, *p<0.001. AUC=Area Under the Curve from the chromatogram.

Figures 4A, 4B:
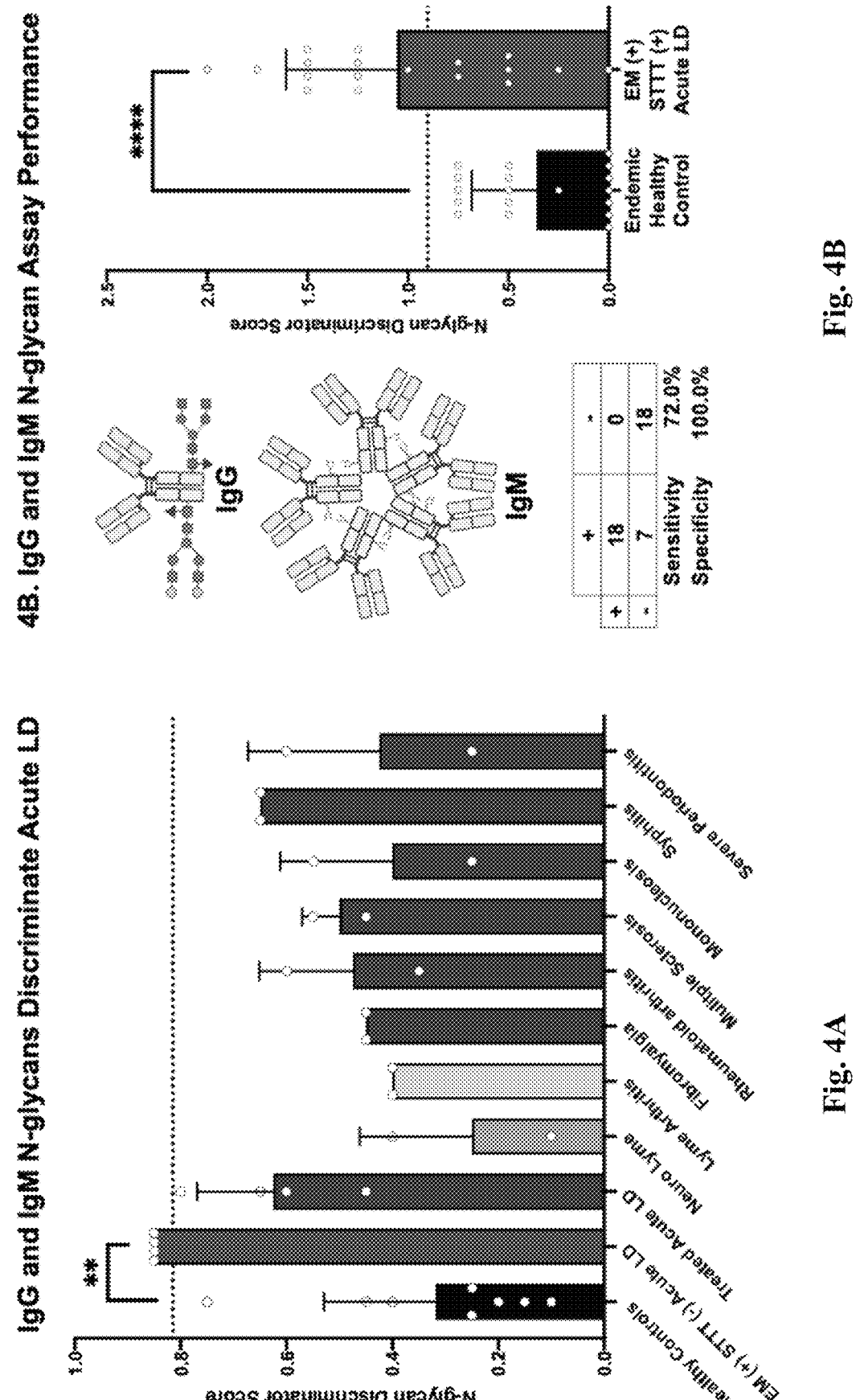

FIGS. 4A-4B demonstrate that IgG and IgM N-glycan profiles discriminate acute Lyme disease from other diseases. FIG. 4A: IgG and IgM combined N-glycans identify EM (+) STTT (−) Early Acute Lyme disease. N-glycans from total IgG and IgM that discriminate between seronegative acute LD and all other diseases assayed were combined into a single score and summed from the UPLC-ESI-MS data. Data is derived from the CDC Panel 1 serum set. Healthy Control n=8, EM (+) STTT (−) Acute LD n=4, Treated Acute Lyme disease n=4, Neuro Lyme n=2, Lyme Arthritis n=2, Fibromyalgia n=2, Rheumatoid Arthritis n=2, Multiple Sclerosis n=2, Mononucleosis n=2, Syphilis n=2, Severe Periodontitis n=2. FIG. 4B: IgG and IgM N-glycan profiles combined identify EM (+) STTT (+) Acute Lyme disease. Endemic healthy Control n=18, EM (+) STTT (+) Acute LD n=18. The dotted lines represent the final score cut-off between positive and negative Acute Lyme disease. Data is derived from the Bay Area Lyme disease Foundation serum set. To the left, glycosylated IgG and IgM are presented along with a summary confusion matrix displaying sensitivity and specificity. Standard deviation error bars are presented. Statistical analysis was performed using One-way ANOVA with Tukey's multiple comparisons test, p<0.01, **p<0.0001.

FIG. 5: altered IgG N-glycan profiles are detected in inflammatory diseases. As shown in FIG. 5, in general, inflammatory diseases have serum IgG with N-glycan alterations that promote a pro-inflammatory signaling cascade due to a reduction in terminal galactose and sialic acid.

FIG. 6: patient samples used in the present study. Healthy Control and Lyme disease LD with matched Acute and Post-treatment Demographics of Bay Area Lyme Disease Biobank Serum Samples. Sample ID numbers are linked to demographic details including age, sex, ethnicity, and if the patient donated a post-treatment convalescent serum sample.

Figure 7A:
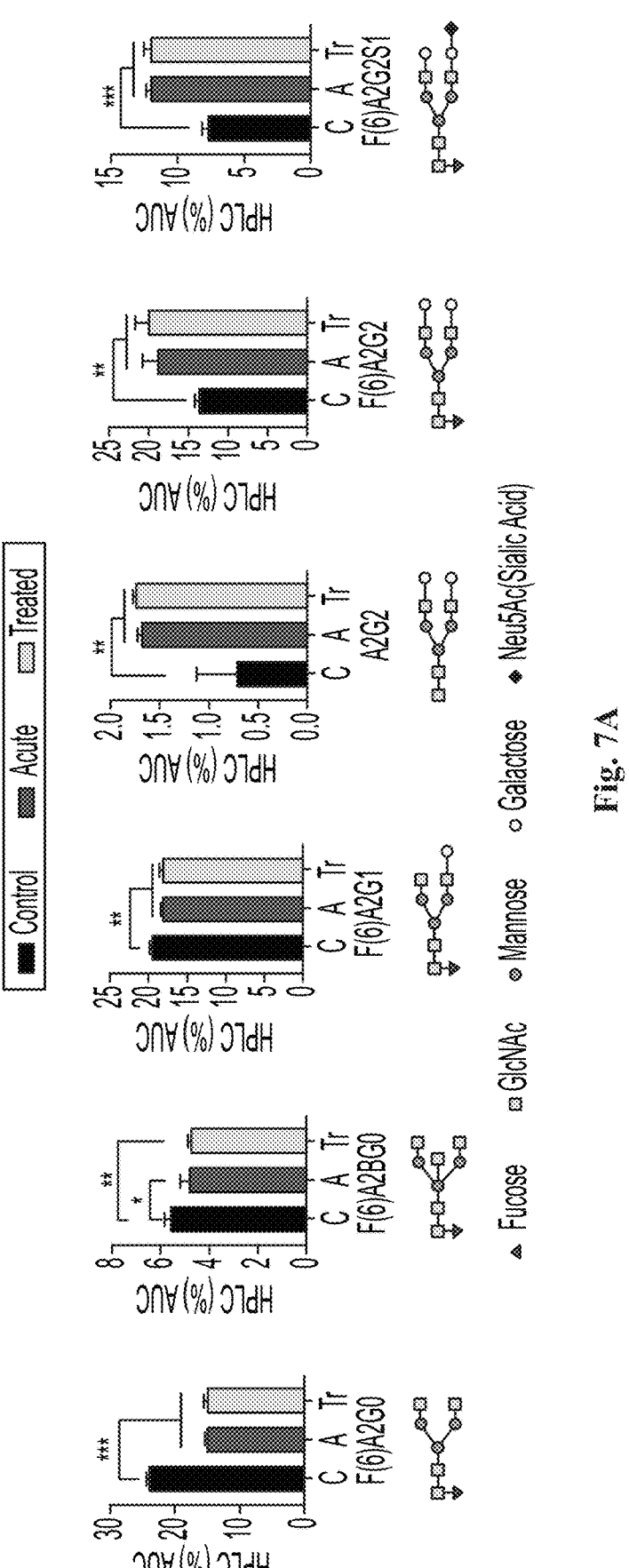
Figure 7B:
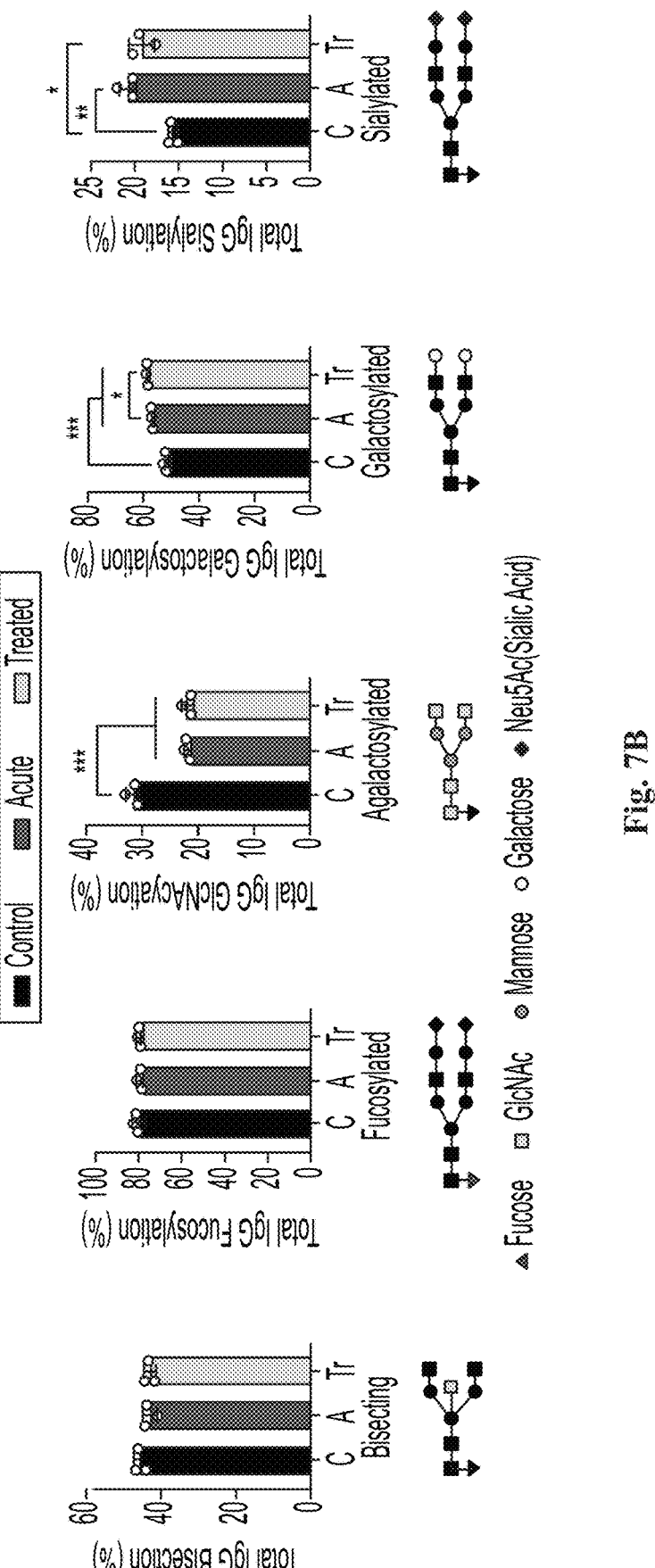

FIGS. 7A-7B: Analysis of IgG reveals significant changes in N-glycan structure distribution during acute and treated LD, in accordance with some embodiments. FIG. 7A: Significant alterations of IgG N-glycans reported by HPLC analysis from pooled serum from control (C), acute (A), or treated (Tr) patients reported as the percent area under the curve (AUC) for each peak determined from the average of triplicate samples. N-glycan structures are displayed below. Control represents pooled healthy age-matched serum n=7, Acute represents pooled serum from two-tiered diagnosed Lyme disease patients n=5, Treated represents patients donating serum a second time 70-90 days after completion of the reportedly curative round of antibiotic treatment (14-21 d doxycycline) for Lyme disease n=3. FIG. 7B: Labeled N-glycan classes: Bisecting, Fucosylated, Agalactosylated, Galactosylated, Sialylated detected using HPLC analysis of IgG N-glycans from 3 replicates+/−S.D. Analysis was completed using One-Way ANOVA with post-hoc Tukey's multiple comparisons, *p<0.05, p<0.01, *p<0.001.

FIGS. 8A-8B: Grouping IgG N-glycans by class reveals MALDI and HPLC detect similar trends during LD (FIG. 8A) Labeled N-glycan classes: Bisecting, Fucosylated, Agalactosylated, Galactosylated, Sialylated detected using HPLC analysis of desialylated IgG N-glycans grouped by class averaged from 3 replicates of pooled cohorts described in FIGS. 7A-7B. FIG. 8B: MALDI analysis of desialylated IgG N-glycan classes averaged from 2 replicates of pooled cohorts described in FIGS. 7A-7B. Analysis was completed using One-Way ANOVA with post-hoc Tukey's multiple comparisons, p<0.01, *p<0.001.

Figure 9A:
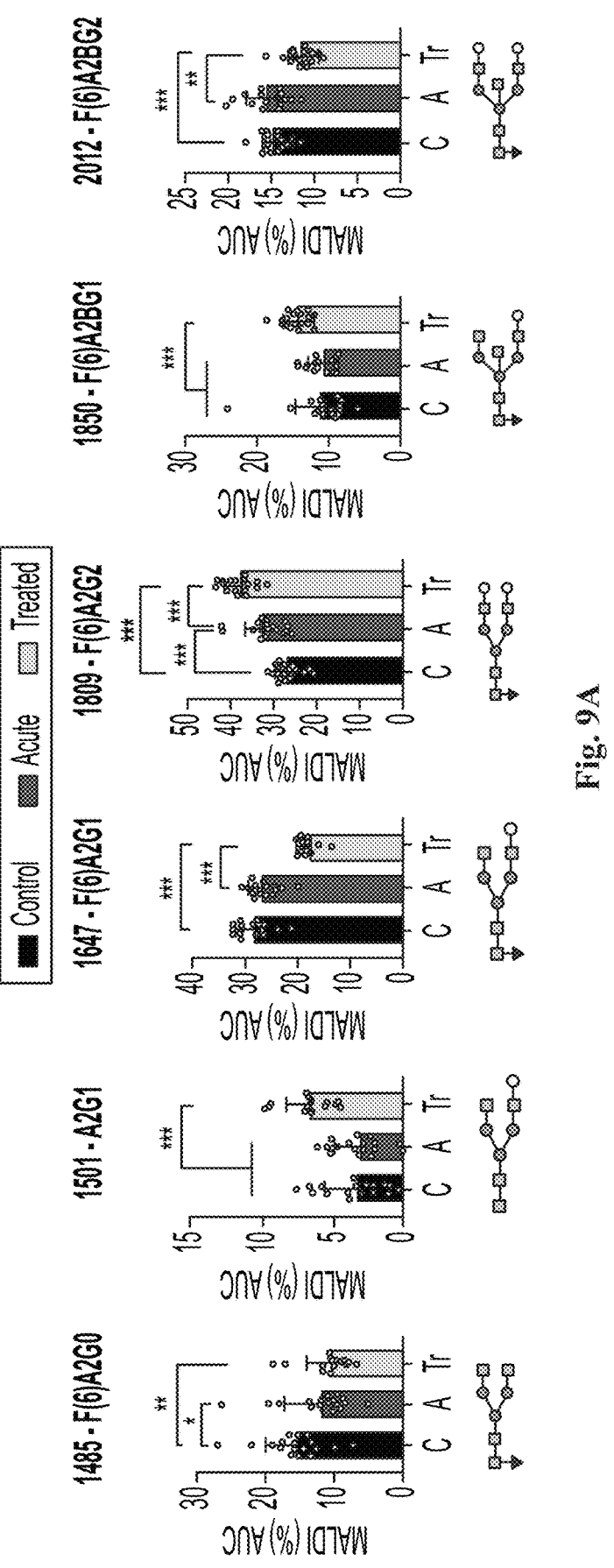
Figure 9B:
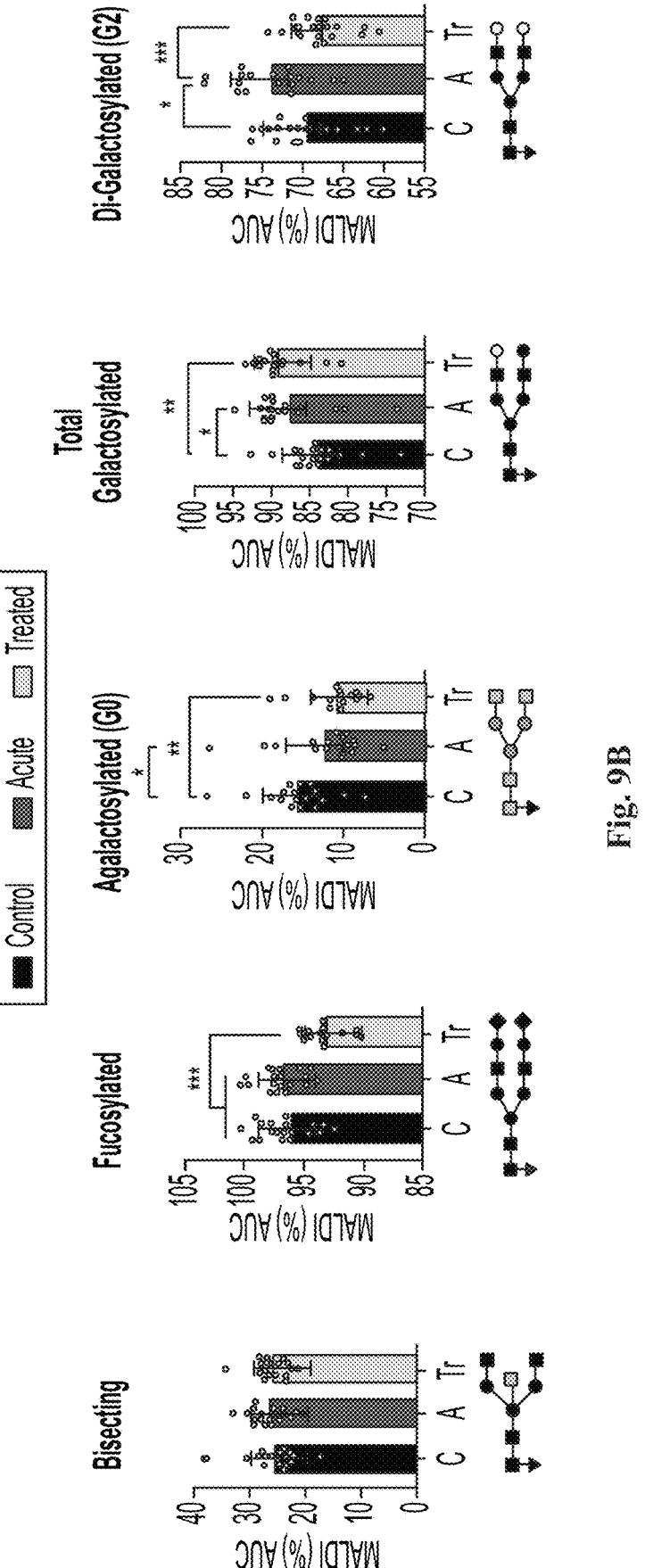

FIGS. 9A-9B: Confirmatory set of LD patient serum assayed using the high-throughput MALDI method (FIG. 9A) IgG N-glycans detected by MALDI analysis of Ab-captured IgG from n=18 cohorts individually run in triplicate+/−S.D. and reported as the percent of the total identified N-glycan m/z peak intensity. N-glycan structures displayed below (FIG. 9B) MALDI analysis of desialylated IgG N-glycans grouped by class from n=18 samples per cohort averaged in triplicate+/−S.D. Labeled N-glycan class structures: Bisecting, Fucosylated, Agalactosylated, Galactosylated, and Di-Galactosylated are presented below the respective graph. Analysis was completed using One-Way ANOVA with post-hoc Tukey's multiple comparisons, *p<0.05, p<0.01, *p<0.001.

FIG. 10: Confusion matrices from combined discriminatory IgG N-glycan ROC thresholds, in accordance with some embodiments. N-glycans with significant discrimination between cohorts determined using ROC analysis are listed above. The listed N-glycan discriminators were combined for each cohort comparison (Control vs Acute LD, Control vs Treated LD, Treated vs Acute LD) and the resulting confusion matrices are reported.

Figure 11:
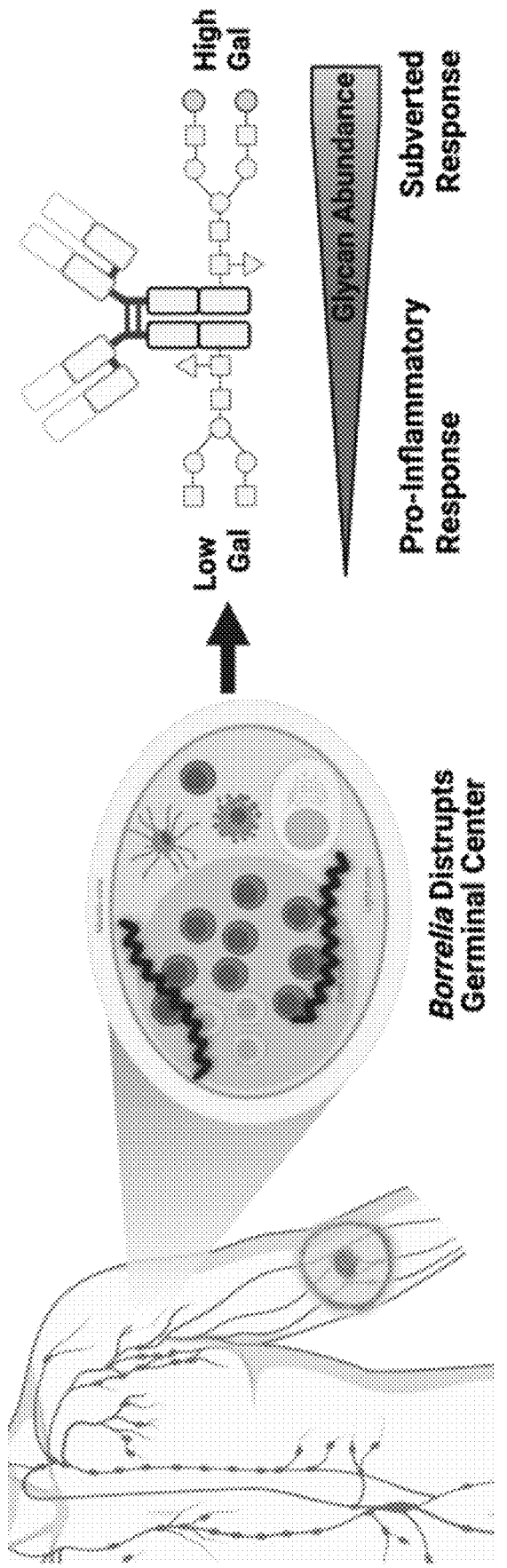

FIG. 11: IgG N-glycans Respond to acute Lyme disease infection with increased galactose, impairing bound IgG to signal for inflammation, unlike other pro-inflammatory disease IgG signatures, in accordance with some embodiments. Left to right, a tick infected with *Borrelia* transmits the infection to the human host leading to LD. The Bb spirochete disrupts the architecture of the germinal center within the lymph node. IgG molecules produced.

Figure 12:
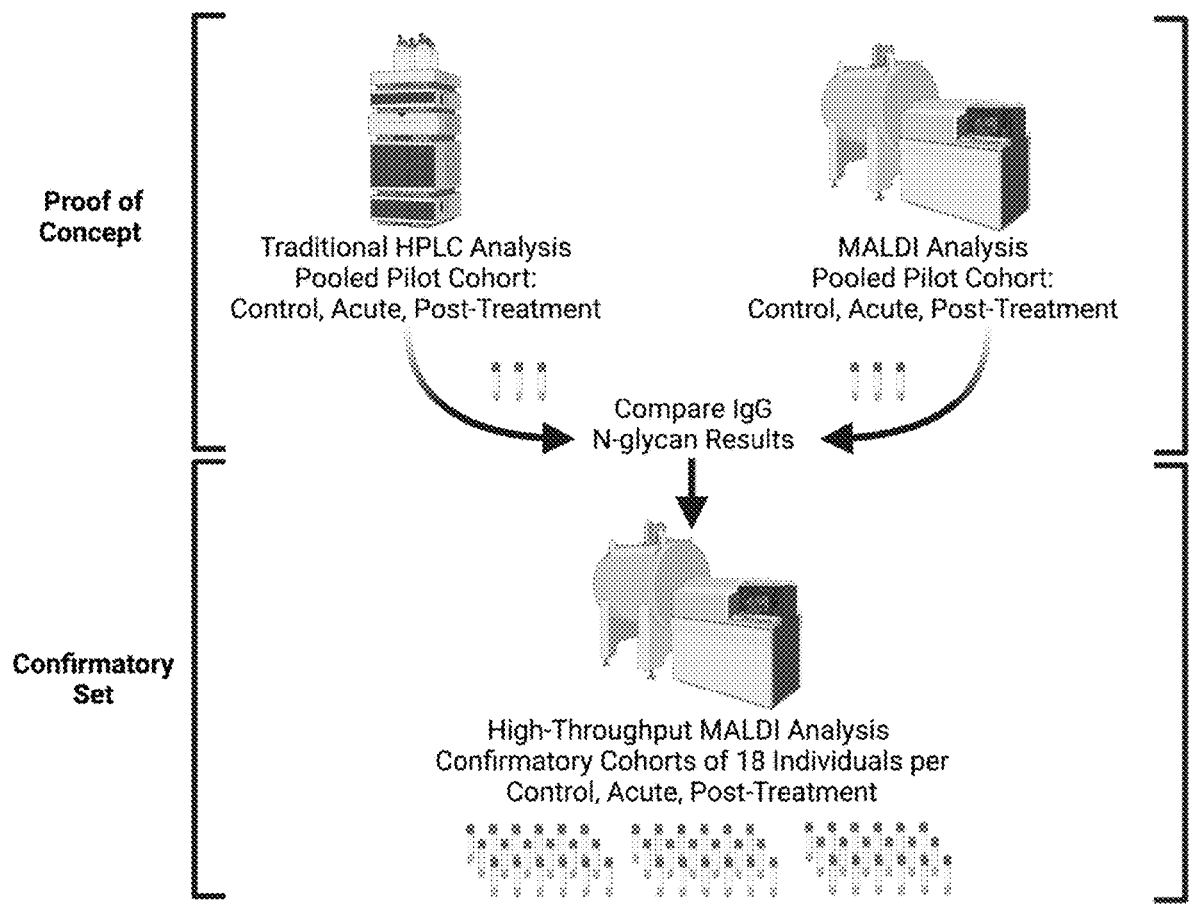

FIG. 12 illustrate some assays described in Example 3.

Figure 13:
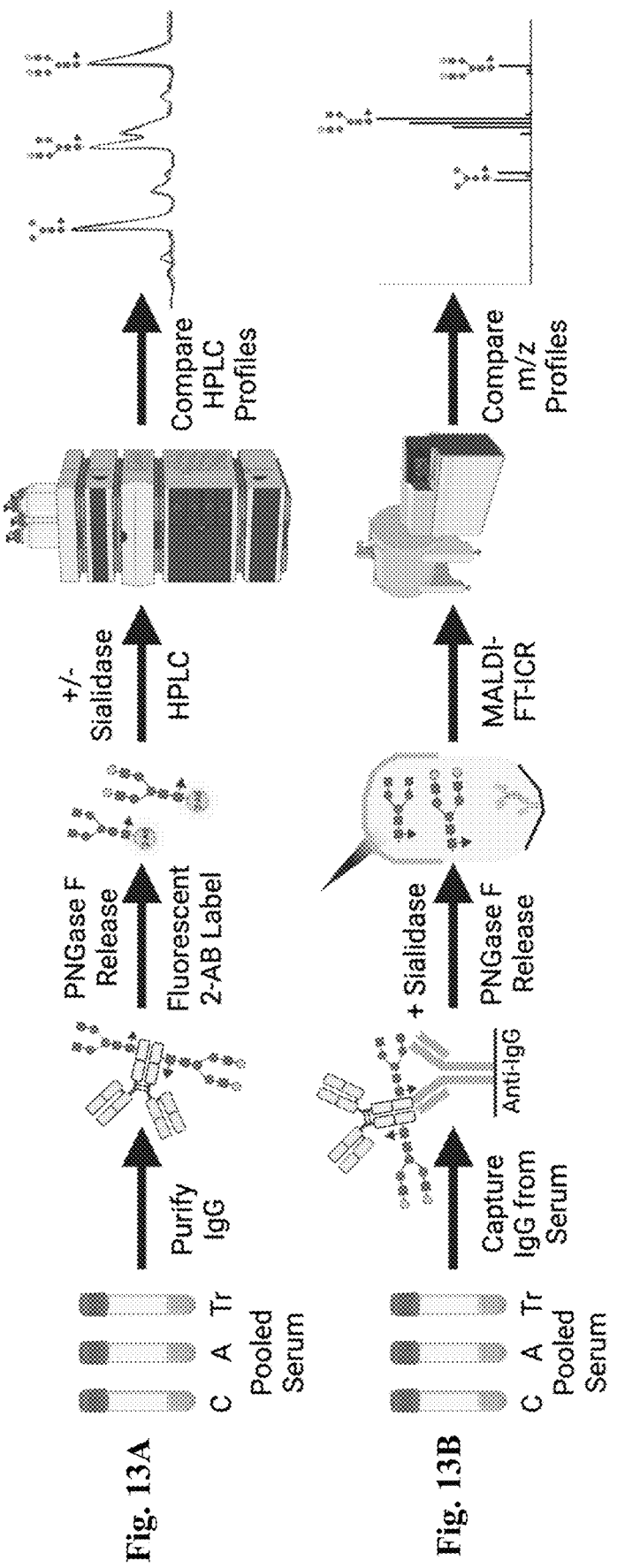

FIGS. 13A-13B: Method comparison between HPLC and MALDI, in accordance with some embodiments. FIG. 13A: HPLC methodology to identify and quantitate Protein A/G purified IgG N-glycan released from patient cohort pooled serum. FIG. 13B: MALDI MS method to identify and quantitate Ab-captured IgG N-glycans released from patient cohort pooled serum. C=control serum, A=Acute serum, and Tr=Treated serum respective to each cohort analyzed.

Figure 14:
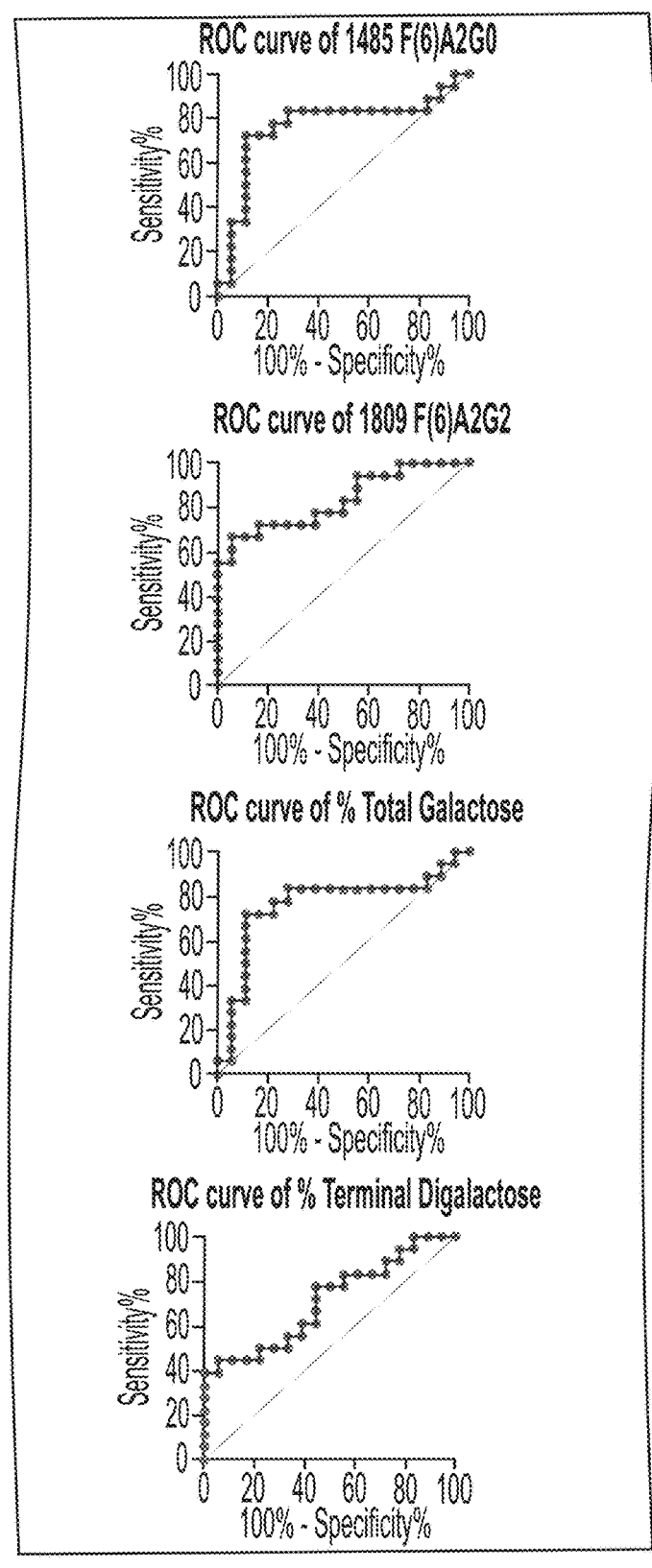

FIG. 14: Acute versus Control Selected N-glycan class discriminators, in accordance with some embodiments. Four N-glycan classes: F(6)A2G0, F(6)A2G2, % Total Galactose, and % Terminal Digalactose were used in combination to discriminate between the healthy age- and sex-matched healthy controls compared to the Acute LD patients. A confusion matrix was tabulated from the performance of the 3 out of 4 positive (value highlighted in the left panel) criteria.

Figure 15:
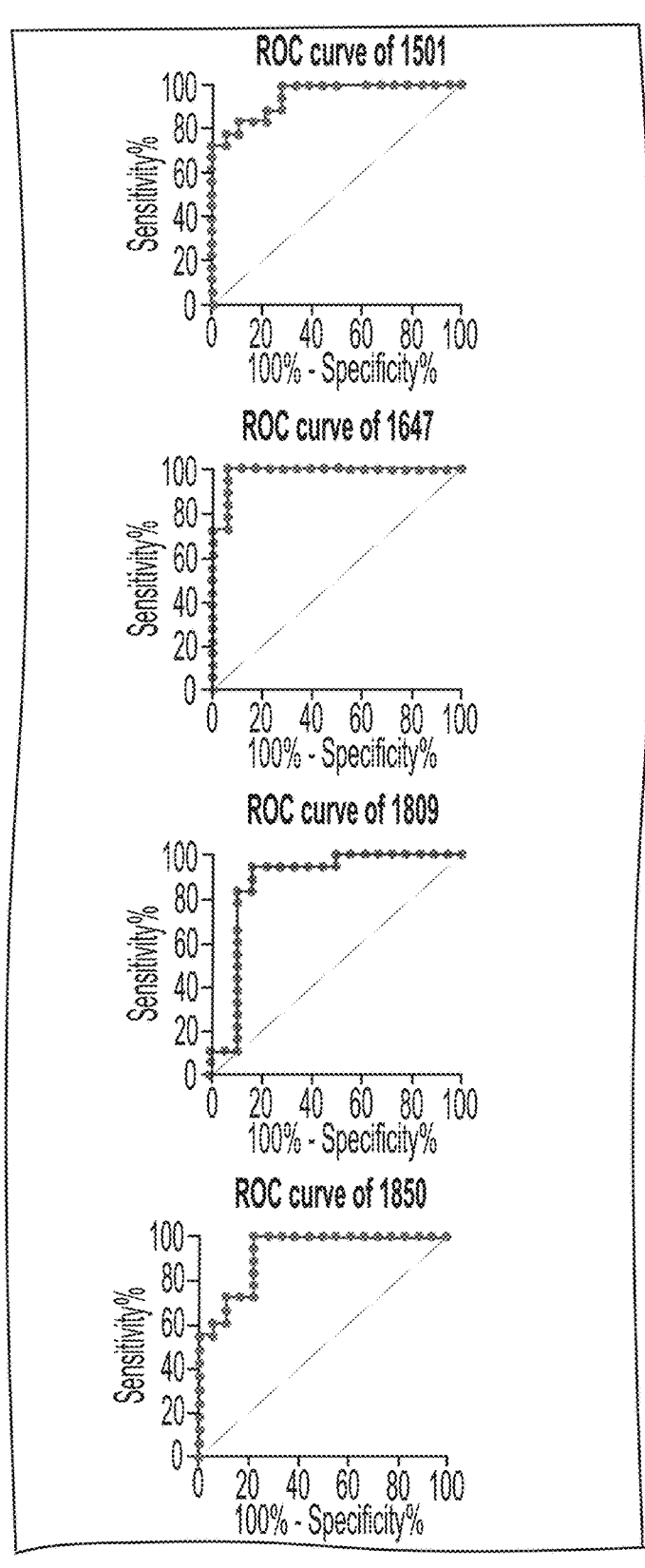
Figure 15:
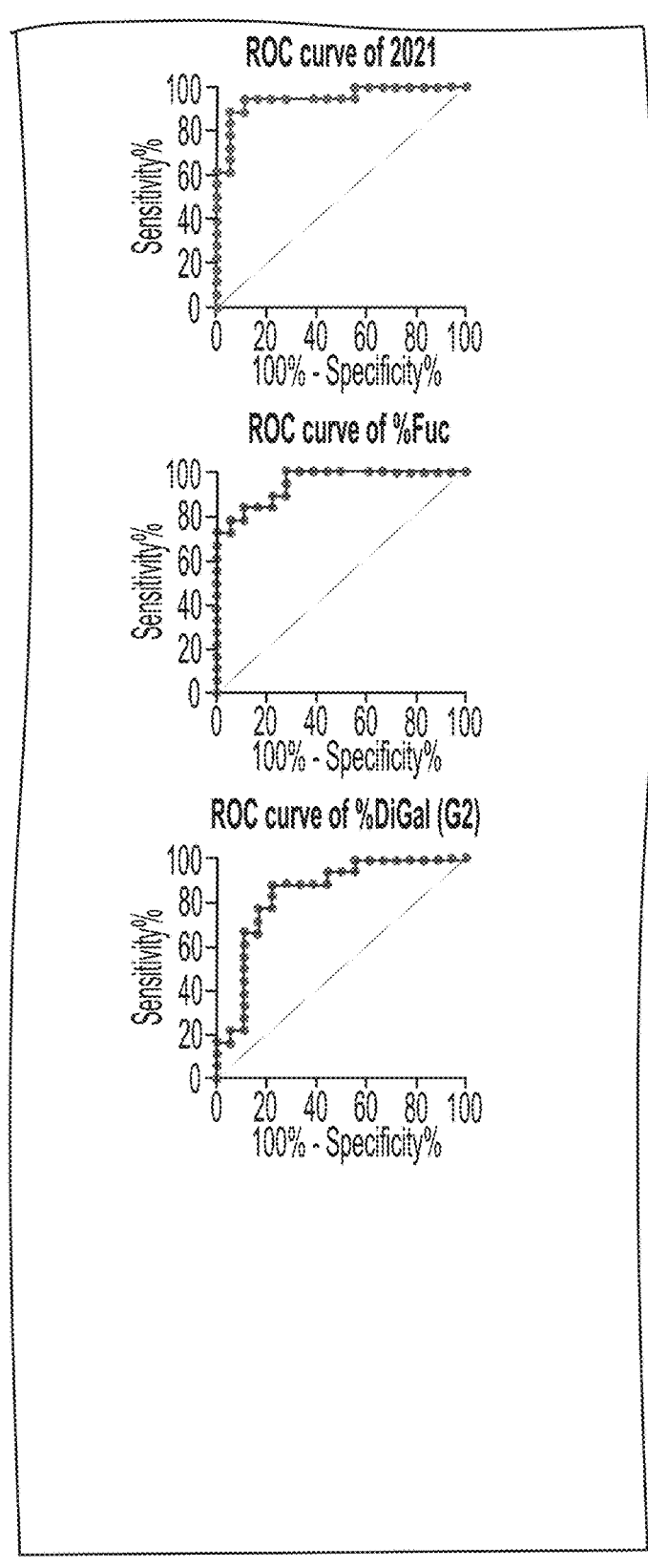

FIG. 15: Acute versus Treated Selected N-glycan class discriminators, in accordance with some embodiments. Seven N-glycan classes were used in combination to discriminate between the Acute LD compared to the Treated LD timepoints. A confusion matrix was tabulated from the performance of the 4 out of 7 positive (value highlighted in the left panel) criteria.

Figure 16:
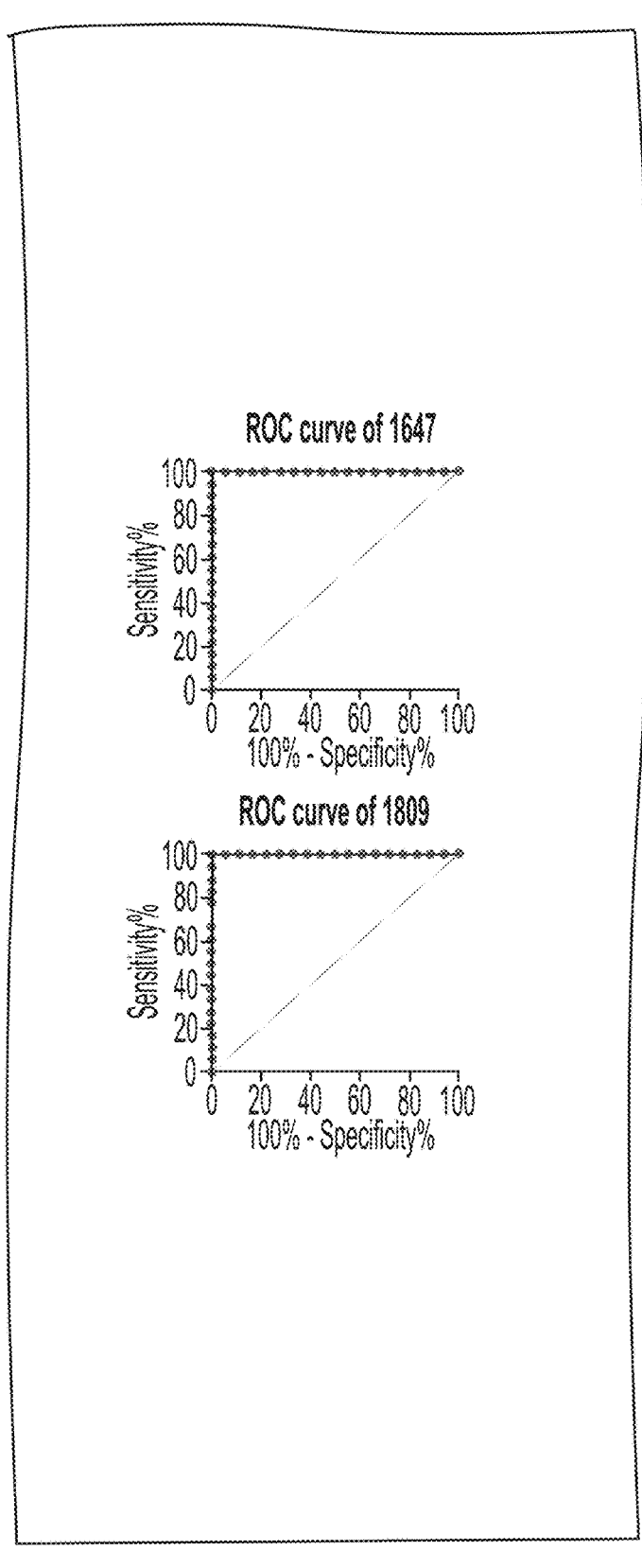

FIG. 16: Treated versus Control Selected N-glycan class discriminators, in accordance with some embodiments. Two N-glycan classes were used in combination to discriminate between the age- and sex-matched healthy controls compared to the Treated LD cohort. A confusion matrix was tabulated from the performance of the 2 out of 2 positive (value highlighted in the left panel) criteria.

FIG. 17: Demographics of Bay Area Lyme Disease Biobank Serum Samples. Sample ID numbers are linked to demographic details including age, sex, ethnicity, antibiotics (Abx) prescribed, and if the patient donated a post-treatment convalescent serum sample. Samples assayed within the pilot study and/or the confirmatory study are noted.

Figures 18A, 18B:
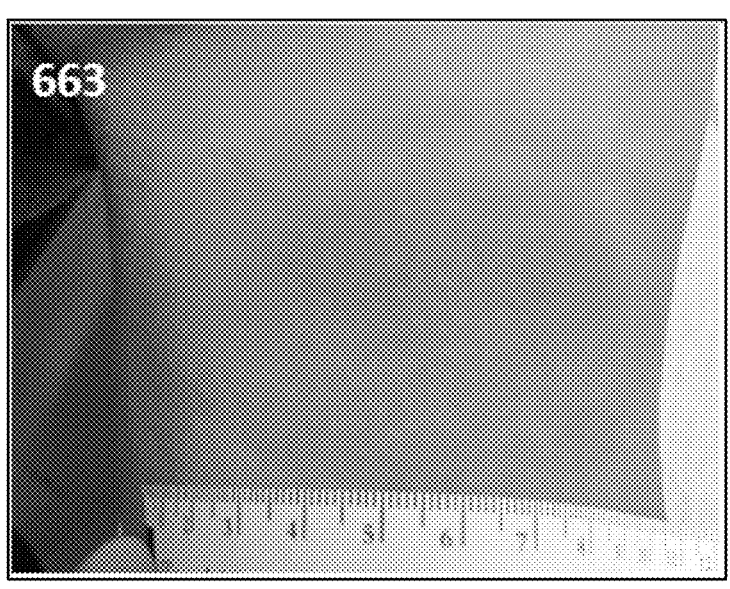
Figure 18C:
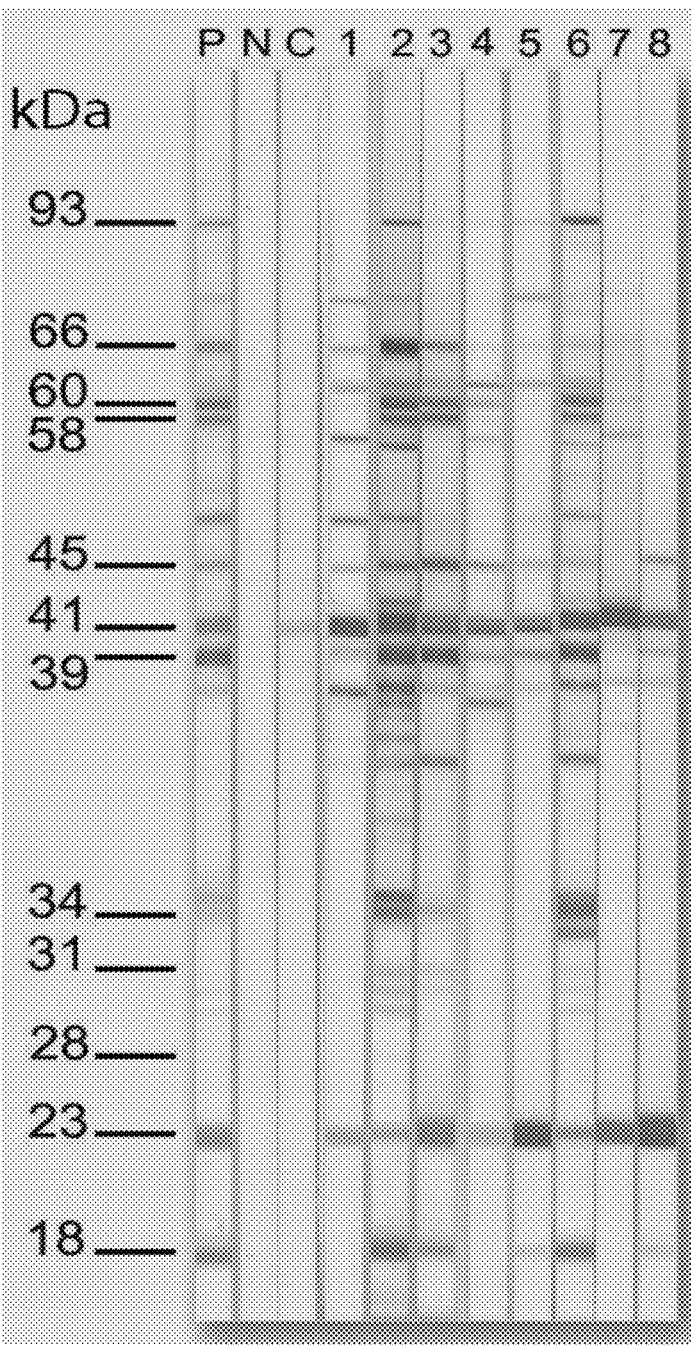

FIG. 18A: Erythema Migrans (EM) indicative of acute LD. FIG. 18B: Control (C), Acute (A), and Treated (Tr) Bb Serology of patient samples pooled for IgG N-glycan analysis. FIG. 18C: Example of CDC IgG serology assay of whole-cell Bb lysate.

Figures 19A, 19B:
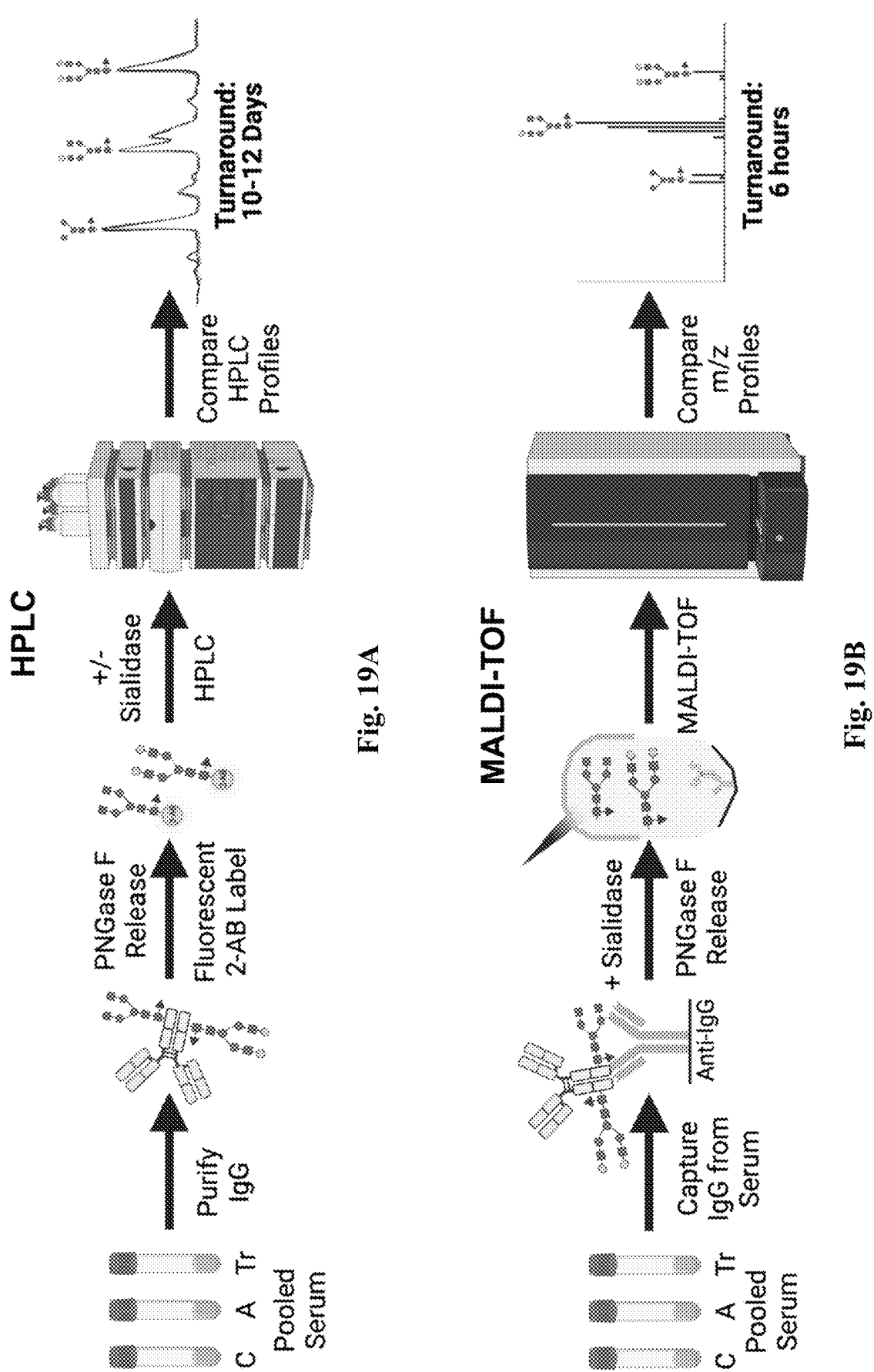

FIGS. 19A-19B: Method comparison, in accordance with some embodiments. FIG. 19A: HPLC methodology to identify and quantitate Protein A/G purified IgG N-glycan released from patient cohort pooled serum. FIG. 19B: MALDI-TOF MS method to identify and quantitate Ab-captured IgG N-glycans released from patient cohort pooled serum.

FIGS. 20A-20C: HPLC analysis of IgG reveals significant changes in N-glycan structure distribution, in accordance with some embodiments. FIG. 20A: HPLC analysis of IgG N-glycans from pooled serum from control (C), acute (A), or treated (Tr) patients reported as the percent area under the curve (AUC) for each peak determined from the average of triplicate samples, +/–S.D. FIG. 20B: IgG N-glycans which decrease in abundance during acute or treated LD, N-glycan structures displayed below. FIG. 20C: IgG N-glycans that increase in abundance during acute or treated LD, N-glycan structures displayed below. Analysis was completed using One-Way ANOVA tests, *p<0.05, p<0.01, *p<0.001. Control represents pooled healthy age-matched serum n=7, Acute represents pooled serum from two-tiered diagnosed Lyme disease patients n=5, Treated represents patients 70-90 days after completion of the reportedly curative round of antibiotic treatment (14-21 d doxycycline) for Lyme disease n=3 (FIGS. 18A-18C).

FIGS. 21A-21C: Desialylated N-glycan HPLC profile confirms the changes observed in FIGS. 20A-20B and allows comparison with sialidase-treated MALDI-TOF analysis, in accordance with some embodiments. FIG. 21C: Sialidase-treated N-glycans were detected by HPLC analysis as discussed in FIGS. 20A-20C. FIG. 21B: Sialidase-treated IgG N-glycans that decrease in abundance during acute or treated LD, N-glycan structures displayed below. FIG. 21C: Sialidase-treated IgG N-glycans that increase in abundance during acute or treated LD, N-glycan structures displayed below. Analysis was completed using One-Way ANOVA tests, *p<0.05, p<0.01, *p<0.001. See descriptions of FIGS. 20A-20C for sample description.

FIGS. 22A-22C: MALDI-TOF analysis of Ab-captured desialylated IgG N-glycans confirms the changes observed in HPLC, in accordance with some embodiments. FIG. 22A: N-glycans were detected by MALDI-TOF analysis of Ab-captured IgG from pooled serum as described in FIGS. 20A-20C. Results are the average of two replicates+/–S.D. and reported as the percent of the total identified N-glycan m/z peak intensity. FIG. 22B: IgG N-glycans that decrease in abundance during acute or treated LD, N-glycan structures displayed below. FIG. 22C: IgG N-glycans that increase in abundance during acute or treated LD, N-glycan structures displayed below. Analysis was completed using One-Way ANOVA tests, *p<0.05, p<0.01, *p<0.001. See description of FIGS. 20A-20C for sample description.

Figure 23:
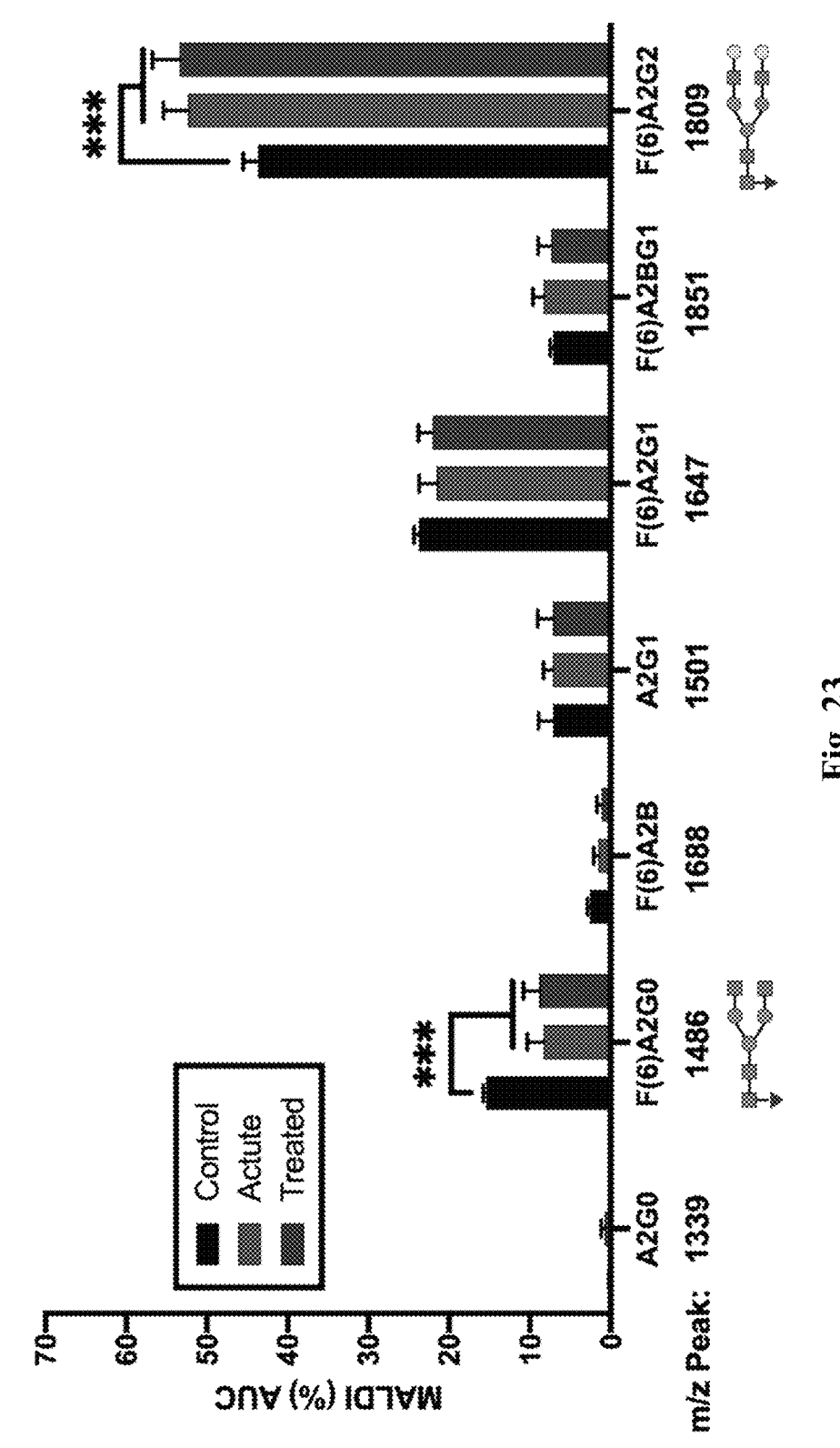

FIG. 23: MALDI-TOF analysis of individual patient desialylated IgG N-glycans confirms the changes observed from pooled samples, in accordance with some embodiments. MALDI-TOF analysis of Ab-captured IgG N-glycans from patient-matched acute (A) and treated (Tr) singlet samples run (sample ID: 640, 663, 673) in duplicate compared to pooled control serum+/–S.D. Results reported as the percent of the total identified N-glycan m/z peak intensity. Analysis completed using One-Way ANOVA tests, *p<0.05, p<0.01, *p<0.001. See FIG. 3 legend for sample description.

Figure 24:
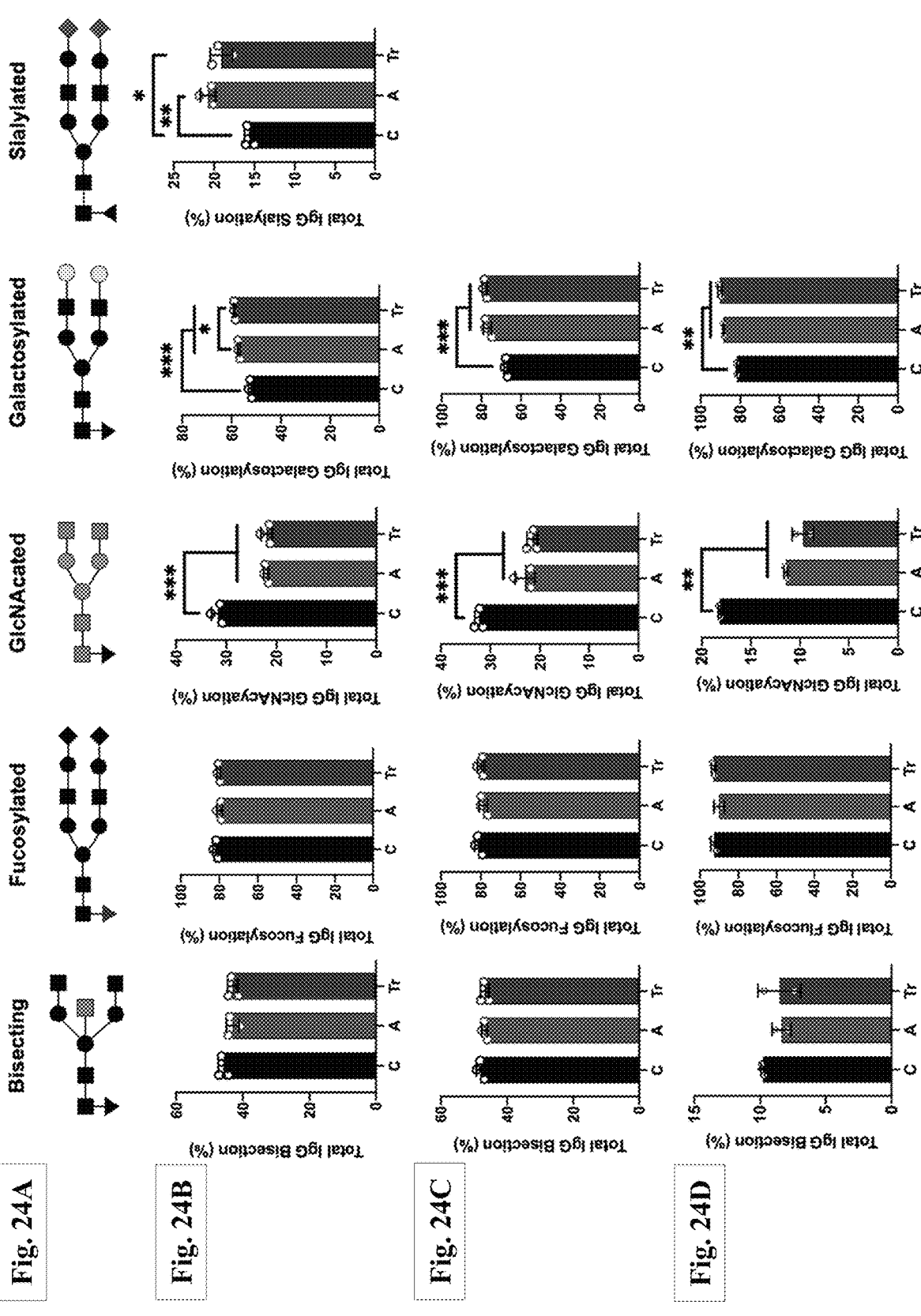

FIGS. 24A-24D: Grouping N-glycans by class reveals significant changes detected by MALDI-TOF and HPLC in pooled serum cohorts, in accordance with some embodiments. FIG. 24A: Labeled N-glycan classes: Bisecting, Fucosylated, GlcNAcated, Galactosylated, Sialylated.

FIG. 24B: HPLC analysis of IgG N-glycans grouped by class from 3 replicates+/–S.D. FIG. 24C: HPLC analysis of desialylated IgG N-glycans grouped by class from 3 replicates+/–S.D. FIG. 24D: MALDI-TOF analysis of desialylated IgG N-glycan classes from 2 replicates+/–S.D. Analysis completed using One-Way ANOVA tests, *p<0.05, p<0.01, *p<0.001. See the descriptions of FIGS. 20A-20C for sample description.

Figure 25:
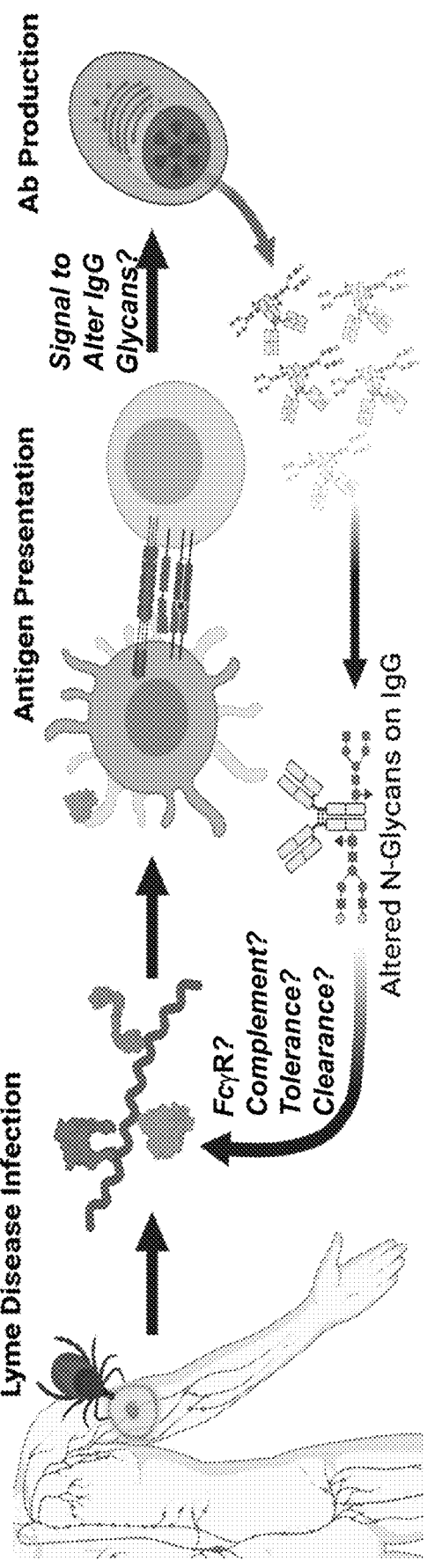

FIG. 25 is a diagram showing a hypothesis of the interplay between antigen presenting cells, T-cells, B-cells, other lymphocytes, and glycosyltransferases during the early immune response to the Bb spirochete leading to altered N-glycans on IgG.

Figures 26A, 26B:
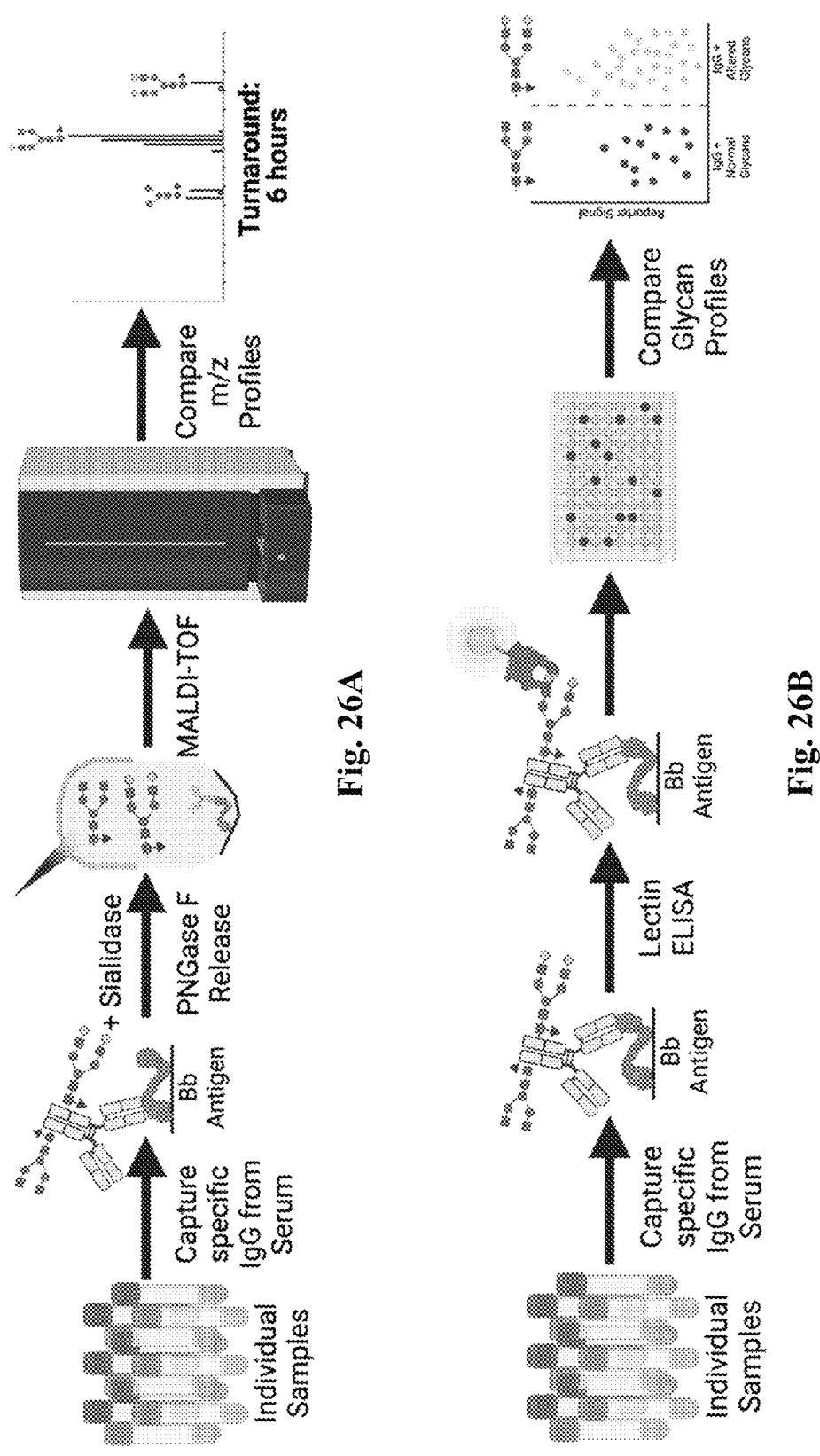

FIGS. 26A-26B are alternative methods to evaluate aberrant N-glycosylation, in accordance with some embodiments. FIG. 26A: MALDI-TOF analysis of Bb antigen-reactive IgG. FIG. 26B: Bb antigen Lectin ELISA.

Figure 27:
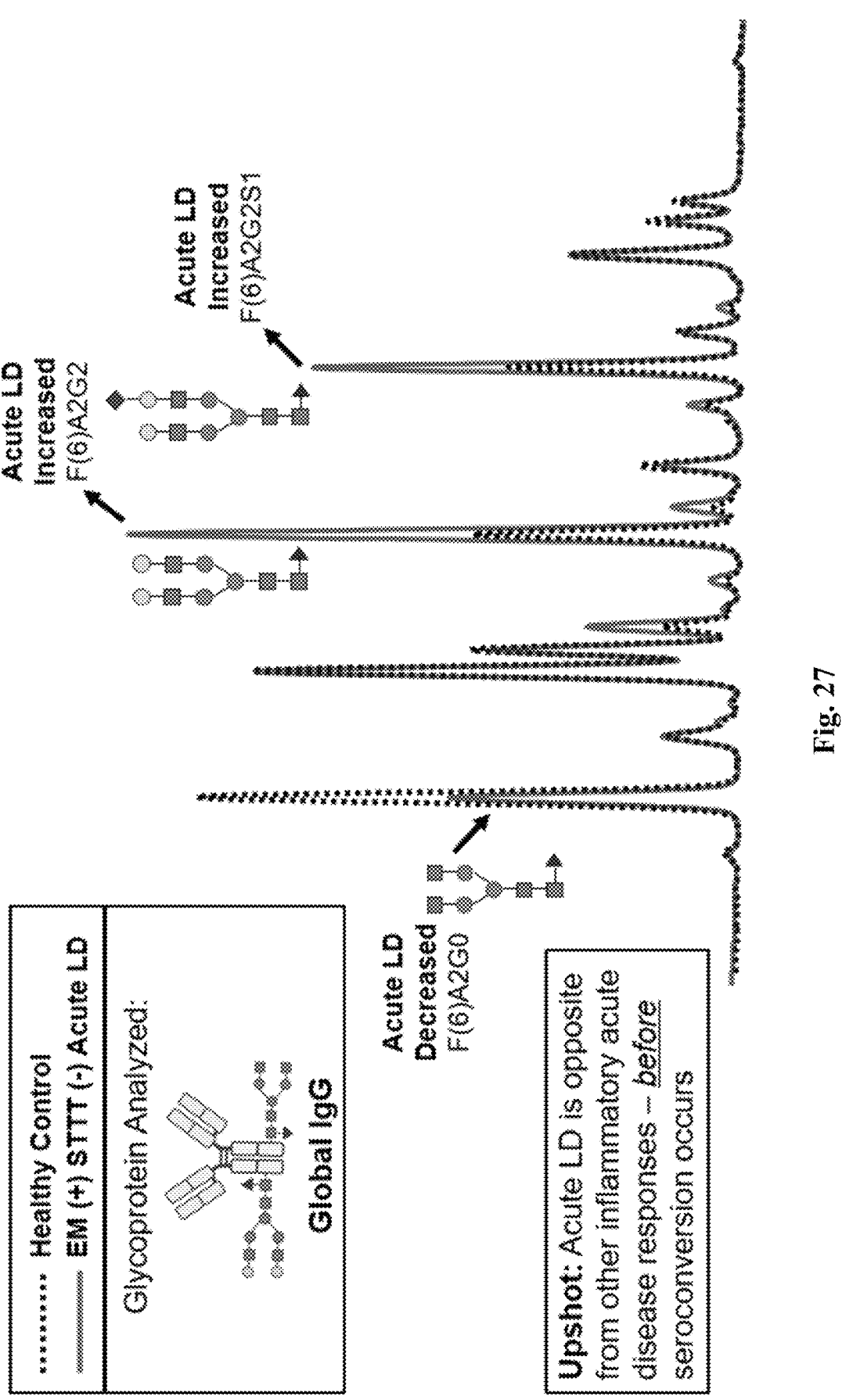

FIG. 27 demonstrates that glycoproteins, such as global IgG, have high gal and sialic acid content in acute Lyme disease, in accordance with some embodiments.

Figure 28:
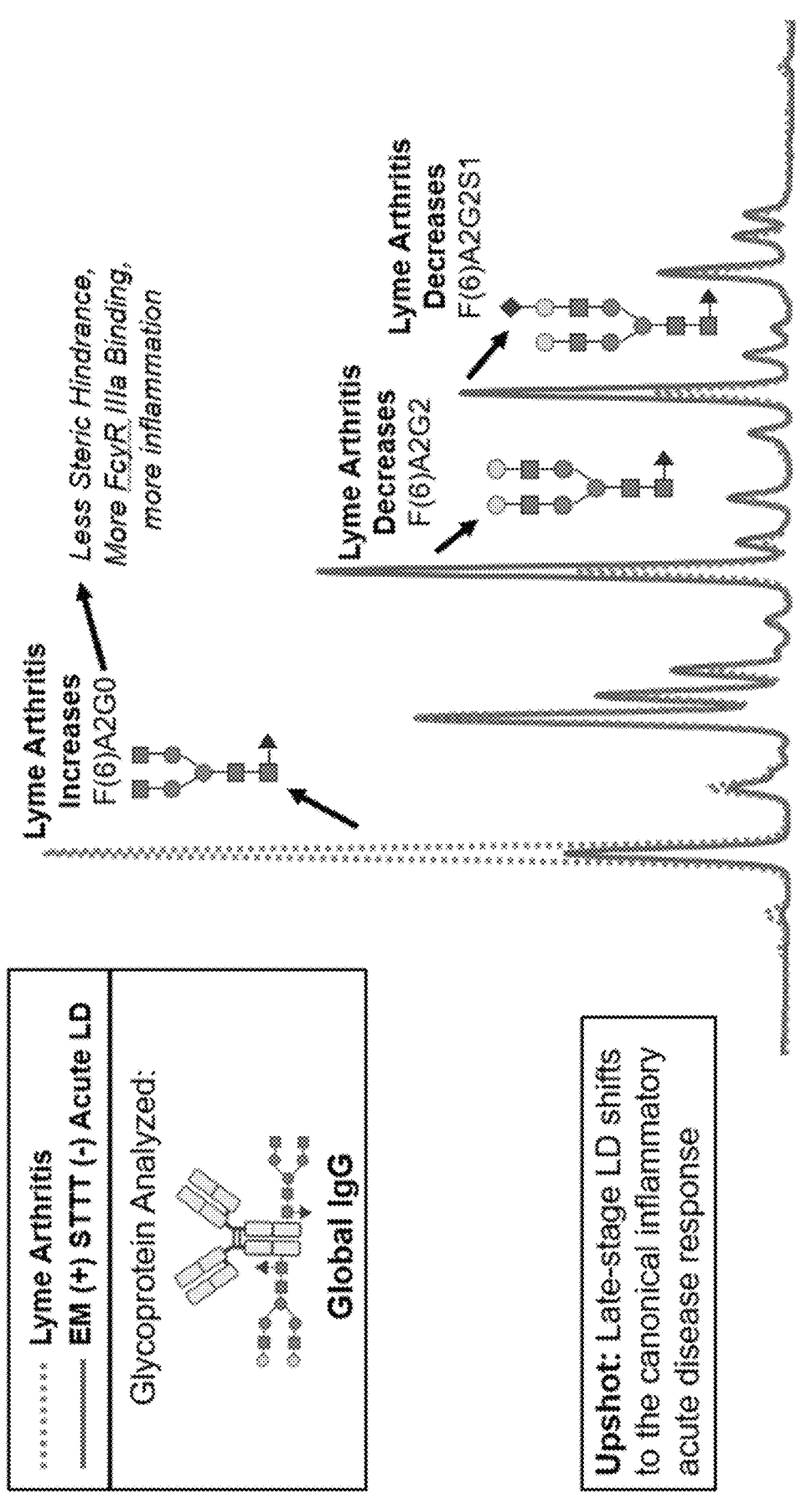

FIG. 28 demonstrates that glycoproteins, such as global IgG, have lower gal & sialic acid content in Lyme arthritis when compared to acute Lyme disease, in accordance with some embodiments.

FIG. 29 demonstrates that the tests herein are able to distinguish treated Lyme disease patients from both subjects without Lyme disease and patients with acute Lyme disease, in accordance with some embodiments.

Figure 31:
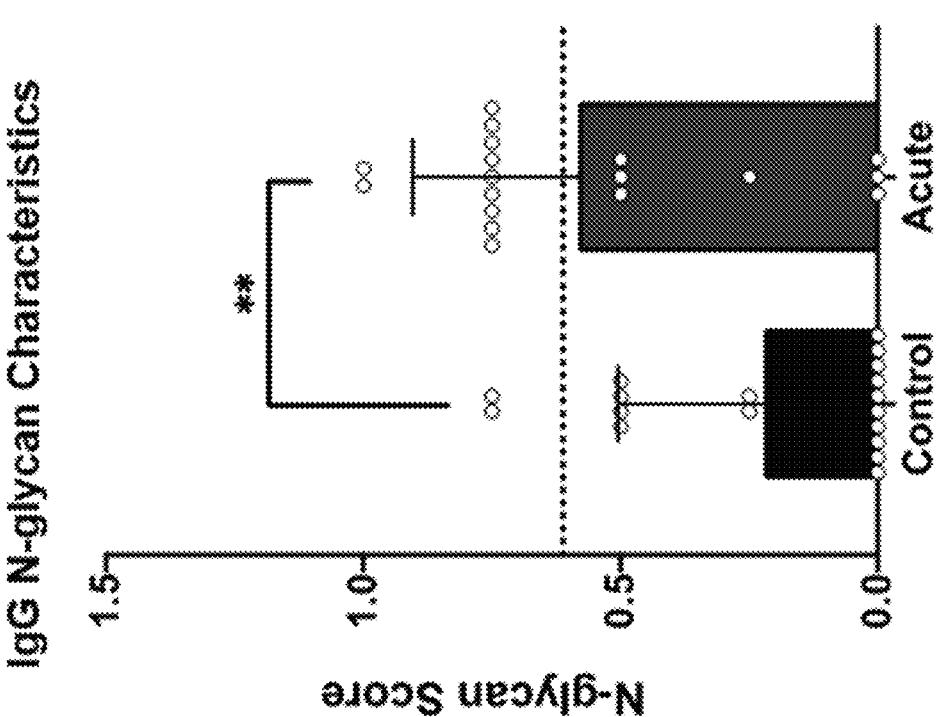

FIG. 30 demonstrates that global IgG N-glycans discriminate acute LD patients, in accordance with some embodiments, FIG. 31 demonstrates that IgG N-glycans discriminate acute LD patients, in accordance with some embodiments.

FIG. 32 demonstrates that the tests herein is able to distinguish previous infection from acute LD patients, in accordance with some embodiments. IgG N-glycan profiles identify primary acute LD and acute LD in patients with a previous history of LD. Fucosylated, digalactose (G2) content from IgG was summed from the UPLC-ESI-MS data and compared between healthy endemic controls, EM (+) STTT (+) Acute LD patients without a history of Lyme disease, and EM (+) STTT (+) patients with a history of previous Lyme disease infection. Control n=18, Acute 1$^{st}$ Infection n=9, acute with previous infection n=9, standard deviation presented.

Figure 33:
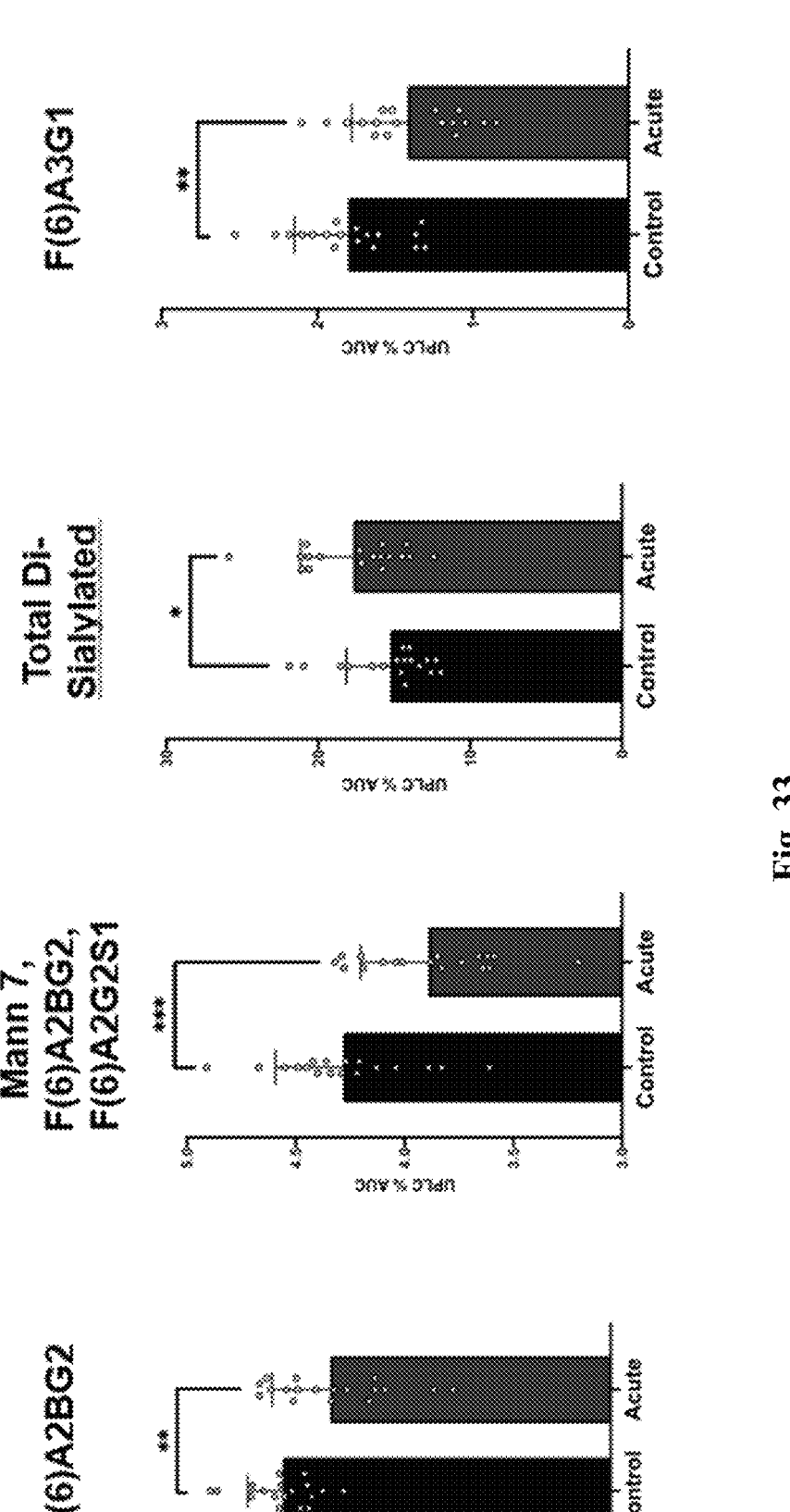

FIG. 33 demonstrates that global IgM N-glycans discriminate acute LD patients, in accordance with some embodiments.

Figure 34:
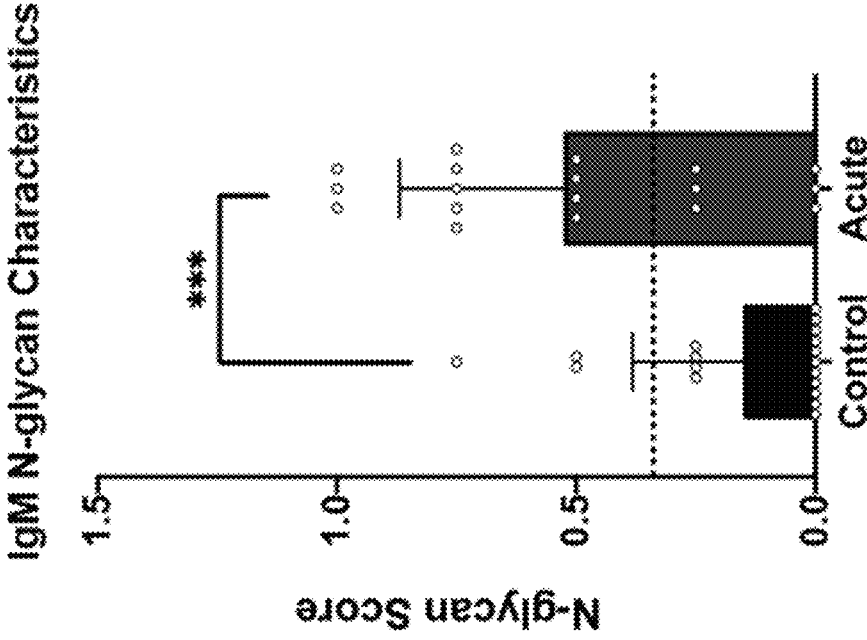

FIG. 34 demonstrates that IgM N-glycans discriminate acute LD patients, in accordance with some embodiments.

Figure 35:
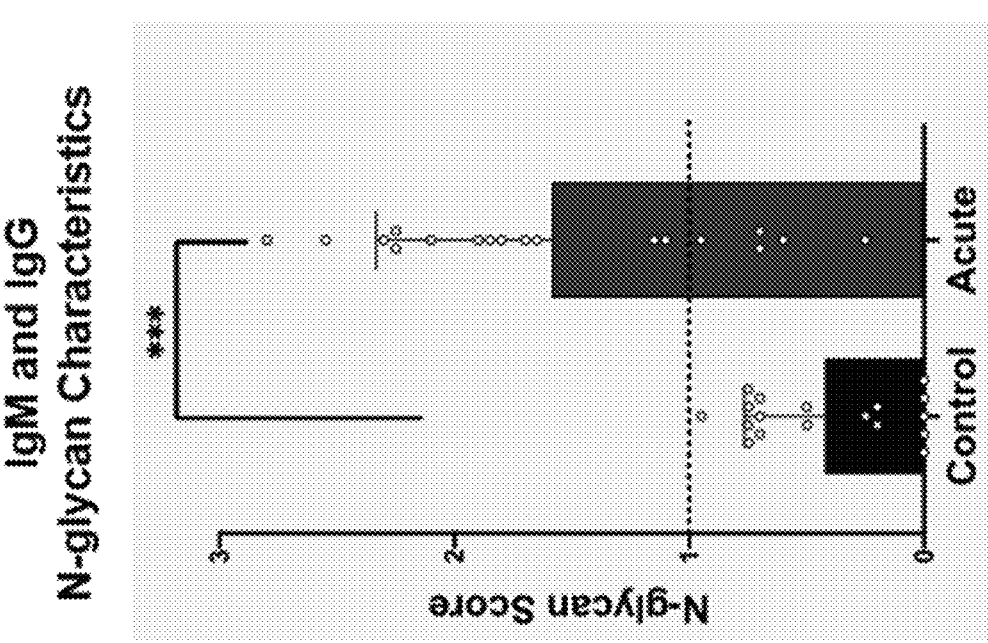

FIG. 35 demonstrates that IgM and IgG N-glycans discriminate acute LD patients better when combined.

Figure 36:
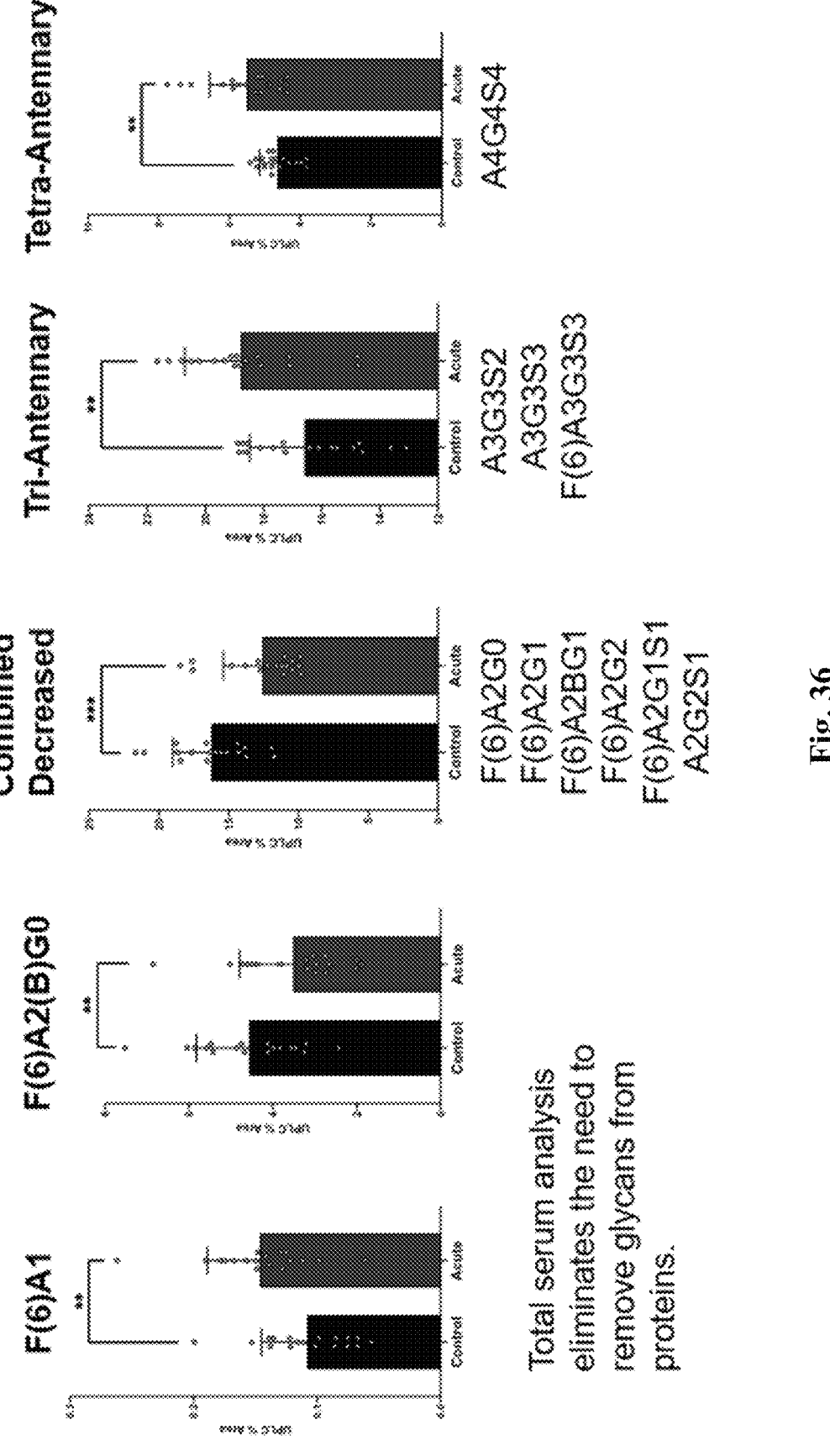

FIGS. 36-37 demonstrate that total serum glycome N-glycans discriminate acute LD patients, in accordance with some embodiments. Total serum analysis eliminates the need to remove glycans from proteins.

DETAILED DESCRIPTION

The following disclosure provides many different embodiments, or examples, for implementing different features of the provided subject matter. Specific examples of components and arrangements are described below to simplify the present disclosure. These are, of course, /merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Currently, acute Lyme disease patients are often diagnosed on clinical grounds, such as for example based on the presence of an erythema migrans (EM) rash. Oftentimes, however; EMs are atypical, unnoticed, or completely absent in the patient. Thus, diagnosis of early Lyme disease is difficult for physicians and is frustrating for patients, particularly in the early stage of the disease such as the first month. When acute Lyme disease is not treated in the early stage, the spirochete disseminates to the joints, brain, and heart, resulting in chronic disability and/or potential loss of life.

Early diagnosis and treatment can effectively avoid the long-term disabilities that are commonly observed with Lyme infections. Early diagnosis of the disease, however, is not currently viable. In responding to the need in the art, the study described herein ("the present study") developed a diagnostic test to detect active Lyme disease infection and/or distinguish it from certain common infections or inflammatory diseases with similar symptoms. In certain embodiments, the diagnostic test employs high sensitivity biomarkers. In certain embodiments, the diagnostic test enables early Lyme disease diagnosis, allows for early treatment of Lyme disease, and is useful in tracking the effectiveness of treatments.

A non-limiting version of the glycoproteomic based test according to the present disclosure, referred to herein as "GlycoLyme," works by identifying unique changes to the sugars attached to proteins in patients, such as but not limited to immunoglobulins. These covalently N-linked glycans participate in modulating immune response. The present study discovered that patients with acute Lyme disease contain significantly increased mannose, galactose, and sialic acid content in the proteins, resulting in larger, more negatively charged glycans compared to healthy controls. In certain embodiments, the GlycoLyme test quantitates and identifies glycans from total serum Immunoglobulin G and M using fluorescent chromatography and mass spectrometry respectively. If patients' glycan profiles meet GlycoLyme's algorithmic threshold, the patient is deemed positive for acute Lyme disease.

The present study confirmed that the GlycoLyme test is highly accurate and can distinguish acute Lyme disease from related diseases or diseases with similar symptoms. As tested in the present study, GlycoLyme has a sensitivity of 72% in EM positive, STTT (+) patients provided by the Bay Area Lyme disease Foundation biobank. This increased sensitivity allows for better detection of acute cases, allowing for patients to start treatments in a more timely fashion. Importantly, the assay can also identify patients who have the EM rash but are not yet seropositive according to EIA or STTT tests. GlycoLyme retains 100% specificity when tested using endemic and non-endemic healthy controls. Importantly, GlycoLyme can discriminate rheumatoid arthritis, syphilis, mononucleosis, and multiple sclerosis from acute Lyme disease. Furthermore, GlycoLyme can distinguish Lyme neuroborreliosis and Lyme arthritis from acute Lyme disease, at least because protein samples of patients suffering from this disease contain a different glycan profile compared to acute Lyme disease. As such, the GlycoLyme approach significantly improves testing accuracy, avoids false positives from mimic diseases, and offers a method to measure treatment efficacy.

The present study further confirmed that GlycoLyme test can be used to determine effectiveness of treatment for Lyme disease. Immunoglobulin glycans are dynamic and reflect the immune state. The GlycoLyme test identifies bisecting glycan structures significantly elevated in treatment-responsive patients who returned to donate blood after remaining symptom-free during convalescence. Thus, patients and clinicians can confirm that the treatment for acute Lyme disease worked, by re-testing their blood using the GlycoLyme test to track their immune response over time.

Accordingly, in some embodiments, the present disclosure is directed to a method of diagnosing Lyme disease.

In some embodiments, the present disclosure is directed to a method of treating, ameliorating, and/or preventing Lyme disease.

In some embodiments, the present disclosure is directed to a method of determining an effectiveness of a treatment for Lyme disease.

Definitions

As used herein, each of the following terms has the meaning associated with it in this section. Unless defined otherwise, all technical and scientific terms used herein generally have the same meaning as commonly understood by one of ordinary skill in the art to which this disclosure belongs. Generally, the nomenclature used herein and the laboratory procedures in animal pharmacology, pharmaceutical science, peptide chemistry, and organic chemistry are those well-known and commonly employed in the art. It should be understood that the order of steps or order for performing certain actions is immaterial, so long as the present teachings remain operable. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference.

Unless defined otherwise, all technical and scientific terms used herein have the same meaning as commonly understood by one of ordinary skill in the art to which the instant specification pertains. Although any methods and materials similar or equivalent to those described herein can be used in the practice for testing of the instant specification, selected materials and methods are described herein. In describing and claiming the instant specification, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

A disease or disorder is "alleviated" if the severity of a symptom of the disease or disorder, the frequency with which such a symptom is experienced by a patient, or both, is reduced.

As used herein, the term "composition" or "pharmaceutical composition" refers to a mixture of at least one compound useful within the specification with a pharmaceutically acceptable carrier. The pharmaceutical composition facilitates administration of the compound to a patient or subject. Multiple techniques of administering a compound exist in the art including, but not limited to, intravenous, subcutaneous, oral, aerosol, parenteral, ophthalmic, pulmonary and topical administration.

An "effective amount" or "therapeutically effective amount" of a compound is that amount of compound that is sufficient to provide a beneficial effect to the subject to which the compound is administered. An "effective amount" of a delivery vehicle is that amount sufficient to effectively bind or deliver a compound.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the specification within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the specification, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other nontoxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the specification, and are physiologically acceptable to the patient. Supplementary active compounds may also be incorporated into the compositions. The "pharmaceutically acceptable carrier" may further include a pharmaceutically acceptable salt of the compound useful within the instant specification. Other additional ingredients that may be included in the pharmaceutical compositions used in the practice of the instant specification are known in the art and described, for example in Remington's Pharmaceutical Sciences (Genaro, Ed., Mack Publishing Co., 1985, Easton, PA), which is incorporated herein by reference.

As used herein, "treating a disease or disorder" means reducing the frequency with which a symptom of the disease or disorder is experienced by a patient. Disease and disorder are used interchangeably herein.

As used herein, the term "treatment" or "treating" encompasses therapy. Accordingly, the compositions and methods of the instant specification include therapeutic applications. Therefore "treating" or "treatment" of a state, disorder or condition includes: (i) inhibiting the state, disorder or condition, i.e., arresting or reducing the development of the disease or at least one clinical or subclinical symptom thereof, and/or (iii) relieving the disease, i.e. causing regression of the state, disorder or condition or at least one of its clinical or subclinical symptoms.

As used herein, the term "prevention" or "preventing" encompasses prophylaxis y. Accordingly, the compositions and methods of the instant specification include prophylactic applications. Therefore prevention" of or "preventing" a state, disorder or condition includes preventing or delaying the appearance of clinical symptoms of the state, disorder or condition developing in a subject that may be afflicted with or predisposed to the state, disorder or condition but does not yet experience or display clinical or subclinical symptoms of the state, disorder or condition.

Ranges: throughout this disclosure, various aspects can be presented in a range format. It should be understood that the description in range format is merely for convenience and brevity and should not be construed as an inflexible limitation on the scope of the instant specification. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Abbreviations: Bb: *Borrelia burgdorferi* or *Borrelia burgdorferi* sensu lato. EM: erythema migrans. EIA: enzyme immunoassay. ESI: electrospray ionization. HPLC: high-performance liquid chromatography. LC: liquid chromatography. LM: Lyme disease. MALDI: matrix-assisted laser desorption/ionization. MALDI FT-ICR: matrix-assisted laser desorption/ionization Fourier transform ion cyclotron resonance. MS: mass spectrometry. MALDI-TOF: matrix-assisted laser desorption/ionization time of flight. PTLDS: post-treatment Lyme disease syndrome. STTT: standard two-tier testing. UPLC: ultra-performance liquid chromatography.

Method of Diagnosing Lyme Disease

In some aspects, the present disclosure is directed to methods of diagnosing pathologies of *Borrelia* infection (such as but not limited to a *Borrelia burgdorferi* infection, such as but not limited to a *Borrelia burgdorferi* sensu stricto infection) and assessing treatment success.

In some embodiments, the pathologies of *Borrelia* infection includes Lyme disease. In some embodiments, the pathologies of *Borrelia* infection includes acute Lyme disease.

As used herein, the term "acute Lyme disease" refers to the early stage of localized disease caused by a *Borrelia* infection. Symptoms with early localized (or "acute") Lyme disease may begin hours, a few days, or even weeks after a tick bite. At this stage, the infection has not yet spread throughout the body, and treatments of Lyme disease with antibiotics has significantly higher chance of curing the disease compared to when the bacteria are beginning to spread throughout the body ("early disseminated Lyme disease") or when the bacteria have spread throughout the body ("late disseminated Lyme disease").

In some embodiments, the method includes obtaining a test sample such as but not limited to a biological fluid from a subject suspected of having been infected with *Borrelia* spirochete and comparing the detected protein glycosylation levels/patterns with reference values for glycosylation of proteins. Reference values are established from subjects with no known *Borrelia* infection, or established from subjects with known *Borrelia* infection. Either or both reference values can be compared with the detected glycosylation levels/patterns, and the comparison reveals presence or absence of pathology such as Lyme Disease. Protein glycosylation can be measured from any host serum glycoprotein such as Immunoglobulins, acute phase proteins, and patient serum proteins.

In some embodiments, the measure of protein glycosylation levels/patterns shows an increased complexity of sugar structure with decreased terminal galactose structures and an increase in fucosylation, antennary, or sialic acid structures.

In some embodiments, the detection can be through any suitable method including plate-based assays, chromatography or mass spectrometry. Detection may be through a labeled or unlabeled glycosyl moiety. The detection regent can directly label the glycosyl moieties, for example, via carbohydrate specific chemicals, labels, dyes, or using a labeled carbohydrate binding protein such as a lectin, immunoglobulin or other suitable binding agent. Detection can be through a secondary reagent, for example by first capturing the target analyte and then contacting the capture reagent-target complex with a labeled secondary reagent. Detection can proceed by separating glycosyl moieties from the proteins prior to the quantifiable detection of glycosylation.

Detection can proceed by separating glycoproteins from the test sample prior to the quantifiable detection of glycosylation.

In some embodiments, the method of diagnosing Lyme disease in a subject includes: determining a glycosylation profile of a protein in the subject, wherein a change of the glycosylation levels/patterns of the protein in relative to a normal glycosylation profile is associated with Lyme disease; and comparing the glycosylation profile of the protein in the subject with a predetermined first glycosylation profile indicating free of Lyme disease or a predetermined second glycosylation profile indicating Lyme disease.

In some embodiments, the change of the protein glycosylation profile includes an increased level of glycosylation, or a decreased level of glycosylation.

In some embodiments, the change of the glycosylation profile includes an increased complexity of sugar structure. In some embodiments, the increased complexity of sugar structure includes decreased level of terminal galactose structures and an increased level of fucosylation, antennary, or sialic acid structures.

In some embodiments the protein comprises at least one selected from the group consisting of Immunoglobulin G (IgG), Immunoglobulin M (IgM), Complement component 9, pentraxin-related C-reactive protein, Cystatin E/M, Peptidoglycan recognition protein 2, Afamin, fructose-bisphosphate Aldolase B, Apolipoprotein A-IV, Apolipoprotein B, Complement factor H related 1, Coagulation factor IX, Fructose-1,6-bisphosphatase 1, Vitamin D-binding protein-macrophage activating factor, Interalpha (globulin) inhibitor H2, Inter-alpha-trypsin inhibitor 4, Platelet factor 4 (CXCL7), S100 calcium binding protein A9, pentraxin-related C-reactive protein, Serum amyloid A-1 protein, C-X-C motif chemokine 9, C-X-C motif chemokine 10, C-C motif chemokine 19, pentraxin-related C-reactive protein, Complement component 9, Interalpha (globulin) inhibitor H2, Kininogen-1, Gelsolin, Interleukin-1 receptor accessory protein, Serum amyloid A-1 protein, Serum amyloid A-2 protein.

In present study, glycosylation profiles of IgG, IgM, and total serum proteins (for example, as assayed by total serum glycome N-glycans) were studied in samples from Lyme disease patients of different disease stages, as well as samples from patients with non-Lyme disease patients or healthy subjects. Such glycosylation profiles were confirmed to be useful for diagnosing Lyme disease, including establishing the stages of the Lyme disease. Accordingly, in some embodiments, the protein includes at least one selected from the group consisting of IgG, IgM, and total serum proteins.

The present study confirmed that the glycosylation profiles of samples of acute Lyme disease, disseminated Lyme disease (such as Lyme neuroborreliosis or Lyme arthritis), recovering patients, recovered patients, or non-Lyme infection or inflammatory disease are different from each other. As such, the glycosylation profile of samples from a subject can be compared to the glycosylation profiles above to establish the stages of Lyme disease in the subject in addition to absence or presence of Lyme disease.

Accordingly, in some embodiments, the glycosylation profile of the protein in the subject is compared with at least one of a glycosylation profile indicating acute Lyme disease, a glycosylation profile indicating disseminated Lyme disease (such as Lyme neuroborreliosis or Lyme arthritis), a glycosylation profile indicating a state of recovering from Lyme disease, a glycosylation profile indicating a recovered case of Lyme disease, and a glycosylation profile indicating a non-Lyme infection or inflammatory disease. In some embodiments, the method determines the stage of Lyme disease in addition to the absence or presence of Lyme disease. In some embodiments, the stage of Lyme disease includes acute Lyme disease, disseminated Lyme disease (such as but not limited to Lyme neuroborreliosis or Lyme arthritis), state of recovering from Lyme disease, or reinfection with Lyme disease.

The presence of anti-*Borrelia* antibody, such as an anti-*Borrelia burgdorferi* antibody, indicates that the subject is having a non-acute Lyme disease (for example disseminated Lyme disease, or recovering from Lyme disease), is having an acute Lyme disease from the second or subsequent infection, or has recovered from Lyme disease. Further, the absence of the antibody indicates that the subject has never suffered from Lyme disease, or is suffering from the first-time acute Lyme disease. It thus follows that the presence/absence of anti-*Borrelia* antibodies can provide useful information to increase the accuracy of the present glycosylation profile-based method. Accordingly, in some embodiments, the method further comprises detecting an anti-*Borrelia* antibody, such as an anti-*Borrelia burgdorferi* antibody, in the subject.

The method of determining the glycosylation profile of the protein in the subject or constructing glycosylation profiles of Lyme disease (including different stages of Lyme disease), non-Lyme infections or inflammatory diseases, and healthy subjects are not limited.

In some embodiments, the protein of interest is purified from the sample. In some embodiments, all the proteins in the sample are proteins of interest (see e.g., FIGS. 36-37, total serum analysis can eliminate the need to purify proteins and/or removing glycans from proteins). In some embodiments, the glycans are released from the protein before the glycosylation profile is determined. In some embodiments, the glycans are not released from the protein and the profiles are determined with glycans attached to the protein.

The method of determining glycosylation profile of a protein is not limited. In some embodiments, the glycosylation profiles are determined by a matrix-assisted laser desorption/ionization (MALDI) mass spectrometry-based method, a high-performance liquid chromatography (HPLC)-based method, or an enzyme-linked immunosorbent assay (ELISA)-based method.

The present study discovered that the method herein is able to detect acute Lyme disease before anti-*Borrelia* antibodies are found in the serum. Accordingly, in some embodiments, the method diagnoses an acute Lyme disease in the subject before seroconversion.

Method of Treating, Ameliorating, and/or Preventing Lyme Disease

The present study developed a novel approach of diagnosing Lyme disease, which can diagnose Lyme disease at acute stage before seroconversion. Since the treatments for Lyme disease are significantly more effective at acute Lyme disease stage than later stages, in some aspects, the present disclosure is directed to methods of treating, ameliorating, and/or preventing Lyme disease.

In some embodiments, the method of treating, ameliorating, and/or preventing Lyme disease includes: determining a glycosylation profile of a protein in the subject, wherein a change of the glycosylation levels/patterns of the protein in relative to a normal glycosylation profile is associated with Lyme disease; comparing the glycosylation profile of the protein in the subject with a predetermined first glycosylation profile indicating free of Lyme disease or a predetermined second glycosylation profile indicating Lyme disease; and if the glycosylation profile of the protein in the subject does not correspond to the first glycosylation profile or the glycosylation profile of the protein in the subject correspond to the second predetermined level, administering to the subject an effective amount of compound effective for treating, ameliorating, and/or preventing Lyme disease.

In some embodiments, the step of determining a glycosylation profile of a protein in the subject, the step of comparing the glycosylation profile of the protein in the subject with the first/second glycosylation profile, as well as establishing the first/second glycosylation profiles, are the same as or similar to those described elsewhere herein, such as in the "Method of Diagnosing Lyme disease" section.

In some embodiments, the compound includes an antibiotic effective for killing a *Borrelia* bacteria.

In some embodiments, the antibiotic includes at least one selected from the group consisting of doxycycline, amoxicillin, a cephalosporin (such as ceftriaxone, cefotaxime, or cefuroxime axetil) and azithromycin.

Method of Evaluating Treatment of Lyme Disease

The present study discovered that the glycosylation profiles of patients who are recovering or have recovered from Lyme disease are different from the glycosylation profiles of, for example, acute Lyme disease patient. Accordingly, in some aspects, the present disclosure is directed to a method of evaluating a treatment of Lyme disease in a patient.

In some embodiments, the method includes determining a glycosylation profile of a protein in the subject after the subject has been diagnosed with and received treatment for Lyme disease; and comparing the glycosylation profile of the protein in the subject with a predetermined glycosylation profile indicating a state of recovering from Lyme disease, a predetermined glycosylation profile indicating recovered from Lyme disease, and a predetermined glycosylation profile indicating neither recovering nor recovered.

In some embodiments, the step of determining a glycosylation profile of a protein, the step of comparing the glycosylation profile of the protein in the subject with predetermined glycosylation profiles, as well as establishing the predetermined glycosylation profiles are the same as or similar to those described elsewhere here, such as in the "Method of Diagnosing Lyme disease" section.

EXAMPLES

The instant specification further describes in detail by reference to the following experimental examples. These examples are provided for purposes of illustration only, and are not intended to be limiting unless so specified. Thus, the instant specification should in no way be construed as being limited to the following examples, but rather, should be construed to encompass any and all variations which become evident as a result of the teaching provided herein.

Example 1: State of Human Lyme Borreliosis and the Potential Application of Sera Glycome Analysis Cases of Lyme Borreliosis have steadily increased over the last four decades. When the disseminated disease is not diagnosed and treated in a human host, the long-term effects are devastating. Strengths and shortcomings of current Lyme Borreliosis diagnostics are reviewed. The application of glycan analysis is introduced as a novel method to potentially diagnose and characterize Lyme Borreliosis. Glycosylated acute-phase proteins which are altered during early Lyme Borreliosis are examined. Lastly, characterization of the glycosylation pattern of Fc portions of IgM and IgG glycans is discussed as a potential marker of response-to-treatment.

Example 1-1: The Rise of Lyme

In North America, Europe, and Asia, Lyme Borreliosis (LB) is caused by the transmission of *Borrelia burgdorferi* sensu lato species complex via the feeding of *Ixodes* spp. ticks to the human host. The earliest known case of LB was confirmed by genome sequencing in a 5,300-year-old individual in the Italian part of the Otztal Alps. More recently, LB was identified in the US during the late 1970s in association with unexplained cases of childhood arthritis. The causative agent of the arthritis was determined to be *Borrelia burgdorferi* sensu stricto (Bb). The rise in LB has been attributed in part to the reintroduction of forests and deer into the Northeast and Midwest US during the mid-20 century. Case counts continue to rise; with over 20,000 annual reported cases of LB by 2010. A decade later, LB is the most common vector-borne disease in the US and totals an estimated 300,000 cases annually. While a majority of the LB cases are still located within the Northeast and upper-Midwest regions, ecological and environmental changes are promoting a gradual geographic expansion.

Example 1-2: Etiology and Pathology of Lyme Disease

Bb is a highly motile gram negative extracellular pathogen. One third of the Bb genome exists as linear and circular plasmids—making the species contain the most complex genomes among the known bacteria. During the acute phase infection in humans, Bb activates a proinflammatory Th1 response via interferon alpha and Toll-like receptor 2 signaling pathways. Bb encodes proteins that promote avoidance of compliment mediated lysis, antigenic variation of VlsE and outer surface protein C (OpsC), and adhesion to host decorin, glycosaminoglycans, and fibronectin. Bb has a slow growth rate due to its dependence on glycolysis to produce ATP and a requirement to scavenge choline phospholipids from host cell membranes. Human host cell metabolism of arachidonic acids, glycolysis, and glycolipids are altered during LB.

The acute stage of LB occurs within 1-2 weeks post-exposure with an erythema migrans skin rash (EM) identified in roughly half of infected individuals. Moreover, the classic Bull's Eye Rash EM is present in 9% of LB cases, while roughly 50% of LB patients will present with a 'diffusely homogenous red plaque or patch' EM. Independent of EM, patients will be either asymptomatic or present with headache, arthralgias, and fever. Dendritic cells located within the dermis phagocytose and present Bb antigens to T-cells for production of antibodies early during disease progression. Untreated infections will disseminate over the following weeks to months leading to a wide array of symptoms including bilateral Bell's facial nerve palsy, Lyme Carditis, Lyme Arthritis, and Lyme Neuroborreliosis. In addition, pregnant women often lack a clear serodiagnostic profile. Thus, in untreated pregnant women, the Bb spirochete has been documented to cause myriad congenital LB-associated developmental disorders and fetal demise.

Example 1-3: Diagnosis

Prior to laboratory testing for LB, physicians will screen for high pretest probability by collecting a detailed exposure history as well as patient signs and symptoms such as headache or arthralgias. The pre-test screening reduces the rate of false positives during diagnosis. Patients who live in or have traveled to an LB-endemic area presenting with an EM are promptly diagnosed and will begin treatment without laboratory testing.

Most patients with a suspected LB case require a stepwise serological assay to confirm the diagnosis. A positive preliminary enzyme immunoassay of patient serum is followed by a western immunoblot of IgM and IgG targeting Bb whole-cell lysate. Serology based assays have a sensitivity of ~50%. In addition, the nature of serodiagnosis requires the host to mount an immune response over 1-2 weeks. This serological 'Window Period' increases the chance for the Bb infection to disseminate into the host before a clear clinical diagnosis is rendered. Moreover, immunoblots cannot differentiate between antibodies responding to an active infection compared to a previously treated infection. Thus, once seroconversion has occurred, reinfection with LB proves difficult to diagnose with the current testing protocol in the absence of an EM.

*Ixodes* spp. ticks can harbor additional pathogens such as *Babesia microti* simultaneously which can make diagnosis of LB more challenging. Studies indicate that 66% of residents of Long Island, New York diagnosed with LB were also seropositive against *B. microti*. Withstanding the challenges presented, novel LB detection methods are under development. Strategies include metabolomics, interferon-release assays, chemokine assays, xenodiagnositics, and proteomic markers.

Example 1-4: Treatment

With a diagnosis in hand, antibiotics are effective for treating most LB infections. The majority of patients experience a resolution of symptoms after twice-daily doses of oral doxycycline, amoxicillin, or ceftriaxone for 2-4 weeks. Intravenous delivery of ceftriaxone for 30 days is required if there is evidence of CNS dissemination. In addition, a single prophylactic dose of doxycycline can prevent LB development if administered after the discovery of an *Ixodes* tick feeding for >24 hours in LB-endemic locations. In 7-30% of LB patients, antibiotic treatment leads to a transient Jarisch-Herxheimer reaction (JHR) with marked signs of inflammation and elevated C-Reactive Protein (CRP) during the first 10 days of treatment.

Example 1-5: Post-Treatment Lyme Disease Syndrome

Chronic fatigue and musculoskeletal symptoms have been reported after the conclusion of antibiotic therapy treating LB. These patients are characterized within the broad and controversial category of Post-Treatment Lyme Disease Syndrome (PTLDS). Patients with PTLDS and a recurrent EM have been diagnosed with a re-infection from a second tick-bite via Bb genomic polymorphism sequencing. For other cases of PTLDS lacking an EM, further doses of antibiotics are not effective in relieving symptoms.

Prominent theories attempting to explain the discrepancy in LB antibiotic-refractory symptoms include: Bb OspA inducing cross-reactive autoimmunity towards the HLA-DRB1*0401 allele, components of Bb persisting near cartilaginous tissue leading to persistent inflammation, or a low level of persistent infection post-antibiotic treatment as indicated in murine and primate LB models.

In a recent case report, a biofilm has been histologically associated with Bb in human heart, kidney, liver and brain. This Bb biofilm was surrounded by infiltrating lymphocytes and stained positively for the specific biofilm marker alginate. The subject of the case report suffered from pericarditis, decreased cognitive function, and lymphocytic pleocytosis among other complications of disseminated LB. The 39-year-old subject's infection was refractory to multiple rounds of IV antibiotics. A Bb biofilm could explain the persistence of symptoms in the patient's clinical history. Another case report has also demonstrated intact Bb staining on CNS autopsy histology.

In a small cohort of PTLDS patients an increase non-specific antibody responses directed against neural antigens. In a larger cohort of patients, PTLDS patients were found to have a statistically significant increase in the antibodies reactive to OspA (P31) compared to patients that remained symptom free after completing antibiotic therapy.

The current two-step diagnostic protocol cannot discriminate between a previous vs a new or refractory LB infection. This makes the characterization and treatment of PTLDS challenging. A novel diagnostic tracking the resolution of disease would better characterize a PTLDS patient's response to treatment and shed new light on this divisive topic.

Example 1-6: A Crash-Course on Glycans

Glycans are linked monosaccharides conjugated to proteins and lipids in a stepwise post-translational fashion within the ER and Golgi apparatus. Glycans decorate over 70% of human proteins. Asparagine N-linked and serine/threonine O-linked glycans are small molecules that can be harvested from their glycoconjugates and characterized via high-performance liquid chromatography (HPLC) and mass spectroscopy (MS). Glycans comprise a diverse range of configurations and can undergo further chemical modifications such as acetylation or sulfation. In health, glycans participate in biochemical processes such as cell communication, cell-cell interactions, cell recognition, and fertilization. During disease, changes in glycosylation can drive metastatic properties, promote autoimmunity, and alter the effector function of antibodies.

Large scale sera glycome screening combined with glycoproteomics and novel analytical technologies allow for identification of disease-associated biomarkers. For example, the detection of altered core 1,3-fucosylation of alpha-1-anti-trypsin serves as a diagnostic for early forms of Hepatocellular carcinomas.

Examples 1-7: Diagnostics Under Development—Where Glycans Can Help

Lymphocyte Transformation Test (LTTs) were developed in 2012 using various antigens from Bb and other closely related species of *Borrelia* and was found to have a sensitivity of 89% and a specificity of 98%.

Direct study of LB's effect on the human sera glycome has not been accomplished. Therefore, the following genomic, proteomic, and metabolomic studies offer support for the application of glycoproteomic research to LB.

A longitudinal transcriptome analysis of 29 LB patients revealed specific changes in gene expression during the first 3 weeks of infection. Four of the six independently verified proteins altered during early LB [C9, CRP, CST6, PGLYRP2] are N-glycosylated. In a separate study, acute phase markers measured from the serum of untreated acute LB patients revealed elevated levels of CRP, Serum amyloid A, and T-cell specific mediators which correlated to elevated liver enzymes. Yet another group identified acute phase proteins CRP, complement component 9, and trypsin inhibitor heavy chain 2, from human sera via MStern blotting-based serum proteomics. The increased levels of Interleukin-1 receptor accessory protein, Serum amyloid A-1, and Serum amyloid A-2 were found in disseminated LB sera which proved to be predictive in quantifying the stage infection. Furthermore, a multi-omic analysis of the murine macrophage response to Bb led to the downregulation of the glycosylated CD180 protein and an altered metabolic phenotype. All the proteins identified should be analyzed to determine if their associated N-glycan structures are modified in a specific manner in response to the Bb infection. For example, CRP is differentially induced as a glycosylated molecular variant in response to specific disease states such as Tuberculosis. It was expected that Bb would induce a specific CRP glycosylation pattern during early disease.

Akin to changes in protein levels, acute LB alters eicosanoid, bile acid, sphingolipid, and carnitine host metabolic pathways as indicated from human sera and urine. Specific metabolite signatures were also identified comparing PTLDS vs non-PTLDS sera. Glycan synthesis pathways respond to altered metabolic and/or inflammatory states. Therefore, the perturbation of host cellular metabolism supports the rationale for the detection of altered glycans in early LB, disseminated LB, or PTLDS.

Bb itself is also no stranger to the world of human glycans. For example, patients deficient in Mannose-Binding Lectin (MBL) complement pathway were at higher risk to develop disseminated LB. Lectins recognize specific glycan groups. Thus, a defective MBL complement pathway not clearing the Bb infection highlights just one of the roles that glycans play during LB.

Many of the Bb adhesins target N-glycosylated extracellular proteins including decorin, aggrecan, integrin, and plasminogen. LB arthritis severity was increased in a murine model deficient in the lysosomal beta-glucuronidase responsible for clearing glycosaminoglycans (GAGs). Therefore, a Bb infection appears to promote the turnover of glycosylated products in the synovium during disseminated disease. Transcriptomic analysis also revealed increased glycosaminoglycan/proteoglycan-biding activity by Bb during CNS tissue colonization in a primate model. It was expected that the buildup of these glycosylated proinflammatory GAGs in synovium can be detected in human sera and be utilized as a marker of disseminated LB. It was also expected that a cellular response to the binding of Bb adhesins to extracellular proteins would lead to an alteration in host-glycosylation during infection.

Glycan Immunoglobulin Modulation Applications

In addition to glycans serving as acute-phase biomarkers, studies have implicated the alteration of glycans on Immunoglobulin Fc regions to the modulation of immune responses in cancer and autoimmune disorders. Examples of glycosylation of immunoglobulins promoting aberrant disease include Rheumatoid Arthritis via IgG, IgA Nephropathy, and IgE-induced anaphylaxis. Myriad of factors can affect B-cell glycosyltransferase activity during antibody production; 'fine-tuning' the immune-cell receptor downstream signaling towards either a pro- or anti-inflammatory pathway.

Thus, in contrast to the first goal of early detection, the glycosylation pattern on IgG or IgM may allow clinicians to track their patient's response to LB treatment. It was expected that PTLDS patients would gain insight into the source of their symptoms via analysis of their immunoglobin glycosylation patterns as well.

Example 1-8

Glycomic analysis of human sera brings fresh potential to LB diagnostics at the acute infection and post-treatment stages. The analytic technologies required to interrogate glycans in human sera have been validated in cancer and autoimmune disease. Proteomic studies of LB have identified N-glycosylated targets in acute LB sera. Lastly, analysis of the Fc portions of IgM and IgG glycans may have the potential to track immune response during treatment or disease reactivation in PTLDS.

Example 2: Glycoproteomic Approach to Lyme Disease Diagnostics

In Example 2, evidence that altered glycosylation of immunoglobulin G and M (IgG, IgM) has great potential as a diagnostic and prognostic biomarker for Lyme disease (LD) will be presented. The technological basis of the approach is glycomics coupled with liquid chromatography and electrospray ionization mass spectrometry (LC-ESI-MS).

This diagnostic test uses less than 50 μL of patient serum. In general, in this test, total immunoglobulins are purified, and the N-linked sugars are enzymatically released, labeled, and identified. Glycan moieties that change with LD are quantitated (UPLC-ESI-MS) and subjected to an algorithm trained on previous data sets. A positive result indicates an active acute LD infection. In addition, the test can detect patients who responded to antibiotic therapy. In response to our survey of patient and clinician needs, we address the current diagnostic deficiencies for acute LD with our diagnostic.

Advantages of the glycan-based diagnostic include, but are not limited to: (i) detect acute LD biomarkers before seroconversion, (ii) accurately confirm acute LD in patients with a history of previous LD infections, (iii) track therapeutic outcomes, (iv) discriminate EM (+) STTT (–) acute LD from healthy endemic controls, late-stage LD, and other 'mimic' inflammatory diseases, and (v) detect acute LD with higher sensitivity than current two-tiered diagnostics. This concept paper presents promising preliminary data for each stated claim.

Advantages of the technology include, but are not limited to: (i) adapts existing clinical mass spectrometry instruments to run high-throughput Lyme disease diagnostics, (ii) assays require small volumes of serum, and (iii) the assay produces highly reproducible results.

To the best of the inventors' knowledge, GlycoLyme is the first approach that uses serum glycomics coupled with LC-ESI-MS to diagnose acute LD. Because ESI-MS is considered a routine diagnostic tool in clinical laboratories, the herein test could quickly be adapted to high-throughput workflows. Glycomics is expanding the possibilities of diagnostics in multiple fields. Because glycosylation is a dynamic process it can be used to monitor disease progression and personalize medicinal treatments.

Example 2-1: Description of Solution

Direct testing for LD is elusive because the spirochete has a limited presence in the bloodstream. Thus, testing has historically relied on indirect methods of detection, specifically *Borrelia burgdorferi* (Bb)-reactive antibodies.

The present study observed that symptoms of acute LD include swollen lymph nodes, indicating that the lymphatic system is disrupted early in the disease progression before seroconversion occurs. The glycan-based assay detects the lymphatic system's response to the disseminating spirochete's modulation of the immune system. The present study studied this immuno-modulation by assaying the N-glycome of circulating IgG and IgM. It is worth nothing that the test herein does not rely on detecting seroconversion or *Borrelia*-specific IgG or IgM. Instead, the test analyzes the global or total immunoglobulin glycosylation profile.

IgG and IgM serum glycoproteins are produced by B cells in the lymph nodes and play an important role in the LD immune response. Both immunoglobulins contain tightly regulated N-linked glycans. Moreover, antibody glycosylation affects antibody function and can reflect acute and convalescent disease states.

Figure 1:
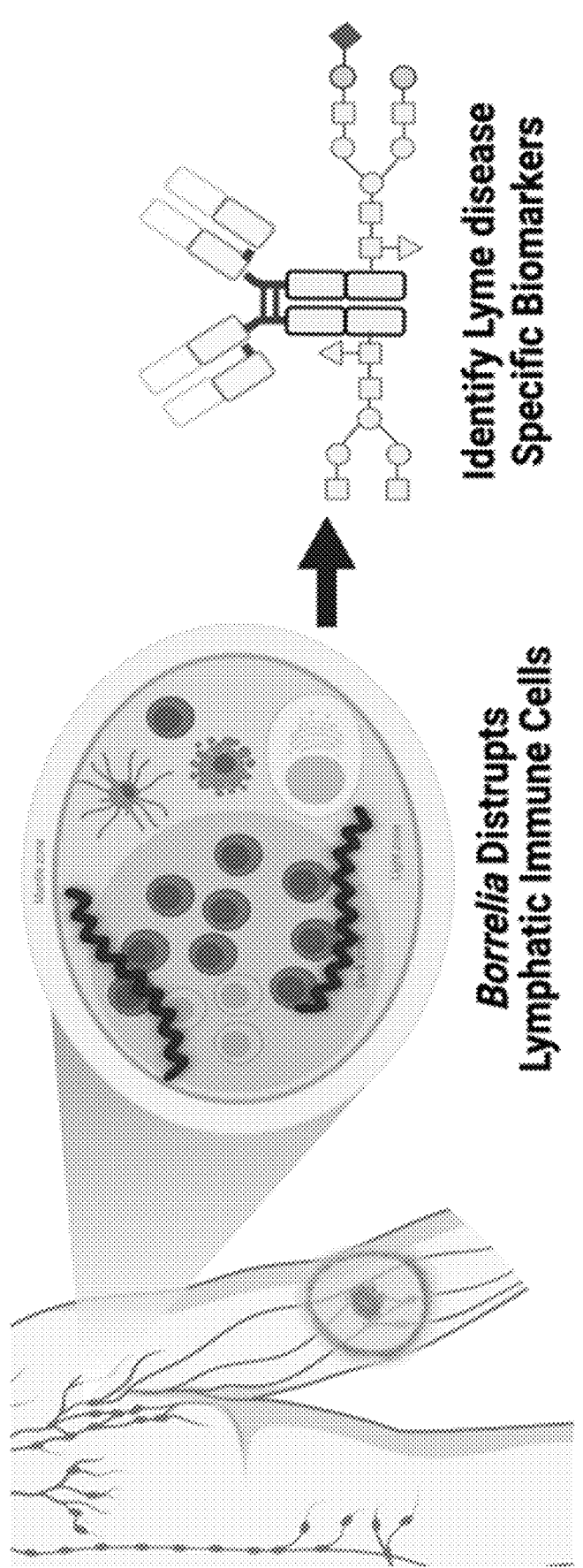
FIG. 1 is a diagram illustrating certain aspects of analyzing N-glycans on IgM and IgG from acute Lyme disease serum revels lymphatic system immuno-modulation, in accordance with some embodiments.

Because Bb invades the lymphatic system during acute LD and ultimately disrupts the antibody-producing germinal centers in the lymph tissue, it was hypothesized that the invasion of the lymphatic system by *Borrelia* would have a global impact on the glycosylation status of IgG and IgM (FIG. 1). This approach is based on the B cell perturbance and circumvents the need to wait for patient's Bb-specific seroconversion.

During infection, the pathogen induces transcription factors that regulate cellular glycosyltransferases, resulting in altered glycan moieties. Small glycans occupy IgG during most inflammatory conditions to promote immune activation by lowering steric hindrance to binding downstream cellular receptors. Inflammatory diseases normally show a trend for global IgG N-glycans to reduce galactose and sialic acid content. Surprisingly, acute LD IgG N-glycans increase their galactose and sialic acid content. Accordingly, the present glycan-based approach diagnoses acute disease while also identifying immuno-modulation that reduces the host's ability to clear a *Borrelia* infection.

Example 2-2: Initial Validation Data

Figures 2A, 2B:
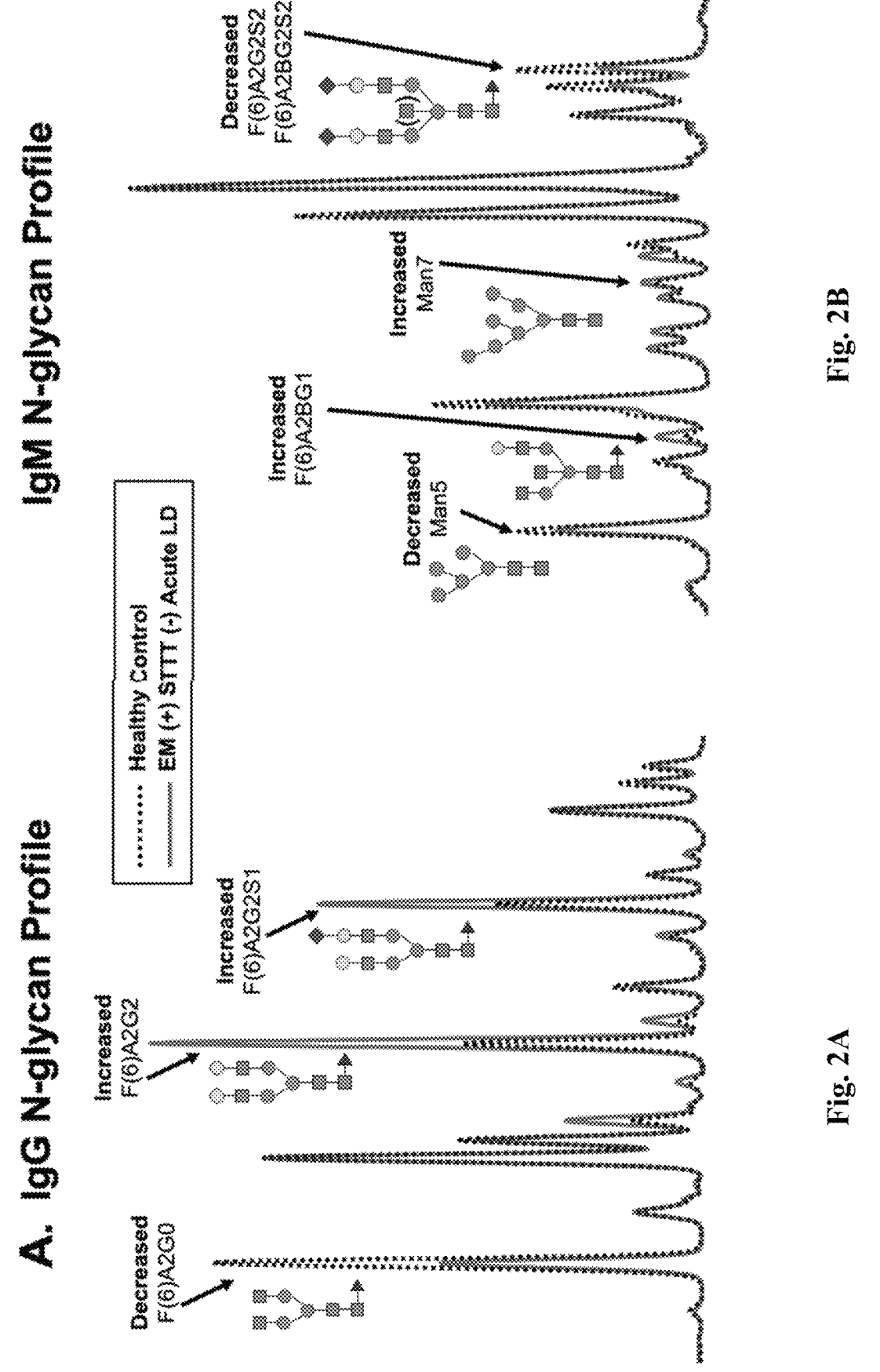
FIGS. 2A-2B demonstrate that cute LD IgG and IgM N-glycan chromatograms significantly differ from healthy controls, in accordance with some embodiments. N-glycans were enzymatically released from total IgG (FIG. 2A) and total IgM (FIG. 2B) purified from patient serum. N-glycans were fluorescently tagged and separated using column chromatography. Each peak presented represents a species of N-glycan. N-glycans identities were confirmed by mass spectrometry. The overlaid N-glycan profile peaks that discriminate between acute LD and healthy controls are indicated with arrows with respective structures presented to the left of each arrow. Samples presented were derived from the CDC Panel 1 serum set.

Patient sample sets were curated by The Bay Area Lyme Foundation and the CDC Lyme disease serum repository Panel 1. The preliminary data was generated in the Comunale Lab at Drexel University College of Medicine using UPLC-ESI-MS. Each glycan was quantitated by calculating the peak area as a percent of the total (FIGS. 2A-2B).

N-glycans are complex sugar structures that are covalently linked to many circulating proteins. Depending on the state of the immune system, different N-glycans species occupy specific sites on immunoglobulins. These N-glycans impact protein function due to the steric hindrance (varied size and charge) for protein binding partners. For example, IgG Fe tails with bulky, negatively charged N-glycans is blocked from binding lymphocyte receptors to signal for inflammation. Only one of 24 glycans can occupy the single glycosylation site on the heavy chain of IgG and one of 6 mannose glycans or 24 complex glycans can occupy the five IgM glycosylation sites. The high degree of N-glycan variability during immune responses allows for multiple biomarkers to identify and track disease states. To analyze glycoprotein N-glycan composition, the N-glycans were released from purified proteins using an enzyme and separate the N-glycans by size using chromatography (FIGS. 2A-2B).

It was demonstrated that the glycan-based assay can detect acute Lyme disease biomarkers before seroconversion. Chromatograms of N-glycans released from total IgG and IgM are presented in FIGS. 2A-2B. Arrows label multiple N-glycans that specifically increase or decrease in abundance during EM (+), STTT (–) acute Lyme disease from the CDC Research Panel 1. IgG contains significantly more galactose and sialic acid (FIG. 2A) while IgM increases the length of the mannose N-glycans and loses di-sialylated N-glycan structures (FIG. 2B). These N-glycan profiles are not canonically associated with inflammatory disease responses and suggest immuno-modulation occurs as the *Borrelia* spirochete interacts with the lymphatic system. By combining the observed abundance shifts in the N-glycan profiles of IgG and IgM, we propose that N-glycans represent an early biomarker of immuno-modulation in response to acute Lyme disease (See FIGS. 4A-4B for more details).

It was demonstrated that the glycan-based assay can accurately confirm acute LD in patients with a history of previous LD infections. FIGS. 3A-3B compares the increase of IgG di-galactose N-glycan content in acute Lyme disease patients. There are no statistically significant differences between acute LD patients infected for the first time (n=9 middle bar) compared to those who were infected with LD previously (n=9 right bar). Therefore, the biomarkers for immuno-modulation observed during acute LD can be detected each time a patient is re-infected with acute LD. This is in direct contrast to the current STTT testing paradigm wherein it is unclear if a patient with a previous history of LD has already seroconverted or is responding to the reinfection. As such, the test herein is able to add clinical value and help clinicians treat patients faster with confidence independent of LD infection history.

The present study demonstrated that the glycan-based assay herein can track therapeutic outcomes. Patients with EM (+), STTT (+) acute LD returned to donate a serum after completing 10-21 days of antibiotic treatment and 70-90 days of convalescence. None of the 18 patients returning to the clinic reported symptoms that suggested they had Post-treatment Lyme disease Syndrome (PTLDS). The treated LD patient IgG N-glycans contain significantly more bisecting GlcNAc (highlighted in a circle, FIG. 3B). Bisecting N-glycans on IgG is associated with a pro-inflammatory response and suggests the host's immune system is responding to the antibiotic treatment for acute Lyme disease.

It was demonstrated that the glycan-based assay can discriminate EM (+) STTT (–) acute LD from healthy endemic controls, late-stage Lyme disease, and other 'mimic' inflammatory diseases. Patient N-glycan profiles from total IgG and IgM were scored using set thresholds for each discriminating N-glycan. If the patient's IgM N-glycans met 3/5 discriminating thresholds or 4/5 of the IgG N-glycan thresholds, the patient scored as a "positive" acute LD case. The present study applied this discriminating algorithm to the data set from the CDC Lyme disease Panel 1 and determined that 4 of the 4 EM (+) STTT (–) patients scored positive on the assay (second bar on the left, above the dotted line, FIG. 4A). Both endemic and non-endemic healthy controls (black bar) scored negative for a positive acute LD diagnosis, as did the numerous mimic diseases provided by the CDC (right six bars). Interestingly, acute Lyme disease patients that were deemed seropositive at their convalescent serum draw were no longer positive for acute Lyme disease on the glycan-based assay (third bar on the left). Lastly, late-stage Lyme disease such as Lyme neuroborreliosis or Lyme arthritis (fourth and fifth bars on the left, respectively) were not positive according to the glycan-based acute Lyme disease glycan-based assay. These data support our theory that *Borrelia* infection induces a specific immuno-modulation of total immunoglobulin N-glycans before seroconversion occurs. Using the UPLC-FLR-ESI-MS method, acute LD cases can be accurately identified before traditional serology assays and the resolution of immuno-modulation can be tracked via a convalescent time point.

It was further demonstrated that the sensitivity of the glycan-based assay is higher than conventional acute Lyme disease diagnostics. The Bay Area Lyme disease Foundation samples set provided 18 healthy endemic controls and 18 EM (+) STTT (+) acute Lyme disease patients. By combining total IgG and IgM N-glycan profiles, the present study discriminated between endemic healthy control and acute LD serum with a sensitivity of 72% and a specificity of 100% (conventional two-tiered testing for acute Lyme disease sensitivity is ~46%) (FIG. 4B). Therefore, the glycan-based assay herein is able to significantly improve the number of patients that are diagnosed with acute Lyme disease. Specific patient populations that would benefit from the glycan-based assays are those that previously tested positive for LD who have become re-infected, patients with a skin pigmentation that obscures the classic EM rash, and those patients who wish to track their response to treatment over time.

Example 2-3: Use of GlycoLyme

General Use:

The GlycoLyme test is intended as a qualitative measure of aberrant total IgG and IgM N-glycans in human serum from symptomatic patients with suspected acute *B. burgdorferi* infection.

The GlycoLyme test can be prescribed by a clinician at the initial visit to confirm the diagnosis of acute LD and to ensure the patient has a baseline for monitoring treatment efficacy. Subsequent tests should be conducted to confirm treatment response or upon subsequent infections.

The GlycoLyme test is intended to be used in conjunction with antibody titers for suspected acute LD re-infections. The glycan profile will indicate an active infection and will be used to monitor treatment responses.

The assay is also intended to be used as a second-tier confirmation test following a positive first-tier test using VlsE-OspC IgG/IgM ELISA.

Predicted Outcome of Use:

The test provides patient centeredness in that the patient will be able to have (i) confirmation that the treatment is working or (ii) a metric that will correlate their continued and unresolved symptoms with a test result. Subsequent tests are administered following treatment as needed and compared to the results of the initial visit.

The test provides the treating clinician with a test result that informs on antibiotic effectiveness and guide treatment decisions.

Example 2-4

Lyme Disease is on the Rise

With the rates of LD climbing, it is crucial to have accurate diagnostics that can detect an acute LD infection. In addition to the percent of ticks infected with *Borrelia burgdorferi*, climate change is causing an increase in the hospitable tick habitat and altered deer populations.

Undiagnosed LD Quickly Disseminates into the Host Organs, Making Treatment More Difficult When acute LD goes untreated, the spirochete disseminates into synovial, cardiac, and neuronal tissue resulting in chronic disabilities and, in severe cases, death. Pregnant women who do not receive treatment have experienced multiple adverse pregnancy outcomes including, preterm delivery, stillbirth, and congenital cardiac malformations. In addition, children's hospitals report increased Lyme carditis in minors. These disseminated cases of Lyme disease would be prevented by an accurate diagnostic to catch the acute stage of disease, when a two-to-three-week course of antibiotics effectively treats patients. Due to the low sensitivity of the current acute Lyme disease diagnostic, patients with Lyme disease are often missed as "false negatives."

Early Diagnosis Means Lowered Disease Burden

The GlycoLyme test improves sensitivity and minimizes false negatives, significantly reducing disease burden. By lessoning the long-term cost of disseminated disease in disability-adjusted life years (number of years lost due to ill-health, disability, or early death) the endemic population will show measurable improvements in 'healthy' life lost by virtue of being in states of poor health.

Example 3: Acute Lyme Disease IgG N-Linked
Glycans Contrast the Canonical Inflammatory
Signature Lyme disease (LD) infection is caused by *Borrelia burgdorferi* sensu lato (Bb). Due to the limited presence of this pathogen in the bloodstream in humans, diagnosis of LD relies on seroconversion. Immunoglobulins produced in response to infection are differentially glycosylated to promote or inhibit downstream inflammatory responses by the immune system. Immunoglobulin G (IgG) N-glycan responses to LD have not been characterized. The present study analyzed IgG N-glycans from cohorts of healthy controls, acute LD patient serum, and serum collected after acute LD patients completed a 2- to 3-week course of antibiotics and convalesced for 70-90 days. Results indicate that during the acute phase of Bb infection, IgG shifts its glycosylation profile to include structures that are not associated with the classic proinflammatory IgG N-glycan signature. This unexpected result is in direct contrast to other inflammatory diseases. Furthermore, IgG N-glycans detected during acute LD infection discriminated between control, acute, and treated cohorts with a sensitivity of 75-100% and specificity of 94.7-100%.

In 1975, a cluster of children and adults in the small community of Lyme, Connecticut experienced unusual arthritic symptoms. Today, Lyme disease (LD) is the most prevalent vector-borne disease in the US, with an estimated 476,000 annual cases. The causative agent, *Borrelia burgdorferi* sensu lato (Bb), is a spirochete transmitted from the *Ixodes* tick into the human host dermis during its blood meal. The spirochete leaves the blood and disseminates into multiple organ systems in as little as two weeks postinfection. Disseminated LD is more challenging to diagnose, and delayed treatment can lead to long-term disability or death. The disease is endemic in the Northeastern US, and incidence rates continue to rise. The US's annual treatment and diagnostic cost is ver 4.8 billion USD.

Antibiotic treatment for LD in the acute phase is often curative. However, untreated patients and a subset of treated patients progress to disseminated disease. Disseminated disease can result in facial nerve palsy, Lyme Carditis, Lyme Arthritis, Lyme neuroborreliosis and long-term disability. Persistent symptoms are reported by 10-20% of patients diagnosed and treated during the acute phase of LD. Persistent symptoms include joint pain, fatigue, and neurocognitive deficits. This highlights the need for an accurate early diagnosis and the ability to track disease resolution.

Current diagnosis is complicated because testing relies on indirect methods. Direct PCR and blood culture methods often fail due to the spirochete's limited presence in the bloodstream, low bacterial counts in circulation, slow replication cycle, the requirement for complex growth media, and specialized microscopy requirements. Hence, indirect methods that rely on the patient's serological response are the principal method of confirming an infection. These indirect methods of acute LD diagnostics based on ELISA and western immunoblot technologies suffer from low sensitivity and a high false-positive rate. Thus, while advances in LD detection research are being made, clinicians currently lack a sensitive method to diagnose early disease. Furthermore, clinical assays are unable to determine treatment efficacy, track disease resolution or diagnose subsequent infections.

Serum protein glycosylation is often altered during inflammatory and autoimmune diseases. The glycosylation profile of immunoglobulins is dynamic and offers a novel immunologic insight into the host's response. Glycosylation is the most abundant complex post-translational serum protein modification and plays a significant role in protein structure and function in vivo. IgG has a well-characterized N-glycosylation site on the constant fragment (Fc-Asn-297) region. This site contains complex biantennary glycans with varying degrees of galactose, bisecting N-acetyl-glucosamine, and sialic acid residues. Most notably, the glycans are highly core-fucosylated. IgG glycosylation is dynamic and the glycans present can affect the binding avidity to various Fcg receptors, rate of complement activation, and release of cytokines. Previous studies have profiled IgG N-glycans in sera obtained from patients with inflammatory disease (FIG. 5). Reports indicate a trend for IgG N-glycan reduction in terminal galactose and sialic acid content during inflammatory diseases and this glycan signature is linked to a pro-inflammatory phenotype.

IgG glycosylation moieties are associated with specific functions. In general, lowered galactose and sialic acid residue content are reported in inflammatory states (FIG. 9), and conversely, increased galactose is associated with an anti-inflammatory state. Hence, to improve immunotherapy outcomes, pharmaceutical companies glycoengineer monoclonal antibodies with specific glycosylation features to treat cancers and chronic diseases. For example, the effectiveness of intravenous immunoglobulin (IVIG) therapy for autoimmune conditions including Gillian-Barre, Immune Thrombocytopenic Purpura, or Kawasaki disease patients is associated with the increased sialic acid content on the Fc N-glycans of the IVIG. In addition, therapeutic monoclonal antibodies are glycoengineered to contain specific a-fucosylated, agalactosylated N-glycans to promote superior half-life and treatment efficacy. IgG N-glycan modulation of the immune response during disease reveals another layer of physiologic crosstalk. Evidence indicates that the repertoire of N-glycans present on IgG produced in response to vaccines is dependent on many factors, including age, inflammatory state, and the type of adjuvant.

In certain embodiments, the IgG N-glycan profile of LD patients reflects the immunological response to the acute LD infection. Thus, this first report of total IgG N-glycans associated with LD provides insight into the inability of the host immune system to resolve Bb bacterial infection.

Example 3-1: Material and Methods

Patient Samples

Serum samples (FIG. 6) were obtained from the Bay Area Lyme Disease Biobank and stored at −80° C. Serology was determined at Stony Brook University and the Bay Area Lyme Disease Biobank. Human subject research IRB requirements were met (IRB #1808006553). Acute LD patients presented with erythema migrans (EM) rash(es) and donated their blood at the time of clinical diagnosis. Acute LD patients were included in the cohort when their acute LD diagnosis was confirmed using either two-tiered serological studies or PCR identification. Convalescent draws were obtained after patients completed their prescribed course of 14-21 days of antibiotics and convalesced for 70-90 days without further symptoms. the convalescent cohort are referred to as "treated" herein. In the pilot study, serum was pooled into three patient cohorts. Seven healthy controls were pooled, 5 acute LD patients were pooled, and 3 treated LD patients were pooled. The resulting three samples were analyzed within the pilot study using HPLC and the Gly-coTyper MALDI-TOF methods. In the subsequent confirmatory study using the GlycoTyper method, data was collected from each individual patient: healthy control (n=18), acute (n=18), and patient-matched treated (n=18). Further demographic details for the patient cohorts are presented in FIG. 17.

HPLC IgG N-Glycan Analysis

IgG was purified from 5 mL of pooled serum using Protein A/G UltraLink Resin (Thermo Scientific, MA) according to the manufacturer's directions. IgG Heavy Chains (Fc region) were isolated using 1D gel electrophoresis, stained with Coomassie stain and the 50 kDa band was excised. Following gel de-staining, the glycans were enzymatically removed and fluorescently labeled following standard in-gel PNGase F and labeling protocols as described in Comunale et al. (*J Proteome Res* (2009) 8(2):595-602. doi:10.1021/pr800752c) and Comunale et al. (PloS One (2010) 5(8):e12419. doi: 10.1371/journal.pone.0012419). The labeled N-glycans were combined with 100% Acetonitrile (30:70) in an HPLC-compatible vial. Fluorescently labeled glycans were subsequently analyzed by high-performance liquid chromatography (HPLC) by using a TSK-Gel Amide 80 column (Tosoh Bioscience LLC). The mobile phase consisted of solvent A (50 mmol/L ammonium formate, pH 4.4) and solvent B (acetonitrile). The gradient used was as follows: a linear gradient from 20% to 58% solvent A at 0.4 mL/min for 152 min followed by a linear gradient from 58% to 100% solvent A for the next 3 minutes. The flow rate was increased to 1.0 mL/min, and the column was washed in 100% solvent A for 5 minutes. Following the wash step, the column was equilibrated in 20% solvent A for 22 minutes in preparation for the next sample run. HPLC analysis was performed using the Waters Alliance HPLC System, complemented with a Waters fluorescence detector, and quantified by the Millennium Chromatography Manager (Waters Corporation). Glycan structures were identified by calculating the glucose unit and GlycoStore database as described in Guile et al. (*Anal Biochem* (1996) 240(2):210-26. doi: 10.1006/abio.1996.0351). The HPLC method overview is provided in FIG. 13A.

Removal of Sialic Acids for HPLC and MALDI Comparison

Due to the inherent challenges of detecting glycans containing sialic acid using mass spectrometry, HPLC data was collected using samples that were desialylated to allow a direct comparison with the MALDI-FT-ICR method. Beginning with 13 mL of the labeled and chromatographically cleaned 2-AB glycans, 4 mL 5× pH 6.0 Enzyme Buffer was added before pipette mixing 3 mL of Sialidase A (ProZyme (now AdvanceBio), OH). The 20 mL final volume was incubated at 32° C. for 12 hours. Next, the 20 mL solution was added to a 10K MWCO concentrator column (Corning, NY) and centrifuged at 12,000 rpm for 10 minutes. The flow-through was collected and combined with an additional 25 mL of dH₂O before being added back to the 10K MWCO column and centrifuged at 12,000 rpm. This process of collecting the flow-through and combining it with additions of 25 mL dH₂O was repeated to serially enrich the labeled N-glycans while filtering out the sialidase enzyme. The sample was subsequently dried down via SpeedVac holding a vacuum at −28 in Hg without added heat and re-suspended in 30 mL dH₂O. Sialidase-treated samples were then analyzed as outlined for non-sialidase-treated sample in HPLC.

MALDI-FT-ICR Mass Spectrometry N-Glycan Analysis

SolarisX Legacy 7T FT-ICR mass spectrometer equipped with a Matrix-Assisted Laser Desorption/Ionization (MALDI) (Bruker) analysis of total IgG N-glycans is detailed in the literature. In brief, 1 mL serum diluted in 99 mL 1×PBS was incubated with 0.2 mg/ml spotted anti-IgG capture antibodies (Bethyl Laboratories Inc., Tx, Cat. Number A80-104) treated with Sialidase A (produced in-house by MUSC), sprayed with PNGase F (produced by N-Zyme, PA) to release N-glycans from captured targets, coated with a matrix, and analyzed for glycan abundance at specific m/z peaks by MALDI-FT-ICR MS using SCiLS Lab software 2022a (Bruker). A capture antibody treated with PBS served as a blank to subtract the N-glycans released from the capture antibody from the final analysis. A MALDI-FT-ICR (referred to as MALDI) method overview is provided in FIG. 13B and is also referred to as the "GlycoTyper" method.

Statistical Analysis

One-way ANOVA analysis with post-hoc Tukey's multiple comparisons test was employed to examine the triplicate datasets for statistically significant differences between cohorts. $P<0.05$ was considered statistically significant and figures are denoted as having $*p<0.05$, $p<0.01$, $*p<0.001$. Figures and statistical analysis were completed using GraphPad Prism 8. Receiver Operating Characteristic (ROC) curves analyzed individual N-glycan abundance levels for diagnostic utility. Results are described using the Oxford nomenclature (Harvey et al., *Proteomics* (2009) 9(15):3796-801. doi:10.1002/pmic.200900096).

Example 3-2

The present study demonstrates that total serum IgG N-glycosylation of acutely infected Lyme disease patients contrasts with the typical pro-inflammatory signature often found on other inflammatory diseases. First, a proof-of-concept study was performed using pooled serum to identify the IgG N-glycan signature of healthy control, acute LD, and patient-matched antibiotic-treated LD serum using high-pressure liquid chromatography separation (HPLC) and detection of fluorescently labeled glycans. The samples were subsequently analyzed using the recently developed Glyco-Typer MALDI method (Black et al., *Curr Protoc Protein Sci* (2019) 98(1):e99. doi: 10.1002/cpps.99) which pairs a specific total-IgG capture antibody with subsequent MALDI-FT-ICR imaging (MALDI). The trends in the glycan signatures were reproducible between both platforms, and thus the present study proceeded to analyze a larger confirmatory set of individual serum samples using the GlycoTyper platform.

Example 3-3: Acute LD IgG N-Glycans Gain Terminal Galactose and Sialic Acid

HPLC analysis of the glycan signature revealed several statistically significant differences between control and acutely infected patients (FIGS. 7A-7B). Individual glycans were quantitated as a percent of the total glycan profile and compared across cohorts using one-way ANOVA (FIG. 7A). Two agalactosylated glycan species, F(6)A2G0 and F(6)A2BG0, decreased in the acute and treated pooled cohorts when compared to controls. There was also an observed decrease in the mono-galactosylated F(6)A2G1 glycan. In addition, significant increases in three glycan species were observed. N-glycans containing terminal di-galactose, with and without core fucose increased significantly (A2G2, F(6)A2G2), as did the core fucosylated mono-sialylated glycan (F(6) A2G2S1). Next, the abundance of IgG N-glycans with specific characteristics were summed to analyze the glycans by class. IgG N-glycans containing bisecting GlcNAc, core-fucose, no galactose, a mono- or digalactose, or a mono- or di-sialylated were respectively summed to present N-glycan class data (FIG. 7B). The decrease in the smaller agalactosylated class and an increase in the terminally galactosylated and sialylated glycans was observed. However, bisecting and core-fucosylated N-glycan classes did not significantly vary across cohorts. The only statistical difference observed between the acute and treated patient cohorts was a continued increase in the presence of terminal galactose.

Example 3-4: MALDI-FT-ICR and HPLC Detect Similar Trends of IgG N-Glycans in LD IgG N-glycans were desialylated and the HPLC analysis was compared to the MALDI-FT-ICR method. The IgG N-glycans were grouped by terminal sugar moiety into 4 glycan classes. These groups showed the same trends using both platforms (FIGS. 8A-8B). Significant reductions in agalactosylated N-glycans and significant increases in terminal galactose were identified in the HPLC (FIG. 8A) and MALDI glycan analysis platforms (FIG. 8B). Both methods indicate there is no significant difference in the abundance of bisecting or core-fucosylated N-glycans when comparing controls, acute and treated patient cohorts. The reproducible shifts in IgG N-glycan abundance within the desialylated glycan classes promoted the use of a larger confirmatory set of LD serum to be analyzed in a high-throughput manner using the MALDI method.

Example 3-5: MALDI Analysis Identifies IgG N-Glycosylation Signatures of Patients with LD IgG N-glycans from a confirmatory set of healthy control, acute LD, and acute re-drawn serum post-antibiotic treatment patient sera were examined. MALDI analysis of the desialylated IgG N-glycans identified statistically significant shifts of N-glycan species (FIGS. 9A-9B). Several significant differences were detected when comparing control and acute LD. Acute LD patients exhibit a significant decrease in the core fucosylated agalactosylated N-glycan F(6)A2G0 when compared to controls (FIG. 9A). Conversely, there was a statistically significant increase in the core fucosylated di-galactosylated N-glycan F(6)A2G2. IgG N-glycans terminating in total galactose or digalactose significantly increased during acute LD compared to healthy controls (FIG. 9B). There was no significant difference in the total bisecting or core-fucosylated N-glycans when comparing Acute to healthy control IgG.

The present study observed a continued perturbation of IgG glycosylation in the post-treatment cohort that does not return towards healthy control baselines for many detected N-glycans. Treated LD patients maintained a significant decrease in the agalactosylated F(6)A2G0 observed in acute LD (FIG. 9A). An additional significant drop was seen in two glycan structures, F(6)A2G1 and F(6)A2BG2, when compared with control and acute. Several glycans showed significant increases. Increases that were limited to the treated cohort include the A2G1 and F(6)A2BG1 structures. The F(6)A2G2 continued to increase above the already elevated acute LD cohort level. Grouping the treated timepoint IgG N-glycans revealed a drop in total core-fucose as well as a decrease in the digalactosylated grouped N-glycans (FIG. 9B). There was no difference observed for the total bisecting N-glycans between acute and treated timepoints.

These findings align with previous assays from the pooled pilot study experiments. Comparisons of IgG N-glycosylation dependence on age, sex, location of collection, or ethnicity were assessed. There was no statistically significant difference within or between cohorts when applying these metrics (data not shown) with one exception. Healthy control males had 2.3% higher F(6)A2G0 N-glycan profiles compared to their healthy control female counterparts. While IgG N-glycan signatures change during ageing and between sexes, the age- and sex-matched cohorts permitted comparisons across and between the cohorts.

Example 3-6: IgG N-Glycans Discriminate Between Healthy Control and LD Timepoints Seroconversion is often employed as a LD diagnostic, yet there is great need for a more sensitive, early indicator of disease. Moreover, serological assays for LD cannot differentiate between a patient with acute LD compared to a patient that has recently convalesced from LD. FIG. 10 reports the efficacy of selected IgG N-glycans to discriminate between healthy and LD patient cohorts. Thresholds for listed N-glycan classes were determined using receiver operating characteristic (ROC) curve. The performance of the discrimination was reported in a confusion matrix (FIGS. 14-16). Healthy controls are differentiated from acute serum samples using four N-glycan classes: F(6)A2G0, F(6)A2G2, percent total terminal galactose, and percent terminal di-galactose; resulting in 75% sensitivity, 100% specificity, and 85.7% accuracy. Healthy controls are differentiated from treated LD patient serum using the N-glycan classes: F(6)A2G0, A2G1, F(6)A2G1, F(6)A2G2, F(6)A2BG2, percent total fucose, and percent total terminal galactose; resulting in 100% sensitivity, 94.7% specificity, and 97.3% accuracy. Lastly, acute LD serum is differentiated from the treated serum using the N-glycan classes: A2G1, F(6)A2G1, F(6)A2G2, F(6)A2BG1, F(6)A2BG2, total percent fucose, and percent G2 galactosylation; resulting in 100% sensitivity, specificity, and accuracy.

Example 3-7: Lyme Disease Subverts IgG Response-Working Hypothesis

Results presented in FIG. 10 show the increased terminal galactose observed on IgG N-glycans detected during LD within the context of the humoral immune response. IgG N-glycans detected in acute LD patients contain significantly higher levels of galactose and conversely lower agalactosylated structures. Most IgG N-glycans responding to inflammatory diseases present increased agalactosylated N-glycans to promote downstream pro-inflammatory immune responses. Thus, the LD IgG N-glycans may be induced through the *Borrelia burgdorferi*'s disruption of the germinal center and antibody response.

Example 3-8

This is the first report of total human IgG N-glycan profiles during early and treated LD. The initial studies detected an unanticipated shift in IgG N-glycan profile which was confirmed and expanded upon using a larger set of samples. During many inflammatory states (FIG. 5), IgG N-glycan profiles respond with reduced terminal sialic acids and galactose and increased GlcNAc sugar exposure. This agalactosylated IgG phenotype has been demonstrated to promote pro-inflammatory responses and may aid in clearing the infection. In the case of LD, total IgG N-glycan profiles had the opposite trend. LD increases the galactose and sialic acid content of IgG N-glycans while further decreasing the terminal GlcNAc exposure (FIGS. 7A-10). The result of such a shift requires further investigation, but in theory could contribute to ineffective host responses to LD infection by reducing humoral immune activation. The ability to detect these changes within total IgG suggests that LD induces a large shift in the IgG N-glycan composition. Thus, this dysregulated immune response may at least in part explain why human IgG produced during an initial LD infection is not effective to clear the current infection or protect from a future re-infection with LD.

The pilot study served to compare the well-established HPLC IgG N-glycan analysis method to the novel MALDI analysis method using pooled cohorts of control, acute LD, and treated LD serum. Due to MALDI's limited detection of unmodified sialic acids, samples were treated with a sialidase. The results presented in FIGS. 8A-8B demonstrate that both methods detect comparable individual identified N-glycans with similar trends of terminal galactose exposure induced during LD and maintained during the post-antibiotic treatment time points. To confirm the pooled pilot study findings, three cohorts of 18 individual samples were analyzed in triplicate using the MALDI method. The Glyco-Typer method was selected to analyze the confirmatory cohort due to its significantly higher throughput compared to HPLC. It was found that the demographics of the age- and sex-matched patient cohorts did not lead to inherent differences in IgG N-glycosylation.

While the MALDI results confirmed the original trends observed in the pooled pilot study, a higher number of samples analyzed led to further trends emerging (FIGS. 9A-9B). Agalactosylated structures are reduced while total N-glycans terminating with a galactose moiety continued to increase within the acute and treated cohorts as indicated within the pooled pilot experiments. N-glycans containing a core-fucose are markedly lowered in the antibiotic-treated cohort which suggests an increase in Antibody-Dependent Cellular Cytotoxicity (ADCC) abilities of post-treatment IgG. The increased level of digalactosylated (G2) N-glycans on IgG at the acute stage and subsequent return to healthy control levels is a potential biomarker reflecting the host's response to successful antibiotic treatment. Following antibiotic therapy for Tuberculosis (TB), IgG N-glycan digalactose content returned to healthy control levels. Grace et al. found G2 N-glycans decreased during acute TB and subsequently increased after effective antibiotic treatment.

In the case of LD, IgG N-glycans increase G2 content during infection and return to healthy control levels after effective antibiotic treatment (FIG. 9B). This once more converse trend observed in LD suggests a subverted immune response during LD compared to TB infection. The implication of the IgG N-glycan response to LD is portrayed in FIG. 11.

LD patients are discriminated from healthy controls with a high degree of sensitivity (75-100%) and specificity (94.7-100%) using total IgG N-glycan measurements (FIG. 10). Blinded analysis of acute LD, post-treatment LD, and mimic diseases using these methods should be completed to validate these findings. Future LD tests incorporating total IgG N-glycan analysis could increase acute LD diagnostic sensitivity and track subsequent antibiotic treatment responses.

Example 3-9

Using the GlycoTyper MALDI-FT-ICR imaging approach, the present study detected an unexpected IgG N-glycan signature in humans during LD. The present study demonstrated the IgG N-glycans produced during a Lyme disease infection lack the classic highly agalactosylated signature associated with most inflammatory diseases. Instead, LD induces IgG N-glycans containing larger, terminally galactosylated sugar moieties. Moreover, many IgG N-glycans detected at the acute LD timepoint remain altered from healthy control levels at the post-antibiotic treatment timepoint. Of note, the digalactose content of IgG N-glycans in the treated time point was comparable to the healthy baseline levels after antibiotic treatment. Furthermore, the present study detected a significant decrease in total core-fucosylation at the treated timepoint suggesting a possible increase in ADCC which may aid in clearing Bb from the host. IgG N-glycans offer numerous biomarkers, reflect acute disease state, response to treatment, and may improve the sensitivity of the acute diagnosis of LD above the current two-tiered testing protocol.

ENUMERATED EMBODIMENTS

In some aspects, the present disclosure is directed to the following non-limiting embodiments.

Embodiment 1. A method of diagnosing Lyme disease in a subject, comprising: determining a glycosylation profile of a protein in the subject, wherein a change of the glycosylation profile of the protein relative to a normal glycosylation profile is associated with Lyme disease; and comparing the glycosylation profile of the protein in the subject with a predetermined first glycosylation profile indicating free of Lyme disease or a predetermined second glycosylation profile indicating Lyme disease.

Embodiment 2. The method of Embodiment 1, wherein the change of the protein glycosylation profile comprises an increased level of glycosylation, or a decreased level of glycosylation.

Embodiment 3. The method of any one of Embodiments 1-2, wherein the change of the protein glycosylation profile comprises an increased complexity of sugar structure.

Embodiment 4. The method of Embodiment 3, wherein the increased complexity of sugar structure comprises decreased level of terminal galactose structures, and/or an increased level of fucosylation, antennary, or sialic acid structures.

Embodiment 5. The method of any one of Embodiments 1-4, wherein the protein comprises at least one selected from the group consisting of Immunoglobulin G (IgG), Immunoglobulin M (IgM), Complement component 9, pentraxin-related C-reactive protein, Cystatin E/M, Peptidoglycan recognition protein 2, Afamin, fructose-bisphosphate Aldolase B, Apolipoprotein A-IV, Apolipoprotein B, Complement factor H related 1, Coagulation factor IX, Fructose-1,6-bisphosphatase 1, Vitamin D-binding protein-macrophage activating factor, Interalpha (globulin) inhibitor H2, Inter-alpha-trypsin inhibitor 4, Platelet factor 4 (CXCL7), S100 calcium binding protein A9, pentraxin-related C-reactive protein, Serum amyloid A-1 protein, C-X-C motif chemokine 9, C-X-C motif chemokine 10, C-C motif chemokine 19, pentraxin-related C-reactive protein, Complement component 9, Interalpha (globulin) inhibitor H2, Kininogen-1, Gelsolin, Interleukin-1 receptor accessory protein, Serum amyloid A-1 protein, Serum amyloid A-2 protein.

Embodiment 6. The method of any one of Embodiments 1-5, wherein the protein comprises at least one selected from the group consisting of IgG, IgM, and total serum protein.

Embodiment 7. The method of any one of Embodiments 1-6, wherein the glycosylation profile of the protein in the subject is compared with at least one of a glycosylation profile indicating acute Lyme disease, a glycosylation profile indicating disseminated Lyme disease, a glycosylation profile indicating a state of recovering from Lyme disease, a glycosylation profile indicating a recovered case of Lyme disease, and a glycosylation profile indicating a non-Lyme infection or inflammatory disease.

Embodiment 8. The method of any one of Embodiments 1-7, wherein the method determines the stage of Lyme disease in addition to the absence or presence of Lyme disease.

Embodiment 9. The method of Embodiment 8, wherein the stage of Lyme disease includes acute Lyme disease, disseminated Lyme disease, state of recovering from Lyme disease, or reinfection with Lyme disease.

Embodiment 10. The method of any one of Embodiments 1-9, further comprises detecting an anti-*Borrelia* antibody in the subject.

Embodiment 11. The method of any one of Embodiments 1-9, wherein determining the glycosylation profile of the protein in the subject comprises at least one selected from the group consisting of: purifying the protein from a sample of the subject and releasing glycans from the protein.

Embodiment 12. The method of any one of Embodiments 1-11, wherein the glycosylation profile of the protein in the subject and/or the predetermined glycosylation profiles are determined by a matrix-assisted laser desorption/ionization (MALDI) mass spectrometry-based method, a high-performance liquid chromatography (HPLC)-based method, or an enzyme-linked immunosorbent assay (ELISA)-based method.

Embodiment 13. The method of any one of Embodiments 1-12, wherein the method diagnoses an acute Lyme disease in the subject before seroconversion.

Embodiment 14. A method of treating and/or ameliorating Lyme disease in a subject, the method comprising: determining a glycosylation profile of a protein in the subject, wherein a change of the glycosylation profile of the protein in relative to a normal glycosylation profile is associated with Lyme disease; comparing the glycosylation profile of the protein in the subject with a predetermined first glycosylation profile indicating free of Lyme disease or a predetermined second glycosylation profile indicating Lyme disease; and if the glycosylation profile of the protein in the subject does not correspond to the first glycosylation profile or the glycosylation profile of the protein in the subject correspond to the second predetermined level, administering to the subject an effective amount of compound effective for treating and/or ameliorating Lyme disease.

Embodiment 15. The method of Embodiment 14, wherein the change of the protein glycosylation profile comprises an increased level of glycosylation or a decreased level of glycosylation.

Embodiment 16. The method of any one of Embodiments 14-15, wherein the change of the protein glycosylation profile comprises an increased complexity of sugar structure.

Embodiment 17. The method of Embodiment 16, wherein the increased complexity of sugar structure comprises decreased level of terminal galactose structures, and/or an increased level of fucosylation, antennary, or sialic acid structures.

Embodiment 18. The method of any one of Embodiments 14-17, wherein the protein comprises at least one selected from the group consisting of Immunoglobulin G (IgG), Immunoglobulin M (IgM), Complement component 9, pentraxin-related C-reactive protein, Cystatin E/M, Peptidoglycan recognition protein 2, Afamin, fructose-bisphosphate Aldolase B, Apolipoprotein A-IV, Apolipoprotein B, Complement factor H related 1, Coagulation factor IX, Fructose-1,6-bisphosphatase 1, Vitamin D-binding protein-macrophage activating factor, Interalpha (globulin) inhibitor H2, Inter-alpha-trypsin inhibitor 4, Platelet factor 4 (CXCL7), S100 calcium binding protein A9, pentraxin-related C-reactive protein, Serum amyloid A-1 protein, C-X-C motif chemokine 9, C-X-C motif chemokine 10, C-C motif chemokine 19, pentraxin-related C-reactive protein, Complement component 9, Interalpha (globulin) inhibitor H2, Kininogen-1, Gelsolin, Interleukin-1 receptor accessory protein, Serum amyloid A-1 protein, Serum amyloid A-2 protein.

Embodiment 19. The method of any one of Embodiments 14-18, wherein the protein comprises at least one selected from the group consisting of IgG, IgM, and total serum protein.

Embodiment 20. The method of any one of Embodiments 14-19, wherein the glycosylation profile of the protein in the subject is compared with at least one of a glycosylation profile indicating acute Lyme disease, a glycosylation profile indicating disseminated Lyme disease, a glycosylation profile indicating a state of recovering from Lyme disease, a glycosylation profile indicating a recovered case of Lyme disease, and a glycosylation profile indicating a non-Lyme infection or inflammatory disease.

Embodiment 21. The method of any one of Embodiments 14-20, wherein the method determines the stage of Lyme disease in addition to the absence or presence of Lyme disease.

Embodiment 22. The method of Embodiment 21, wherein the stage of Lyme disease includes acute Lyme disease, disseminated Lyme disease, state of recovering from Lyme disease, or reinfection with Lyme disease.

Embodiment 23. The method of any one of Embodiments 14-22, further comprises detecting an anti-*Borrelia* antibody in the subject.

Embodiment 24. The method of any one of Embodiments 14-23, wherein determining the glycosylation profile of the protein in the subject comprises at least one selected from the group consisting of: purifying the protein from a sample of the subject and releasing glycans from the protein.

Embodiment 25. The method of any one of Embodiments 14-24, wherein the glycosylation profile of the protein in the subject and/or the predetermined glycosylation profiles are determined by a matrix-assisted laser desorption/ionization (MALDI) mass spectrometry-based method, a high-performance liquid chromatography (HPLC)-based method, or an enzyme-linked immunosorbent assay (ELISA)-based method.

Embodiment 26. The method of any one of Embodiments 14-25, wherein the method confirms and treats an acute Lyme disease in the subject before seroconversion.

Embodiment 27. The method of Embodiment 14-26, wherein the compound comprises an antibiotic effective for killing a *Borrelia* bacteria.

Embodiment 28. The method of Embodiment 27, wherein the antibiotic comprises at least one selected from the group consisting of doxycycline, amoxicillin, a cephalosporin, and azithromycin.

Embodiment 29. A method of evaluation a treatment of Lyme disease, the method comprising: determining a glycosylation profile of a protein in the subject after the subject has been diagnosed with and received treatment for Lyme disease; and comparing the glycosylation profile of the protein in the subject with a predetermined glycosylation profile indicating a state of recovering from Lyme disease, a predetermined glycosylation profile indicating recovered from Lyme disease, and a predetermined glycosylation profile indicating neither recovering nor recovered.

Embodiment 30. The method of Embodiment 29, wherein the protein comprises at least one selected from the group consisting of Immunoglobulin G (IgG), Immunoglobulin M (IgM), Complement component 9, pentraxin-related C-reactive protein, Cystatin E/M, Peptidoglycan recognition protein 2, Afamin, fructose-bisphosphate Aldolase B, Apolipoprotein A-IV, Apolipoprotein B, Complement factor H related 1, Coagulation factor IX, Fructose-1,6-bisphosphatase 1, Vitamin D-binding protein-macrophage activating factor, Interalpha (globulin) inhibitor H2, Inter-alpha-trypsin inhibitor 4, Platelet factor 4 (CXCL7), S100 calcium binding protein A9, pentraxin-related C-reactive protein, Serum amyloid A-1 protein, C-X-C motif chemokine 9, C-X-C motif chemokine 10, C-C motif chemokine 19, pentraxin-related C-reactive protein, Complement component 9, Interalpha (globulin) inhibitor H2, Kininogen-1, Gelsolin, Interleukin-1 receptor accessory protein, Serum amyloid A-1 protein, Serum amyloid A-2 protein.

Embodiment 31. The method of any one of Embodiments 29-30, wherein the protein comprises at least one selected from the group consisting of IgG, IgM, and total serum protein.

Embodiment 32. The method of any one of Embodiments 29-31, further comprises detecting an anti-*Borrelia* antibody in the subject.

Embodiment 33. The method of any one of Embodiments 29-32, wherein determining the glycosylation profile of the protein in the subject comprises at least one selected from the group consisting of: purifying the protein from a sample of the subject and releasing glycans from the protein.

Embodiment 34. The method of any one of Embodiments 29-33, wherein the glycosylation profile of the protein in the subject and/or the predetermined glycosylation profiles are determined by a matrix-assisted laser desorption/ionization (MALDI) mass spectrometry-based method, a high-performance liquid chromatography (HPLC)-based method, or an enzyme-linked immunosorbent assay (ELISA)-based method.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method of diagnosing and treating Lyme disease in a subject, comprising:

measuring a sialic acid glycosylation profile of IgG or IgM in a serum sample of a subject suspected of suffering from Lyme disease;

comparing the measured sialic acid glycosylation profile obtained from the subject with a first reference glycosylation profile indicating free of Lyme disease or a second reference glycosylation profile indicating Lyme disease, wherein the subject is diagnosed with Lyme disease if the measured sialic acid glycosylation profile is different from the first reference glycosylation profile, wherein the difference comprises an increased level of sialic acid glycosylation, or the measured sialic acid glycosylation profile matches the second reference glycosylation profile, wherein both the measured sialic acid glycosylation profile and the second reference glycosylation profile comprises an increased level of sialic acid glycosylation, and wherein the subject is a human subject; identifying the subject as having Lyme disease, and administering to the subject an antibiotic effective to kill a *Borrelia* bacteria.

2. The method of claim 1, further comprising measuring one or more additional glycosylation profiles of IgG or IgM in the serum sample; and comparing the one or more additional measured glycosylation profiles to the first reference glycosylation profile or the second reference glycosylation profile.

3. The method of claim 2, wherein the one or more additional measured glycosylation profiles comprises a decreased level of terminal galactose structures.

4. The method of claim 1, further comprises detecting an anti-*Borrelia* antibody in the subject.

5. The method of claim 1, wherein the method further comprises at least one selected from the group consisting of:

purifying the IgG or IgM from the serum sample; and releasing glycans from the IgG or IgM.

6. The method of claim 1, wherein the sialic acid glycosylation profile is measured by a mass spectrometry-based method, a high-performance or ultra-performance liquid chromatography (HPLC/UPLC)-based method, or an enzyme-linked or immunosorbent assay (ELISA)-based method.

7. The method of claim 1, wherein the method diagnoses and treats an acute Lyme disease in the subject.

8. The method of claim 1, wherein the antibiotic is selected from the group consisting of doxycycline, amoxicillin, a cephalosporin, and azithromycin.

* * * * *